US012790629B2

(12) United States Patent
Atsumi et al.

(10) Patent No.: US 12,790,629 B2
(45) Date of Patent: Nov. 10, 2026

(54) METHODS FOR PRODUCTION OF FUCOSYLATED OLIGOSACCHARIDES IN RECOMBINANT CELL CULTURE

(71) Applicant: The Regents of the University of California, Oakland, CA (US)

(72) Inventors: Shota Atsumi, Davis, CA (US); Angela Zhang, Davis, CA (US); Xi Chen, Davis, CA (US); Yuanyuan Bai, Davis, CA (US); Hai Yu, Davis, CA (US); John B. McArthur, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 441 days.

(21) Appl. No.: 18/450,181

(22) Filed: Aug. 15, 2023

(65) Prior Publication Data

US 2024/0011064 A1 Jan. 11, 2024

Related U.S. Application Data

(63) Continuation of application No. PCT/US2022/017074, filed on Feb. 18, 2022.

(60) Provisional application No. 63/151,557, filed on Feb. 19, 2021.

(51) Int. Cl.

| | |
|---|---|
| ***C12P 19/18*** | (2006.01) |
| ***A23C 21/02*** | (2025.01) |
| ***A23C 21/04*** | (2025.01) |
| ***A23L 35/00*** | (2016.01) |
| ***C12N 9/10*** | (2006.01) |
| ***C12N 9/12*** | (2006.01) |
| ***C12N 15/63*** | (2006.01) |
| ***C12P 19/04*** | (2006.01) |

(52) U.S. Cl.

CPC ............ *C12P 19/04* (2013.01); *C12N 9/1051* (2013.01); *C12N 9/1241* (2013.01); *C12Y 204/01069* (2013.01); *C12Y 207/07064* (2013.01)

(58) Field of Classification Search

CPC ........ C12P 19/18; C12N 15/63; A23L 33/125; A23L 33/21; A23L 33/00

See application file for complete search history.

(56) References Cited

U.S. PATENT DOCUMENTS

| | | | |
|---|---|---|---|
| 6,461,835 | B1 | 10/2002 | Cummings et al. |
| 2011/0111458 | A1 | 5/2011 | Masuda et al. |
| 2011/0300584 | A1 | 12/2011 | Huefner et al. |
| 2017/0081353 | A1 | 3/2017 | McCoy et al. |
| 2020/0181665 | A1 | 6/2020 | Jennewein et al. |

FOREIGN PATENT DOCUMENTS

| | | | |
|---|---|---|---|
| AU | 2012217650 | B9 | 9/2017 |
| WO | 2012112777 | A2 | 8/2012 |

OTHER PUBLICATIONS

Agoston et al., Kilogram Scale Chemical Synthesis of 2'-fucosyllactose, Carbohydrate Research, vol. 476, Apr. 1, 2019, pp. 71-77.
Ayechu-Muruzabal et al., Diversity of Human Milk Oligosaccharides and Effects on Early Life Immune Development, Frontiers in Pediatrics, vol. 6, Sep. 10, 2018, 9 pages.
Baba et al., Construction of *Escherichia coli* K-12 in-frame, Single-gene Knockout Mutants: The Keio Collection, Molecular Systems Biology, vol. 2, 2006, 11 pages.
Bai et al., Biochemical Characterization of Helicobacter Pylori α1-3-fucosyltransferase and its Application in the Synthesis of Fucosylated Human Milk Oligosaccharides, Carbohydrate Research, vol. 480, Jul. 1, 2019, 18 pages.
Ballard et al., Human Milk Composition: Nutrients and Bioactive Factors, Pediatric Clinics of North America, vol. 60, No. 1, Feb. 2013, 24 pages.
Bandara et al., Chemical Synthesis of Human Milk Oligosaccharides: Lacto-N-neohexaose (Galβ1 → 4GlcNAcβ1→)2 3,6Gal-β1 → 4Glc, Organic & Biomolecular Chemistry, vol. 18, No. 9, Mar. 4, 2020, 16 pages.
Bandara et al., The Chemical Synthesis of Human Milk Oligosaccharides: Lacto-N-tetraose (Galβ1→3GlcNAcβ1→3Galβ1→4Glc), Carbohydrate Research, vol. 486, Dec. 1, 2019, 16 pages.
Baumgartner, et al., Construction of *Escherichia coli* Strains with Chromosomally Integrated Expression Cassettes for the Synthesis of 2'-fucosyllactose, Microbial Cell Factories, vol. 12, May 1, 2013, pp. 1-13.
Bassalo et al., Rapid and Efficient One-step Metabolic Pathway Integration in *E. coli*, ACS Synthetic Biology, vol. 5, No., 7, Jul. 15, 2016, pp. 561-568.
Baumgartner et al., Synthesis of the Human Milk Oligosaccharide Lacto-N-tetraose in Metabolically Engineered, Plasmid-free *E. coli*, Chembiochem: a European Journal of Chemical Biology, vol. 15, No. 13, Sep. 5, 2014, pp. 1896-1900.
Becker et al., Metabolically Engineered Corynebacterium Glutamicum for Bio-based Production of Chemicals, Fuels, Materials, and Healthcare Products, Metabolic Engineering, vol. 50, Nov. 2018, pp. 122-141.

(Continued)

*Primary Examiner* — Maryam Monshipouri
(74) *Attorney, Agent, or Firm* — PABST PATENT GROUP LLP

(57) ABSTRACT

Methods for producing oligosaccharide products such as difucosylated oligosaccharides are disclosed. The methods include culturing recombinant cells in a cell culture medium comprising L-fucose, an oligosaccharide acceptor, and a carbon source. The cells are cultured under conditions in which a first fucosyltransferase polypeptide having a first substrate selectivity (e.g., an α1-2-fucosyltransferase polypeptide), a second fucosyltransferase polypeptide having a second substrate specificity (e.g., an α1-3-fucosyltransferase polypeptide), a nucleotide sugar pyrophosphorylase polypeptide, a lactose transporter polypeptide, and an L-fucose transporter polypeptide are expressed, and in which the oligosaccharide acceptor is converted to the difucosylated oligosaccharide. Recombinant cells for use in the methods are also described.

13 Claims, 11 Drawing Sheets

Specification includes a Sequence Listing.

(56) References Cited

OTHER PUBLICATIONS

Berger et al., Human Milk Oligosaccharide 2'-fucosyllactose Links Feedings at 1 Month to Cognitive Development at 24 Months in Infants of Normal and Overweight Mothers, PloS One, vol. 15, No. 2, Feb. 12, 2020, pp. 1-12.
Bode, Human Milk Oligosaccharides: Every Baby Needs a Sugar Mama, Glycobiology, vol. 22, No. 9, Sep. 2012, pp. 1147-1162.
Borewicz et al., The Association Between Breastmilk Oligosaccharides and Faecal Microbiota in Healthy Breastfed Infants at Two, Six, and Twelve Weeks of Age, Scientific Reports, vol. 10, No. 1, Mar. 6, 2020, 12 pages.
Breton et al., Structures and Mechanisms of Glycosyltransferases, Glycobiology, vol. 16, No. 2, Feb. 2006, pp. 29R-37R.
Bruckner et al., Carbon Catabolite Repression in Bacteria: Choice of the Carbon Source and Autoregulatory Limitation of Sugar Utilization, FEMS Microbiology Letters, vol. 209, No. 2, Apr. 9, 2002, pp. 141-148.
Chaturvedi et al., Fucosylated Human Milk Oligosaccharides Vary Between Individuals and Over the Course of Lactation, Glycobiology, vol. 11, No. 5, May 2001, pp. 365-372.
Chen, Human Milk Oligosaccharides (HMOS): Structure, Function, and Enzyme-Catalyzed Synthesis, Advances in Carbohydrate Chemistry and Biochemistry, vol. 72, 2015, 59 pages.
Chin, et al., Metabolic Engineering of *Escherichia coli* to Produce 2'-Fucosyllactose via Salvage Pathway of Guanosine 5'-Diphosphate (GDP)-L-Fucose, Biotechnology and Bioengineering, vol. 113, No. 11, Nov. 2016, pp. 2443-2452.
Choi et al., Biosynthesis of the Human Milk Oligosaccharide 3-fucosyllactose in Metabolically Engineered *Escherichia coli* via the Salvage Pathway Through Increasing GTP Synthesis and α-Galactosidase Modification, Biotechnology and Bioengineering, vol. 116, No. 12, Dec. 2019, pp. 3324-3332.
Datsenko et al., One-step Inactivation of Chromosomal Genes in *Escherichia coli* K-12 Using Pcr Products, Proceedings of the National Academy of Sciences, vol. 97, No. 12, 2000, pp. 6640-6645.
Dong et al., Modular Pathway Engineering of Key Precursor Supply Pathways for Lacto- N-neotetraose Production in Bacillus Subtilis, Biotechnology for Biofuels, vol. 12, Sep. 9, 2019, pp. 1-11.
Drula et al., The Carbohydrate-active Enzyme Database: Functions and Literature, Nucleic Acids Research, vol. 50, No. D1, Jan. 7, 2022, pp. D571-D577.
Eichenbaum et al., Use of the Lactococcal nisA Promoter to Regulate Gene Expression in Gram-Positive Bacteria: Comparison of Induction Level and Promoter Strength, Applied and Environmental Microbiology, vol. 64, No. 8, Sep. 1998, pp. 2763-2769.
Engels et al., WbgL: A Novel Bacterial α1,2-Fucosyltransferase for the Synthesis of 2'-Fucosyllactose, Glycobiology, vol. 24, No. 2, Feb. 2014, pp. 170-178.
Gorke et al., Carbon Catabolite Repression in Bacteria: Many Ways to Make the Most Out of Nutrients, Nature Reviews, Microbiology, vol. 6, No., 8, Aug. 2008, pp. 613-624.
Hegar et al., The Role of Two Human Milk Oligosaccharides, 2'-Fucosyllactose and Lacto-N-Neotetraose, in Infant Nutrition, Pediatric Gastroenterology, Hepatology & Nutrition, vol. 22, No., 4, Jul. 2019, pp. 330-340.
Huang et al., Metabolic Engineering of *Escherichia coli* for the Production of 2'-fucosyllactose and 3-fucosyllactose Through Modular Pathway Enhancement, Metabolic Engineering, vol. 41, May 2017, pp. 23-38.
Jiang et al., Multigene Editing in the *Escherichia coli* Genome via the CRISPR-Cas9 System, Applied and Environmental Microbiology, vol. 81, No. 7, Apr. 2015, pp. 2506-2514.
Kaspar et al., Bioactive Secondary Metabolites from Bacillus Subtilis: a Comprehensive Review, Journal of Natural Products, vol. 82, No. 7, Jul. 26, 2019, pp. 2038-2053.
Konig et al., Multiple Stepwise Gene Knockout Using CRISPR/Cas9 in *Escherichia coli*, Bio-protocol, vol. 8, No. 2, Jan. 20, 2018, 18 pages.
Kopp et al., Impact of Glycerol as Carbon Source onto Specific Sugar and Inducer Uptake Rates and Inclusion Body Productivity in *E. coli* BL21(DE3), Bioengineering, vol. 5, No. 1, Dec. 21, 2017, pp. 1-15.
Kulinich et al., Human Milk Oligosaccharides: The Role in the Fine-tuning of Innate Immune Responses, Carbohydrate Research, vol. 432, Sep. 2, 2016, pp. 62-70.
Li et al., Harnessing Homologous Recombination in Vitro to Generate Recombinant DNA via SLIC, Nature Methods, vol. 4, No. 3, Apr. 2007, pp. 251-256.
Lian et al., Recent Advances in Metabolic Engineering of *Saccharomyces cerevisiae*: New Tools and Their Applications, Metabolic Engineering, vol. 50, Nov. 2018, 93 pages.
Liu et al., Efficient Sequential Synthesis of Lacto-N-triose II and Lacto-N-neotetraose by a Novel β-N-acetylhexosaminidase from Tyzzerella Nexilis, Food Chemistry, vol. 332, Dec. 1, 2020.
Liu et al., Functional and Biochemical Characterization of *Escherichia coli* Sugar Efflux Transporters, Journal of Biological Chemistry, vol. 274, No. 33, Sep. 1999, pp. 22977-22984.
Lutz et al., Independent and Tight Regulation of Transcriptional Units in *Escherichia coli* via the LacR/O, the TetR/O and AraC/I1-I2 Regulatory Elements, Nucleic Acids Research, vol. 25, No. 6, Mar. 15, 1997, pp. 1203-1210.
Ma et al., Purification, Kinetic Characterization, and Mapping of the Minimal Catalytic Domain and the Key Polar Groups of Helicobacter pylori-(1,3/1,4)-Fucosyltransferases, Journal of Biological Chemistry, vol. 281, No. 10, Apr. 2006, pp. 6385-6394.
McArthur et al., A Bacterial β1-3-Galactosyltransferase Enables Multigram-Scale Synthesis of Human Milk Lacto-N-tetraose (LNT) and Its Fucosides, ACS Catalysis, vol. 9, No. 12, Dec. 6, 2019, pp. 10721-10726.
Newburg et al., Lactodifucotetraose, A Human Milk Oligosaccharide, Attenuates Platelet Function and Inflammatory Cytokine Release, Journal of Thrombosis and Thrombolysis, vol. 42, No. 1, Jul. 2016, pp. 46-55.
Nidetzky et al., Leloir Glycosyltransferases as Biocatalysts for Chemical Production, ACS Catalysis, vol. 8, No. 7, May 2018, pp. 6283-6300.
Orczyk-Pawilowicz et al., The Impact of Dietary Fucosylated Oligosaccharides and Glycoproteins of Human Milk on Infant Well-Being, Nutrients, vol. 12, No. 4, Apr. 16, 2020, pp. 1-26.
Park et al., Characterization and Role of Fucose Mutarotase in Mammalian Cells, Glycobiology, vol. 17, No. 9, Jun. 29, 2007, pp. 1-22.
Paulsen et al., Characterization of Glucose-Specific Catabolite Repression-Resistant Mutants of Bacillus subtilis: Identification of a Novel Hexose: H+Symporter, Journal of Bacteriology, vol. 180, No. 3, Feb. 1998, pp. 498-504.
International Application No. International Search Report and Written Opinion in PCT/US2022/017074 mailed on Jun. 8, 2022, 13 pages.
Rasko et al., Cloning and Characterization of the Alpha (1,3/4) Fucosyltransferase of Helicobacter Pylori, Journal of Biological Chemistry, vol. 275, No. 7, Feb. 18, 2000, pp. 4988-4994.
Rosano et al., Recombinant Protein Expression in *Escherichia coli*: Advances and Challenges, Frontiers in Microbiology, vol. 5, Apr. 17, 2014, pp. 1-17.
Rud et al., A Synthetic Promoter Library for Constitutive Gene Expression in Lactobacillus Plantarum, Microbiology, vol. 152, No. Pt 4, Apr. 2006, pp. 1011-1019.
Rudloff et al., Milk Oligosaccharides and Metabolism in Infants, Available online at: https://www.ncbi.nlm.nih.gov/pmc/articles/PMC3649476/pdf/398S.pdf, May 1, 2012, pp. 398S-405S.
Sakanaka et al., Evolutionary Adaptation in Fucosyllactose Uptake Systems Supports Bifidobacteria-Infant Symbiosis, Scientific Advances, vol. 5, Issue 8, Aug. 28, 2019, pp. 1-15.
Seydametova et al., Search for Bacterial α1,2-Fucosyltransferases for Whole-Cell Biosynthesis of 2'-fucosyllactose in Recombinant *Escherichia coli*, Microbiological Research, vol. 222, Feb. 25, 2019, pp. 35-42.

(56) References Cited

OTHER PUBLICATIONS

Shen, et al., Development of a Novel, Robust and Cost-efficient Process for Valorizing Dairy Waste Exemplified by Ethanol Production, Microbial Cell Factories, vol. 18, Mar. 11, 2019, pp. 1-10.
Shin et al., Development of Fluorescent *Escherichia coli* for a Whole-cell Sensor of 2'-Fucosyllactose, Available online at: https://www.ncbi.nlm.nih.gov/pmc/articles/PMC7324612/pdf/41598_2020_Article_67359.pdf, Jun. 29, 2020, 8 pages.
Smilowitz et al., Breast Milk Oligosaccharides: Structure-Function Relationships in the Neonate, Annual Review of Nutrition, 2014, pp. 143-169.
Triantis et al., Immunological Effects of Human Milk Oligosaccharides, Frontiers in Pediatrics, Jul. 2, 2018, pp. 1-14.
Wicinski, Human Milk Oligosaccharides: Health Benefits, Potential Applications in Infant Formulas, and Pharmacology, Nutrients, Available online at: https://www.ncbi.nlm.nih.gov/pmc/articles/PMC7019891/pdf/nutrients-12-00266.pdf, Jan. 20, 2020, pp. 1-14.
Xiao et al., Chemoenzymatic Synthesis of a Library of Human Milk Oligosaccharides, The Journal of Organic Chemistry, vol. 81, No. 14, Jul. 15, 2016, pp. 5851-5865.
Ye et al., Reprogramming the Enzymatic Assembly Line for Site-Specific Fucosylation, Nature Catalysis, May 6, 2019, pp. 514-522.
Yi et al., Remodeling Bacterial Polysaccharides by Metabolic Pathway Engineering, Proceedings of the National Academy of Sciences, vol. 106, No. 11, Mar. 17, 2009, pp. 4207-4212.
Yoneda, et al., Biological Production of 2-butanone in *Escherichia coli*, ChemSusChem, vol. 7, No. 1, Jan. 2014, pp. 92-95.
Yu et al., Highly Efficient Chemoenzymatic Synthesis of β1-4-Linked Galactosides with Promiscuous Bacterial β1-4-Galactosyltransferases, Chemical Communications, vol. 46, No. 33, Sep. 7, 2010, pp. 6066-6068.
Yu et al., Chapter 11 Enzymatic and Chemoenzymatic Synthesis of Human Milk Oligosaccharides (HMOS), In: Synthetic Glycomes, The Royal Society of Chemistry, Apr. 2019, pp. 254-280.
Yu et al., Helicobacter Pylori α1-3/4-Fucosyltransferase (Hp3/4ftFT)-Catalyzed One-Pot Multienzyme (OPME) Synthesis of Lewis Antigens and Human Milk Fucosides, Chemical Communications, vol. 53, No. 80, Oct. 5, 2017, pp. 1-10.
Yu et al., Production of a Human Milk Oligosaccharide 2'-Fucosyllactose by Metabolically Engineered *Saccharomyces cerevisiae*, Microbial Cell Factories, vol. 17, No. 101, 2018, pp. 1-10.
Zhang, et al., Microbial Production of Human Milk Oligosaccharide Lactodifucotetraose Supplementary Material, pp. S1-S14.
Zhang, et al., Microbial Production of Human Milk Oligosaccharide Lactodifucotetraose Metabolic Engineering, vol. 66, Jul. 2021, pp. 12-20.
Zhao et al., Development of a Fast and Easy Method for *Escherichia coli* Genome Editing with CRISPR/Cas9, Microbial Cell Factories, vol. 15, No. 1, Dec. 1, 2016, pp. 1-9.
Zhao et al., The One-Pot Multienzyme (OPME) Synthesis of Human Blood Group H Antigens and a Human Milk Oligosaccharide (HMOS) With Highly Active Thermosynechococcus Elongates α1-2-Fucosyltransferase, Available online at: https://www.ncbi.nlm.nih.gov/pmc/articles/PMC4775349/pdf/nihms759933.pdf, Mar. 11, 2016, pp. 3899-3902.

| | | | | | | | |
|---|---|---|---|---|---|---|---|
| Fucose (g/L) | 1 | 0 | 1 | 2 | 3 | 0 | 3 |
| Lactose (g/L) | 0 | 1 | 1 | 2 | 0 | 3 | 3 |
| $OD_{600}$ | 13.4 ± 0.8 | 12.7 ± 0.8 | 14.0 ± 0.5 | 11.7 ± 0.2 | 13.4 ± 0.6 | 13.1 ± 0.9 | 13.1 ± 0.2 |

FIG. 12

| Input | Enzyme | Intermediate | Glycosyl-transferase | Acceptor | Intermediate | Glycosyl-transferase | Product |
|---|---|---|---|---|---|---|---|
| Fucose | FKP | GDP-fucose | WbgL<br>Hm2FT<br>WbsJ<br>Hp2FTa<br>Hp2FTb | Lactose  | 2'-FL 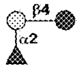 | Hp3/4FT or Hp3FT | LDFT 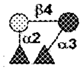 |
| Fucose | FKP | GDP-fucose | WbgL<br>Hm2FT<br>WbsJ<br>Te2FT | LNT 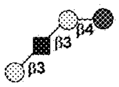 | LNFP I 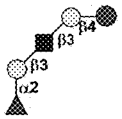 | Hp3/4FT or Hp4FT | DF-LNT 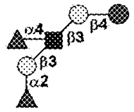 |
| Fucose | FKP | GDP-fucose | WbgL<br>Hm2FT<br>WbsJ<br>Te2FT | LNT 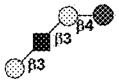 | LNFP I 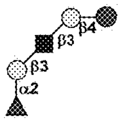 | Hp3/4FT | TriF-LNT 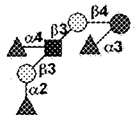 |
| Fucose | FKP | GDP-fucose | WbgL<br>Hm2FT<br>WbsJ<br>Te2FT | *p*LNH 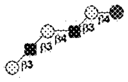 | F-*p*LNH I 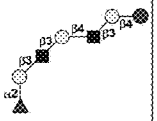 | Hp3/4FT | TriF-*p*LNH I 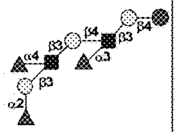 |
| Fucose | FKP | GDP-fucose | WbgL<br>Hm2FT<br>WbsJ<br>Te2FT | *p*LNO  | F-*p*LNO I  | Hp3/4FT | TetraF-*p*LNO 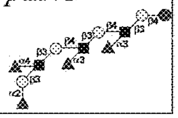 |

Symbols: ▲ L-fucose (Fuc); ○ D-galactose (Gal); ■ *N*-acetyl-D-glucosamine (GlcNAc); ● D-glucose (Glc). GenBank accession numbers: FKP (GenBank: CAH08307.1), WbgL (GenBank: ABE98421.1), Hm2FT (GenBank: CBG40460), WbsJ (GenBank: AAO37698.1), Hp2FTa from *Helicobacter pylori* UA1234 (GenBank: AAD29863.1), Hp2FTb from *Helicobacter pylori* UA802 (GenBank: AAC99764.1), Te2FT (GenBank: BAC08546.1), Hp3/4FT (GenBank: AAF35291.2), Hp3FT (GenBank: AAB93985.1, AAD06169.1, AAD06573.1, AAB81031.1), Hp4FT (GenBank AAR88243.1).

METHODS FOR PRODUCTION OF FUCOSYLATED OLIGOSACCHARIDES IN RECOMBINANT CELL CULTURE

CROSS-REFERENCES TO RELATED APPLICATIONS

The present application is a bypass continuation of International Application PCT/US2022/017074 filed Feb. 18, 2022, which claims priority to U.S. Provisional Patent Application No. 63/151,557, filed on Feb. 19, 2021, which applications are incorporated herein by reference in their entireties.

SEQUENCE LISTING

The instant application contains a Sequence Listing which has been submitted electronically in XML file format and is hereby incorporated by reference in its entirety. Said XML copy, created on Aug. 11, 2023, is named 081906-1390975_242010US_SL.xml and is 175,778 bytes in size.

BACKGROUND OF THE INVENTION

Human milk oligosaccharides (HMOs) are a class of over 200 compounds present at 20-23 g/L in colostrum and 12-14 g/L in mature milk (Chen, 2015; Smilowitz et al., 2014; Wiciński et al., 2020; Yu and Chen, 2019). Unlike their common precursor lactose, HMOs are indigestible by human infants and instead improve neonatal health by serving as effective antimicrobials and antivirals, prebiotics, and regulators of inflammatory immune cell-response cascades (Ayechu-Muruzabal et al., 2018; Ballard and Morrow, 2013; Kulinich and Liu, 2016; Rudloff and Kunz, 2012; Triantis et al., 2018; Wicinski et al., 2020). These and other potential benefits of HMOs make them attractive targets of study for preventing or treating diseases in both children and adults (Wiciński et al., 2020). The bioactive properties of HMOs have motivated efforts to define mechanistic effects of individual compounds (Berger et al., 2020; Bode, 2012; Borewicz et al., 2020; Hegar et al., 2019), but the sources of HMOs are limited and their large-scale isolation for such studies is exceedingly difficult. While production of individual HMOs using in vitro enzymatic reactions has been successful (Ågoston et al., 2019; Bai et al., 2019; Bandara et al., 2019, 2020; McArthur et al., 2019; Xiao et al., 2016; Yu et al., 2017; Zhao et al., 2016), these methods require supplementation of stoichiometric amounts of ATP and other cofactors that increase the production cost and may complicate the purification process of the oligosaccharide products.

Microbial production is a viable alternative method to produce HMOs. Whole cell biocatalysts are self-maintaining systems and do not require an exogenous supply of expensive cofactors. Enzymatic reactions in cells can also achieve high regio- and stereo-specific production of structurally complex molecules. Several simple HMOs including 2'-FL, 3-FL, lacto-N-triose II, lacto-N-tetraose (LNT), and lacto-N-neotraose (LNnT) have been produced in engineered microorganisms (Baumgartner et al., 2014; Choi et al., 2019; Dong et al., 2019; Huang et al., 2017; Liu et al., 2020; Yu et al., 2018). Linear HMO backbones such as lactose, LNT, and LNnT can be glycosylated at multiple sites with fucose and sialic acid to further produce HMOs of higher structural complexity. While in vitro enzymatic synthesis can construct these decorated HMOs by strategically producing each intermediate HMO structure in individual reaction systems, microbial production of multi-glycosylated HMOs in a microbial host has not been demonstrated.

Tetrasaccharide lactodifucotetraose (LDFT) is one of the most abundant fucosylated HMOs and is produced at an average of 0.43 g/L over the first year of lactation by secretory mothers (Chaturvedi et al., 2001). Its structure consists of a core lactose unit that is fucosylated at the C2' and C3 positions. Studies have shown that LDFT is effective in preventing *Campylobacter jejuni*-associated diarrhea and suppressing platelet-induced inflammatory processes in neonates (Newburg et al., 2016; Orczyk-Pawilowicz and Lis-Kuberka, 2020). Its activity as a gastrointestinal and immunological modulator has motivated further research into its potential therapeutic applications. However, the high cost and limited availability of LDFT in the market ($140/mg, Biosynth Carbosynth; €11,000/g Elicityl) are barriers to these biological studies.

BRIEF SUMMARY OF THE INVENTION

Provided herein are recombinants cell for production of oligosaccharide products such as difucosylated oligosaccharides. The cells include: a polynucleotide encoding a first glycosyltransferase polypeptide having a first substrate selectivity and a polynucleotide encoding a second glycosyltransferase polypeptide having a second substrate selectivity, and may further include one or more polynucleotides selected from the group consisting of: a polynucleotide encoding a nucleotide sugar pyrophosphorylase polypeptide, a monosaccharide transporter polypeptide, and an oligosaccharide transporter polypeptide.

In some embodiments, the cells include:

- a polynucleotide encoding a first fucosyltransferase polypeptide having a first substrate specificity (e.g., an α1-2-fucosyltransferase polypeptide),
- a polynucleotide encoding a second fucosyltransferase polypeptide having a second substrate specificity (e.g., an α1-3-fucosyltransferase polypeptide), and
- optionally one more polynucleotides encoding a nucleotide sugar pyrophosphorylase polypeptide, a lactose transporter polypeptide, and a polynucleotide encoding an L-fucose transporter polypeptide.

Also provided herein are methods for producing difucosylated oligosaccharides and other oligosaccharide products. In some embodiments, the methods include culturing a recombinant cell as described herein in a cell culture medium comprising L-fucose, an oligosaccharide acceptor, and a carbon source; wherein the cell is cultured under conditions in which a first fucosyltransferase polypeptide, a second fucosyltransferase polypeptide, a nucleotide sugar pyrophosphorylase polypeptide, a lactose transporter polypeptide, and an L-fucose transporter polypeptide are expressed and the oligosaccharide acceptor is converted to the difucosylated oligosaccharide.

BRIEF DESCRIPTION OF THE DRAWINGS

FIG. 12 shows fucosyltransferases and other enzymes for production of oligosaccharide products in recombination host cells.

DETAILED DESCRIPTION OF THE INVENTION

Figure 1:
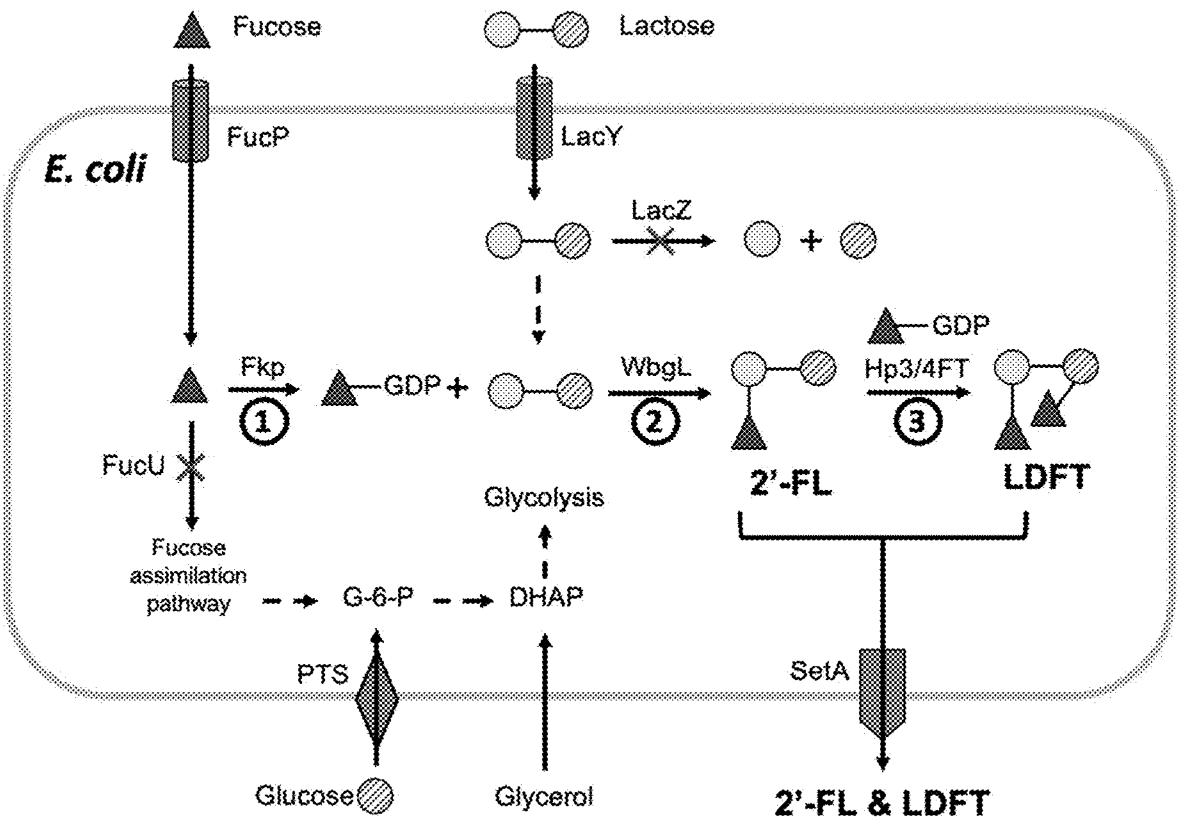
FIG. 1 shows a summary of various pathway design aspects for LDFT production in *E. coli* according to the present disclosure. L-Fucose (triangles) and lactose (glucose moiety, diagonal striped circles; galactose moiety, filled circles) are transported into the cytosol through sugar transporters FucP and LacY, respectively. The fucU and lacZ genes are deleted to prevent substrate assimilation into central carbon metabolism. Fucose is converted to donor substrate GDP-fucose by Fkp. WbgL glycosylates lactose at the C2' position with GDP-fucose to form 2'-FL. Hp3/4FT glycosylates 2'-FL at the C3 position with GDP-fucose to form LDFT. G-6-P: glucose-6-phosphate, DHAP: dihydroxyacetone phosphate, PTS: phosphotransferase system, SetA: sugar efflux transporter A.

Provided herein are methods for producing oligosaccharide products, such as tetrasaccharide lactodifucotetraose (LDFT) and other difucosylated oligosaccharides, in recombinant hosts such as *E. coli*. The present invention is based, in part, on the pairing of glycosyltransferases with complementary substrate specificities, e.g., pairing of α1-2-fucosyltransferases with high activity towards lactose and α1-3-fucosyltransferases with higher activity towards 2'-fucosyllactose (2'-FL) than lactose. The selectivity of the α1-3-fucosyltransferase provides for minimal production of 3-fucosyllactose (3-FL) as a side product, resulting in the production of difucosylated oligosaccharides such as difucosylated tetrasaccharide lactodifucotetraose (LDFT) in high yield.

The use of bacterial fucosyltransferases with narrow acceptor selectivity can drive the sequential fucosylation of acceptors such as lactose and intermediates such as 2'-fucosyllactose (2'-FL) to produce LDFT and other fucosylated products. Deletion of substrate degradation pathways that decouple cellular growth from product fucosylation can enhance expression of native substrate transporters, and modular induction of the genes in relevant biosynthetic pathways allows for complete conversion of acceptors such as lactose into products such as LDFT with only minor quantities of side products such as 3-fucosyllactose (3-FL). In certain embodiments, for example, 5.1 g/L of LDFT can be produced from 3 g/L lactose and 3 g/L L-fucose in 24 h. The results described herein demonstrate promising applications of microbial biocatalysts for the production of multi-fucosylated HMOs.

LDFT can be synthesized from lactose and L-fucose in a two-step fucosylation process using an α1-2-fucosyltransferase and an α1-3-fucosyltransferase. While monofucosylation of lactose with a single fucosyltransferase for the microbial production of 2'-FL and 3-FL has been studied, the effects of implementing an α1-2-fucosyltransferase and an α1-3-fucosyltransferase together in a cellular system to produce a difucosylated HMO has not been reported. As lactose is a suitable acceptor substrate for both fucosyltransferases, both 2'-FL and 3-FL can be produced as monofucosylated products in the first fucosylation step of the system with the presence of both fucosyltransferases. It was shown previously that while an α1-3/4-fucosyltransferase from *Helicobacter pylori* (Hp3/4FT) can use both non-fucosylated and α1-2-fucosylated galactosyl oligosaccharides as substrates (McArthur et al., 2019; Yu et al., 2017), α1-2-fucosyltransferases from *Escherichia coli* 0126 (WbgL) (Engels and Elling, 2014; McArthur et al., 2019) and *Thermosynechococcus elongates* (Zhao et al., 2016) are selective towards lactose and other non-fucosylated galactosyl oligosaccharide acceptor substrates.

An *E. coli*-based system according to the present disclosure, for example, employs two fucosyltransferases that preferentially fucosylates lactose to form a 2'-FL intermediate that is further fucosylated to produce the target LDFT. Various promoter expression systems were assessed to establish heterologous expression of the desired biosynthetic pathway. LDFT production was decoupled from bacterial growth by removing catabolic pathways of starting substrates and by maintaining cell density with glycerol, an inexpensive carbon source that does not activate carbon catabolite repression of lactose and L-fucose transporters (Kopp et al., 2017; Paulsen et al., 1998). To enhance intracellular availability of substrates, the lactose and L-fucose transporter genes, lacY and fucP, were additionally expressed from plasmids. With additional fine-tuning of the expression levels of individual glycosyltransferase genes, the strain produced 5.1 g/L of LDFT from 3 g/L lactose, achieving 910% of the theoretical maximum yield of LDFT in 24 h.

I. RECOMBINANT HOST CELLS FOR PRODUCTION OF OLIGOSACCHARIDES

Provided herein are recombinant cells for the production of oligosaccharide products. The cells include:

- a polynucleotide encoding a first glycosyltransferase polypeptide having a first substrate selectivity, and
- a polynucleotide encoding a second glycosyltransferase polypeptide having a second substrate selectivity.

Glycosyltransferases and other enzymes suitable for use in the methods described herein include, but are not limited to, those summarized in FIG. 12. In some embodiments, the first glycosyltransferase is a fucosyltransferase having a first substrate selectivity and the second glycosyltransferase is a fucosyltransferase polypeptide having a second substrate selectivity.

A. α1-2-fucosyltransferase

Fucosyltransferases are inverting glycosyltransferases and are classified into eight glycosyltransferase (GT) families in the Carbohydrate-Active enZYmes (CAZy) database: GT10, GT11, GT23, GT3, GT56, GT65, GT68 and GT74 (see, cazy.org; Drula, et al. *Nucleic Acids Research,* 2022, Vol. 50, D571-D577; and references cited therein).

In some embodiments, the first fucosyltransferase polypeptide is an α1-2-fucosyltransferase polypeptide classified by Enzyme Commission number 2.4.1.69. WbgL, according to SEQ ID NO:1, and other GT11 family fucosyltransferases are thought to be GT-B fold glycosyltransferases containing two separate Rossmann domains (characterized by a six-stranded parallel β-sheet with a 321456 topology) with a connecting linker region and a catalytic site between the domains. See, Engels et al. (*Glycobiology* 2014, 24(2): 170-178) and Breton et al. (*Glycobiology* 2006, 16(2): 29R-37R). A high degree of conservation has been observed between protein members of the GT-B family, especially in the nucleotide-binding domain at the C-terminus. A glutamate residue and glycine-rich loops are thought to interact with the ribose and phosphate moieties of the nucleotide. The α1-2-fucosyltransferase may be a GT11 family fucosyltransferase having one or more conserved motifs corresponding to residues 8-16 (motif IV), 158-167 (motif I), 201-207 (motif II), and 234-273 (motif III) of SEQ ID NO:1. In some embodiments, the α1-2-fucosyltransferase includes from one to four amino acid sequences having at least 70% identity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity) to motif IV, motif I, motif, II, and/or motif III in SEQ ID NO:1. Highly conserved motif I is likely involved in GDP-fucose binding. Residues corresponding to $R^{161}$ and $D^{164}$ have been indicated to play roles in donor binding and enzyme activity (see, Li, et al. *Biochemistry* 2008, 47, 11590-11597). In addition to amino acid sequences corresponding to motifs I, II, III, and/or IV, the α1-2-fucosyltransferase may also include on or more acid sequences having at least 70% identity residues 1-7, 17-157, 168-200, 208-233, and/or 274-297 of SEQ ID NO:1.

Percentage of sequence identity can be determined by comparing two optimally aligned sequences over a comparison window, wherein the portion of the sequence (e.g., a peptide of the invention) in the comparison window may comprise additions or deletions (i.e., gaps) as compared to the reference sequence which does not comprise additions or deletions, for optimal alignment of the two sequences. The percentage can be calculated by determining the number of positions at which the identical amino acid residue occurs in both sequences to yield the number of matched positions, dividing the number of matched positions by the total number of positions in the window of comparison and multiplying the result by 100 to yield the percentage of sequence identity.

"Identical" and "identity," in the context of two or more polypeptide sequences or nucleic acid sequences, refer to two or more sequences or subsequences that are the same. Sequences are "substantially identical" to each other if they have a specified percentage of nucleotides or amino acid residues that are the same (e.g., at least 70%, at least 75%, at least 80%, at least 85%, at least 90%, at least 95%, or at least 99% identical over a specified region), when compared and aligned for maximum correspondence over a comparison window, or designated region as measured using one of the following sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Examples of algorithms that are suitable for determining percent sequence identity and sequence similarity are the BLAST and BLAST 2.0 algorithms, which are described in Altschul et al., (1990) *J. Mol. Biol.* 215: 403-410 and Altschul et al. (1977) *Nucleic Acids Res.* 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., *supra*). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see, e.g., Henikoff and Henikoff, *Proc. Natl. Acad. Sci. USA* 89:10915 (1989)).

Examples of α1-2-fucosyltransferases include, but are not limited to, *E. coli* O126 α1-2-fucosyltransferase ("WbgL;" GenBank: ABE98421.1; SEQ ID NO:1), *H. mustelae* 12198 α1-2-fucosyltransferase ("Hm2FT;" GenBank: CBG40460; SEQ ID NO:8), *E. coli* 0128:B12 α1-2-fucosyltransferase ("WbsJ;" GenBank: AAO37698.1; SEQ ID NO:9), *H. pylori* UA1234 α1-2-fucosyltransferase ("Hp2FTa;" GenBank: AAD29863.1; SEQ ID NO:10), and *H. pylori* UA802 α1-2-fucosyltransferase ("Hp2FTb;" GenBank: AAC99764.1; SEQ ID NO:11). In some embodiments, the α1-2-fucosyltransferase polypeptide comprises an amino acid sequence having at least 70% identity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity) to WbgL (SEQ ID NO: 1), Hm2FT (SEQ ID NO:8), WbsJ (SEQ ID NO:9), Hp2FTa (SEQ ID NO:10), or Hp2FTb (SEQ ID NO:11).

In some embodiments, the α1-2-fucosyltransferase polypeptide is an *E. coli* 0126 α1-2-fucosyltransferase WbgL polypeptide.

B. α1-3-fucosyltransferase

In some embodiments, the second fucosyltransferase polypeptide is an α1-3-fucosyltransferase polypeptide having, for example, β-LacNac α-1,3-L-fucosyltransferase activity (EC 2.4.4.1), galactoside α-1,3/1,4-L-fucosyltransferase activity (EC 2.4.1.65), or galactoside α-1,3-L-fucosyltransferase activity (EC 2.4.1.152). The α1-3-fucosyltransferase may be a GT10 family fucosyltransferase or a GT11 family fucosyltransferase. In some embodiments, the GT10 fucosyltransferase has a glycosyltransferase B (GT-B) fold containing two separated Rossmann domains as described, for example, by Breton et al. *supra.*

Examples of α1-3-fucosyltransferases include, but are not limited to *H. pylori* UA948 α1-3/4-fucosyltransferase ("Hp3/4FT;" GenBank: AAF35291.2; SEQ ID NO:3), *H. pylori* ATCC43504 α1-3-fucosyltransferase ("Hp43504 3FT;" GenBank: AAB93985; SEQ ID NO:12), *H. pylori* J99 α1-3-fucosyltransferase ("HpJ99 3FT;" GenBank: AAD06169.1, AAD06573.1; SEQ ID NOS:13-14), *H. pylori* NCTC11637 α1-3-fucosyltransferase ("Hp11637 3FT;" GenBank: AAB93985; SEQ ID NO:15), *B. fragilis* NCTC 9343 α1-3/α1-4-fucosyltransferase polypeptide ("Bf3/4FT;" GenBank: CAH09495.1; SEQ ID NO:16), and *H. hepaticus* ATCC 51449 Hh0072 ("Hh0072"; GenBank: AAP76669.1; SEQ ID NO:17). In some embodiments, the α1-2-fucosyltransferase polypeptide comprises an amino acid sequence having at least 70% identity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity) to Hp3/4FT (SEQ ID NO:3), Hp43504 3FT (SEQ ID NO:12), HpJ99 3FT (SEQ ID NOS:13 and/or 14), Hp11637 3FT (SEQ ID NO:15), Bf3/4FT (SEQ ID NO:16), or Hh0072 (SEQ ID NO:17).

In some embodiments, the α1-3-fucosyltransferase polypeptide is a truncated α1-3-fucosyltransferase polypeptide, e.g., residues 1-428 of SEQ ID NO:2, or a polypeptide having at least 70% identity to residues 1-428 of SEQ ID NO:2.

In some embodiments, the cells further include one or more polynucleotides selected from the group consisting of:

- a polynucleotide encoding a nucleotide sugar pyrophosphorylase,
- a polynucleotide encoding a monosaccharide transporter such as a fucose transporter, and
- a polynucleotide encoding an oligosaccharide transporter such as a lactose transporter.

C. Kinase/Pyrophosphorylases

In some embodiments, the nucleotide sugar pyrophosphorylase polypeptide is a bifunctional glycokinase and nucleotide sugar pyrophosphorylase polypeptide. In some embodiments, the bifunctional enzyme is an L-fucokinase/GDP-fucose pyrophosphorylase (Fkp). Fkps are a class of enzymes that catalyze two steps of the L-fucose salvage pathway for the generation of activated GDP-L-fucose via a fucose-1-phosphate intermediate. Fkps have been observed to adopt a tetrameric formation, with each monomer containing an N-terminal GDP-fucose pyrophosphorylase domain, an intermediate linking domain, and a C-terminal fucokinase domain. The pyrophosphorylase domain contains a Rossmann fold and a left-handed β-helix, and the fucokinase contains a GHMP sugar kinase fold. The linker between the two domains contains α-helices. Examples of Fkps include, but are not limited to *Bacteroides fragilis* bifunctional L fucokinase/GDP-L-fucose pyrophosphorylase ("BfFKP;" GenBank: CAH08307.1; SEQ ID NO:3) and Arabidopsis thaliana bifunctional fucokinase/fucose pyrophosphorylase ("AtFKGP;" UniProt: Q9LNJ9; SEQ ID NO:18).

D. Glycotransporters

In some embodiments, the monosaccharide transporter is a fucose transporter, and the oligosaccharide transporter is a lactose transporter. Many such transporters belong to the major facilitator superfamily (MFS), which shuttle substrates across cell membranes by leveraging electrochemical potential. MFS transporters such as *E. coli* LacY are composed of 12 transmembrane helices, with the six N-terminal and the six C-terminal helices forming distinct helical bundles connected by a loop. The two bundles have the same topology and exhibit pseudo-two-fold symmetry around an axis perpendicular to the membrane bilayer. A hydrophilic cavity is defined by helices 1, 2, 4, and 5 in the N-terminal bundle and helices 7, 8, 9, and 11 in the C-terminal bundle, while helices 3, 6, 9, and 12 are largely embedded in the membrane. In some embodiments, the lactose transporter polypeptide is an *E. coli* LacY polypeptide. Similar lactose transporters have been identified in *Citrobacter* spp., *Cronobacter* spp., *Enterobacter* spp., *Klebsiella* spp., *Salmonella* spp., and *Shigella* spp., and may also be incorporated in the recombinant host cells. In some embodiments, the lactose transporter polypeptide comprises an amino acid sequencing having at least 70% identity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity) to the *E. coli* str. K-12 substr. MG1655 LacY set forth in SEQ ID NO:4.

In some embodiments, the L-fucose transporter polypeptide is an *E. coli* FucP polypeptide. Similar fucose transporters have been identified in species including, but not limited to, *Chryseobacterium* mucoviscidosis, *Enterobacter hormaechei, Escherichia albertii, Klebsiella pneumoniae, Salmonella enterica*, and *Shigella flexneri*, and may also be incorporated into the recombinant host cells. In some embodiments, the lactose transporter polypeptide comprises an amino acid sequencing having at least 70% identity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity) to the *E. coli* str. K-12 substr. MG1655 FucP set forth in SEQ ID NO:5.

In some embodiments, the cell further includes a polynucleotide encoding an additional transporter polypeptide. In some embodiments, the additional transporter polypeptide is a *Bifidobacterium* fucosyllactose transporter polypeptide, e.g., those including the domains set forth in SEQ ID NOS:19-21 and/or SEQ ID NOS:22-24.

Suitable microbial hosts include, but are not limited to, members of the genera *Clostridium, Zymomonas, Escherichia, Salmonella, Rhodococcus, Pseudomonas, Bacillus, Lactobacillus, Enterococcus, Alcaligenes, Klebsiella, Paenibacillus, Arthrobacter, Corynebacterium, Brevibacterium, Pichia, Candida, Hansenula* and *Saccharomyces*. Preferred hosts include: *Escherichia coli, Alcaligenes eutrophus, Bacillus licheniformis, Paenibacillus macerans, Rhodococcus erythropolis, Pseudomonas putida, Lactobacillus plantarum, Enterococcus faecium, Enterococcus gallinarum, Enterococcus faecalis, Bacillus subtilis* and *Saccharomyces cerevisiae*. In some embodiments, the cell is an *E. coli* cell, a *B. subtilis* cell, a *C. glutamicum* cell, or an *S. cerevisiae* cell. In some embodiments, the cell is an *E. coli* BW25113 Z1 cell or an *E. coli* MG1655 Z1 cell.

Recombinant organisms containing the genes encoding glycosyltransferases and other enzymes for the production of human milk oligosaccharides and other oligosaccharide products can be constructed using techniques well known in the art. Polynucleotide sequences may be obtained from various organisms as described above, e.g., from a bacterial genome. For example, if the sequence of the gene is known, suitable genomic libraries may be created by restriction endonuclease digestion and may be screened with probes complementary to the desired gene sequence. Once the sequence is isolated, the DNA may be amplified using standard primer-directed amplification methods such as polymerase chain reaction to obtain amounts of DNA suitable for transformation using appropriate vectors. Tools for codon optimization for expression in a heterologous host are readily available.

Once the relevant pathway genes are identified and isolated they may be transformed into suitable expression hosts by means well known in the art. Vectors or cassettes useful for the transformation of a variety of host cells are common and commercially available from companies such as Thermo Fisher Scientific (Waltham, MA), MilliporeSigma (La Jolla, CA), and New England Biolabs, Inc. (Burlington, MA). Typically the vector or cassette contains sequences directing transcription and translation of the relevant gene, a selectable marker, and sequences allowing autonomous replication or chromosomal integration. Such vectors may include a region upstream of the gene which harbors transcriptional initiation controls and a region downstream of the gene which controls transcriptional termination. Both control regions may be derived from genes homologous to the transformed host cell, although it is to be understood that such control regions may also be derived from genes that are not native to the specific species chosen as a production host.

Initiation control regions or promoters, which are useful to drive expression of the relevant pathway coding regions in the desired host cell are numerous and familiar to those skilled in the art. Promoters capable of driving these genetic elements include, but are not limited to, CYC1, HIS3, GAL1, GAL10, ADH1, PGK, PHO5, GAPDH, ADC1, TRP1, URA3, LEU2, ENO, TPI, CUP1, FBA, GPD, and GPM (useful for expression in *Saccharomyces*); AOX1 (useful for expression in *Pichia*); and lac, ara, tet, trp, IPL, IPR, T7, tac, and trc (useful for expression in *Escherichia coli, Alcaligenes*, and *Pseudomonas*); the amy, apr, npr promoters and various phage promoters useful for expression in *Bacillus subtilis, Bacillus licheniformis*, and *Paenibacillus macerans*; nisA (useful for expression Gram-positive bacteria, Eichenbaum et al. *Appl. Environ. Microbiol.* 64(8):2763-2769 (1998)); and the synthetic P11 promoter (useful for expression in *Lactobacillus plantarum*, Rud et al., *Microbiology* 152:1011-1019 (2006)). Termination control regions, if present, may also be derived from various genes native to the preferred hosts.

In some embodiments, the cell is transformed with a first expression vector comprising:

- the polynucleotide encoding the first fucosyltransferase polypeptide,
- the polynucleotide encoding the nucleotide sugar pyrophosphorylase polypeptide,
- the polynucleotide encoding the lactose transporter polypeptide, and
- the polynucleotide encoding the L-fucose transporter polypeptide.

In some embodiments, the polynucleotide encoding the first fucosyltransferase polypeptide (e.g., WbgL) and the polynucleotide encoding the nucleotide sugar pyrophosphorylase polypeptide (e.g., Fkp) are operably linked to a first inducible promoter. In some embodiments, the first inducible promoter is a $P_{L1acO1}$ promoter.

In some embodiments, the polynucleotide encoding the second fucosyltransferase polypeptide (e.g., Hp3/4FT) is operably linked to a second inducible promoter. In some embodiments, the second inducible promoter is a $P_{LtetO1}$ promoter.

In some embodiments, the polynucleotide encoding the lactose transporter polypeptide and the polynucleotide encoding the L-fucose transporter polypeptide are operably linked to a constitutive promoter.

In some embodiments, the cell is modified to eliminate or reduce expression of an L-fucose mutarotase and/or a β-galactosidase. In some embodiments, the L-fucose mutarotase is an *E. coli* fucU, as set forth in SEQ ID NO:6, or a polypeptide having at least 70% identity thereto. In some embodiments, the β-galactosidase is an *E. coli* LacZ; as set forth in SEQ ID NO:6, or a polypeptide having at least 70% identity thereto. Knockout of L-fucose mutarotases and β-galactosidases can be conducted as described in more detail below. Other CRISPR/Cas9-based strategies, e.g., as described by Zhao et al. (*Microb Cell Fact* 2016, 15: 205) or König et al (*Bio Protoc.* 2018, 8(2): e2688), may be employed, as well as methods employing phage λ Red recombinase and/or FLP recombinase (see, Datsenko and Wanner. *PNAS,* 2000, 97 (12): 6640-6645; Baba, et al. *Molecular Systems Biology* 2006, 2:2006.0008)

II. PRODUCTION OF OLIGOSACCHARIDES

Also provided herein are methods for producing oligosaccharide products. In some embodiments, the oligosaccharide product includes two or more fucose moieties, and the method comprising culturing a recombinant cell as described herein in a cell culture medium comprising L-fucose, an oligosaccharide acceptor, and a carbon source. The cell is cultured under conditions in which a nucleotide sugar pyrophosphorylase polypeptide, a first fucosyltransferase polypeptide, a second fucosyltransferase polypeptide, a lactose transporter polypeptide, and/or an L-fucose transporter polypeptide are expressed and the oligosaccharide acceptor is converted to a fucosylated oligosaccharide.

In some embodiments, the acceptor is selected from the group consisting of lactose, lacto-N-tetraose (LNT), lacto-N-neotetraose (LNnT); lacto-N-hexaose (LNH); lacto-N-neohexaose (LNnH); para-lacto-N-hexaose (pLNH); and para-lacto-N-octaose (pLNO). Oligosaccharide products include, but are not limited to lactodifucotetraose (LDFT), difucosyl lacto-N-tetraose (DF-LNT), trifucosyl lacto-N-tetraose (TriF-LNT), trifucosyl para-lacto-N-hexaose (TriF-pLNH), and trifucosyl para-lacto-N-octaose (Tetra-F-pLNO)

In some embodiments, the oligosaccharide acceptor is lactose and the oligosaccharide product is lactodifucotetraose (LDFT).

Cell culture media generally contain a carbon source. Suitable substrates include, but are not limited to, monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide or methanol. In addition to one and two carbon substrates, methylotrophic organisms are also known to utilize a number of other carbon containing compounds such as methylamine, glucosamine, and a variety of amino acids for metabolic activity. For example, methylotrophic yeast are known to utilize the carbon from methylamine to form trehalose or glycerol. In some embodiments, the carbon source comprises glucose, glycerol, or a combination thereof.

In addition to an appropriate carbon source, fermentation media will typically contain suitable minerals, salts, cofactors, buffers and other components, known to those skilled in the art, suitable for the growth of the cultures and promotion of the enzymatic pathway for production of the desired oligosaccharide.

Typically, recombinant host cells are grown at a temperature in the range of about 20° C. to about 40° C. in an appropriate medium such as Luria Bertani (LB) broth, Sabouraud Dextrose (SD) broth or Yeast medium (YM) broth. Other defined or synthetic growth media may also be used, and the appropriate medium for growth of the particular microorganism will be known by one skilled in the art of microbiology or fermentation science. The use of agents known to modulate catabolite repression directly or indirectly, e.g., cyclic adenosine 2':3'-monophosphate, may also be incorporated into the fermentation medium.

Suitable pH ranges for the fermentation are between pH 5.0 to pH 9.0, where pH 6.0 to pH 8.0 is preferred as the initial condition. Oligosaccharide production may be conducted under aerobic or anaerobic conditions, including microaerobic conditions.

In some embodiments, expression of the nucleotide sugar pyrophosphorylase polypeptide and the first fucosyltransferase polypeptide is induced at a level corresponding to 30-40% of maximum level (e.g., with isopropyl β-D-1-thiogalactopyranoside in an amount around 50 μM). In some embodiments, expression of the second fucosyltransferase polypeptide is induced at a maximum level (e.g., with anhydrotetracycline at around 100 ng/mL).

The terms "about" and "around," as used herein to modify a numerical value, indicate a close range surrounding that explicit value. If "X" were the value, "about X" or "around X" would indicate a value from 0.8 X to 1.2 X, preferably a value from 0.9 X to 1.1 X, and, more preferably, a value from 0.95 X to 1.05 X. Any reference to "about X" or "around X" specifically indicates at least the values X, 0.9 X, 0.91 X, 0.92 X, 0.93 X, 0.94 X, 0.95 X, 0.96 X, 0.97 X, 0.98 X, 0.99 X, 1.01 X, 1.02 X, 1.03 X, 1.04 X, 1.05 X, 1.06 X, 1.07 X, 1.08 X, 1.09 X, and 1.10 X. Thus, "about X" and "around X" are intended to teach and provide written description support for a claim limitation of, e.g., "0.98 X."

The amount of oligosaccharide produced in the cell culture medium can be determined using a number of methods known in the art, for example, high performance liquid chromatography (HPLC) or thin-layer chromatography (TLC).

Oligosaccharides may be produced in a batch fashion or continuous fashion. A classical batch fermentation is a closed system where the composition of the medium is set at the beginning of the fermentation and not subject to artificial alterations during the fermentation. Within batch cultures, cells may moderate through a static lag phase to a high growth log phase and finally to a stationary phase where growth rate is diminished or halted. If untreated, cells in the stationary phase will eventually die. Cells in log phase generally are responsible for the bulk of production of end product or intermediate. A variation on the standard batch system is the fed-batch system. Fed-batch fermentation processes typically include incremental addition of an oligosaccharide acceptor or other substrate as the fermentation progresses.

Continuous fermentation typically involves an open system where a defined fermentation medium is added continuously to a bioreactor and an equal amount of conditioned media is removed simultaneously for processing. Continuous fermentation generally maintains the cultures at a constant high density where cells are primarily in log phase growth. Continuous fermentation allows for the modulation of one factor or any number of factors that affect cell growth or end product concentration. For example, a limiting nutrient such as the carbon source may be maintained at a fixed rate while all other parameters may be allowed to vary. In other systems a number of factors affecting growth can be altered continuously while the cell concentration, measured by media turbidity, is kept constant. Batch, fed-batch, and continuous fermentation systems are described, for example, by Bull et al. (Eds.) (*Manual of Industrial Microbiology and Biotechnology, Third Edition* (2010) ASM Press, Washington DC.) which is incorporated herein by reference.

III. EXAMPLES

Methods

Reagents

All enzymes involved in the molecular cloning experiments were purchased from New England Biolabs (NEB). All synthetic oligonucleotides were synthesized by Integrated DNA Technologies. Sanger sequencing was provided by Genewiz. D-Lactose was purchased from Sigma-Aldrich. L-Fucose was purchased from V-Labs, Inc. An analytical standard of 2'-FL was purchased from Carbosynth.

For synthesizing 3-FL, 8 mg lactose, L-fucose (1.3 equiv.), adenosine 5'-triphosphate (ATP, 1.3 equiv.), and guanidine 5'-triphosphate (GTP, 1.3 equiv.) were dissolved in 2.3 mL of 100 mM Tris-HCl buffer (pH 7.5) containing 20 mM $MgCl_2$, 0.35 mg *Bacteroides fragilis* bifunctional L-fucokinase/GDP-L-fucose pyrophosphorylase (BfFKP) (Yi et al., 2009), 0.15 mg *Pasteurella multocida* inorganic pyrophosphatase (PmPpA) (Yu et al., 2010), and 0.3 mg Hp3/4FT. The reaction mixture was incubated at 30° C. at 100 rpm for 16 h. The product formation was monitored by liquid chromatography-mass spectrometry (LCMS) (Shimadzu). When all lactose was converted to 3'-FL, the reaction was stopped by adding an equivalent volume of ice-cold ethanol. The mixture was kept at 4° C. for 30 min then centrifuged at 6,900 g for 30 min. The precipitates were removed and the supernatant was concentrated with a rotary evaporator and then passed through a Dowex® 1×8 ion exchange column. The partially purified product was obtained by elution with water. The eluate was concentrated, passed through a Bio-Gel P-2 gel filtration column, and eluted with water. The fractions containing the pure 3-FT product were collected and lyophilized.

To synthesize the LDFT standard, 8 mg lactose, L-fucose (1.2 equiv.), ATP (1.2 equiv.), and GTP (1.2 equiv.) were dissolved in 2.3 mL of 100 mM Tris-HCl buffer (pH 7.5) containing 20 mM $MgCl_2$, 0.3 mg BfFKP, 0.1 mg PmPpA, and 0.2 mg *Helicobacter mustelae* α1-2-fucosyltransferase (Hm2FT) (Ye et al., 2019). The reaction mixture was incubated at 30° C. at 100 rpm for 16 h. The product formation was monitored by LCMS. When all lactose was converted to 2'-FL, the reaction mixture was concentrated and applied to the next fucosylation step without purification. In the second step, the reaction mixture containing 10 mM 2'-FL formed from the previous step, L-fucose (1.2 equiv.), ATP (1.2 equiv.), and GTP (1.2 equiv.) in 2.3 mL of 100 mM Tris-HCl buffer (pH 7.5) containing 20 mM $MgCl_2$, 0.35 mg BfFKP, 0.15 mg PmPpA, and 0.3 mg Hp3/4FT. The reaction mixture was incubated at 30° C. at 100 rpm for 16 h. When all 2'-FL was converted to LDFT as monitored by LCMS, the reaction was stopped by adding an equal volume of ice-cold ethanol. The mixture was kept at 4° C. for 30 min and then centrifuged at 6,900 g for 30 min. The precipitates were removed and the supernatant was concentrated with a rotary evaporator and then passed through a Dowex® 1×8 ion exchange column. The partially purified product was obtained by elution with water. The eluate was concentrated, passed through a Bio-Gel P-2 gel filtration column, and eluted with water. The fractions containing the pure LDFT product were collected and lyophilized.

Strains and Plasmids

All strains used in this study are listed in Tables 1 and 3. All plasmids and primers are listed on Tables 4 and 5. Gene deletions and integrations were constructed using CRISPR-Cas9-mediated homologous recombination (Jiang et al., 2015). Linear DNA repair fragments for gene deletions were constructed by PCR assembly or amplification from genomic DNA using primers listed in Tables 4 and 6. The linear DNA repair fragment for ss9::$P_{lacUV5}$:T7rnap was PCR amplified from repair plasmid pAL1856 constructed from pSS9 template (Addgene plasmid #71655) (Bassalo et al., 2016) listed in Tables 3 & 6. All genomic modifications were PCR and sequence verified.

TABLE 1

Strain list

| Strain no. | *E. coli* strain | Plasmid | Key Genotype |
|---|---|---|---|
| 1 | AL3535 | | As BL21 Star (DE3), but ΔlacZ |
| 2 | AL3535 | pAL1779/pAL1817 | ΔlacZ, $P_{T7}$:fkp-wbgL, $P_{T7}$:Hp3/4ft |
| 3 | BL21 Star (DE3) | pAL1834 | $P_{T7}$:sfgfp |
| 4 | AL3535 | pAL1834 | ΔlacZ, $P_{T7}$: sfgfp |
| 5 | AL3600 | | As AL62, but ss9::PlacUV5:T7rnap |
| 6 | AL3601 | | As AL1050, but ss9::PlacUV5:T7rnap |
| 7 | AL3600 | pAL1834 | $P_{T7}$:sfgfp |
| 8 | AL3601 | pAL1834 | $P_{T7}$:sfgfp |
| 9 | AL3606 | | As Strain 6, but ΔfucU |
| 10 | AL3659 | | As Strain 9, but ΔlacZ |
| 11 | AL3659 | pAL1779/pAL1817 | ΔfucU, ΔlacZ, $P_{T7}$:fkp-wbgL |
| 12 | AL3659 | pAL1834 | ΔfucU, ΔlacZ, $P_{T7}$:sfgfp |
| 13 | AL3585 | | As AL1050, but ΔfucU |
| 14 | AL3664 | | As Strain 13, but ΔlacZ |
| 15 | AL3732 | | As Strain 14, but ss9::$P_{lacUV5}$:T7rnap |
| 16 | AL3732 | pAL1834 | ΔfucU, ΔlacZ, ss9::$P_{lacUV5}$:T7rnap, $P_{T7}$:sfgfp |
| 17 | AL1050 | pAL421 | $P_{LlacO1}$:sfgfp |
| 18 | AL3664 | pAL421 | ΔfucU, ΔlacZ, $P_{LlacO1}$:sfgfp |
| 19 | AL3732 | pAL421 | ΔfucU, ΔlacZ, ss9::$P_{lacUV5}$:T7rnap, $P_{LlacO1}$:sfgfp |
| 20 | AL1050 | pAL2054 | $P_{lacUV5}$:sfgfp |
| 21 | AL3585 | pAL2054 | ΔfucU, $P_{lacUV5}$:sfgfp |
| 22 | AL3664 | pAL2054 | ΔfucU, ΔlacZ, $P_{lacUV5}$:sfgfp |
| 23 | AL3664 | pAL1759/pAL1760 | ΔfucU, ΔlacZ, $P_{LlacO1}$:fkp-wbgL, $P_{LtetO1}$:Hp3/4ft |
| 24 | AL3664 | pAL2027/pAL1760 | ΔfucU, ΔlacZ, $P_{LlacO1}$:fkp-wbgL, BBa_K1824896:lacY, $P_{LtetO1}$:Hp3/4ft |
| 25 | AL3664 | pAL2028/pAL1760 | ΔfucU, ΔlacZ, $P_{LlacO1}$:fkp-wbgL, BBa_K1824896:fucP, $P_{LtetO1}$:Hp3/4ft |
| 26 | AL3664 | pAL2029/pAL1760 | ΔfucU, ΔlacZ, $P_{LlacO1}$:fkp-wbgL, BBa_K1824896:lacY-fucP, $P_{LtetO1}$:Hp3/4ft |
| 27 | AL3664 | pAL2059/pAL1760 | ΔfucU, ΔlacZ, $P_{LlacO1}$:fkp, BBa_K1824896:lacY-fucP, $P_{LtetO1}$:Hp3/4ft |

TABLE 2

Plasmid list

| Plasmid | Genotype | Reference |
|---|---|---|
| pAL421 | $P_{LlacO1}$:sfgfp; ColE1; $amp^r$ | This study |
| pAL1759 | $P_{LlacO1}$:fkp-wbgL; ColE1; $amp^r$ | This study |
| pAL1760 | $P_{LtetO1}$:Hp3/4ft; ColA; $kan^r$ | This study |
| pAL1779 | $P_{T7}$: fkp-wbgL; pBR322; $amp^r$ | This study |
| pAL1817 | $P_{T7}$:Hp3/4ft; ColA; $kan^r$ | This study |
| pAL1834 | $P_{T7}$:sfgfp; pBR322; $amp^r$ | This study |
| pAL2027 | BBa_K1824896:lacY; $P_{LlacO1}$:fkp-wbgL; pBR322; $amp^r$ | This study |

TABLE 2-continued

Plasmid list

| Plasmid | Genotype | Reference |
|---|---|---|
| pAL2028 | BBa_K1824896:fucP; $P_{LlacO1}$:fkp-wbgL pBR322; $amp^r$ | This study |
| pAL2029 | BBa_K1824896:lacY-fucP; $P_{LlacO1}$:fkp-wbgL; pBR322; $amp^r$ | This study |
| pAL2054 | $P_{lacUV5}$:sfgfp; ColE1; $amp^r$ | This study |
| pAL2059 | BBa_K1824896:lacY-fucP; $P_{LlacO1}$:fkp; pBR322; $amp^r$ | This study |

Other plasmids information is in Table 4.

TABLE 3

Strains used in this study

| Strain | Genotype | Source |
|---|---|---|
| XL-1 Blue | recA1 endA1 gyrA96 thi-1 hsdR17 supE44 relA1 lac [F' proAB lacIq ZΔM15 Tn10 ($tet^r$)] | Agilent |
| BL21 Star (DE3) (AL15) | $F^-$ ompT $hsdS_B$ ($r_B^-$, $m_B^-$) gal dcm rne131 (DE3) | ThermoFisher |
| BW25113 Z1 (AL62) | $lacI^+ rrnB_{T14}$ $\Delta lacZ_{WJ16}$ hsdR514 $\Delta araBAD_{AH33}$ $\Delta rhaBAD_{LD78}$ rph-1 Δ(araB-D)567 Δ(rhaD-B)568 ΔlacZ4787(::rrnB-3) hsdR514 rph-1 attB::$lacI^q$ tetR $spec^r$ | This study |
| MG1655 Z1 (AL1050) | F– lambda- ilvG- rfb-50 rph-1 attB::$lacI^q$ tetR $spec^r$ | (Yoneda et al. 2014) |
| AL3271 | As BW25113, but F' [proAB lacIq ZΔM15 Tn10 ($tet^r$)] ΔfucU | This study |
| AL3535 | As BL21 Star (DE3), but ΔlacZ | This study |
| AL3585 | As AL1050, but ΔfucU | This study |
| AL3600 | As AL62, but ss9::$P_{lacUV5}$:T7rnap | This study |
| AL3601 | As AL1050, but ss9::$P_{lacUV5}$:T7rnap | This study |

TABLE 3-continued

| Strains used in this study | | |
|---|---|---|
| Strain | Genotype | Source |
| AL3606 | As AL3601, but ΔfucU | This study |
| AL3659 | As AL3606, but ΔlacZ | This study |
| AL3664 | As AL3585, but ΔlacZ | This study |
| AL3732 | As AL3664, but ss9::$P_{lacUV5}$:T7rnap | This study |

TABLE 4

| Plasmids used in this study | | |
|---|---|---|
| Plasmid | Genotype | Source |
| pCas | $P_{cas}$:cas9 $P_{araB}$:Red lacI$^{q}$ $P_{trc}$:sgRNA pMB1 repA101(Ts) kan$^{r}$ | Addgene #62225 (Jiang et al., 2015) |
| pTargetF | sgRNA-pmB1 pMB1 spec$^{r}$ | Addgene #62226 (Jiang et al., 2015) |
| pss9 integration template | HR1$^{\#}$-$P_{T7A1}$:gfpUV-HR2$^{\wedge}$ pBR322 tet$^{r}$ | Addgene #71655 (Bassalo et al., 2016) |
| pAL421 | $P_{LlacO1}$:sfgfp ColE1 amp$^{r}$ | This study |
| pAL631 | $P_{LlacO1}$:sfgfp ColE1 kan$^{r}$ | This study |
| pAL1023 | $P_{LtetO1}$ ColA kan$^{r}$ | This study |
| pAL1354 | $P_{LlacO1}$ ColE1 amp$^{r}$ | This study |
| pAL1687 | $P_{T7}$:fkp pBR322 amp$^{r}$ | This study |
| pAL1688 | $P_{T7}$:wbgL pBR322 amp$^{r}$ | This study |
| pAL1689 | $P_{T7}$:Hp3/4ft pBR322 amp$^{r}$ | This study |
| pAL1759 | $P_{LlacO1}$:fkp-wbgL ColE1 amp$^{r}$ | This study |
| pAL1760 | $P_{LtetO1}$:Hp3/4ft ColA kan$^{r}$ | This study |
| pAL1762 | sgRNA-ss9 pMB1 spec$^{r}$ | This study |
| pAL1779 | $P_{T7}$:fkp-wbgL pBR322 amp$^{r}$ | This study |
| pAL1817 | $P_{T7}$:Hp3/4ft ColA kan$^{r}$ | This study |
| pAL1783 | HR1$^{\#}$-$P_{T7A1}$:gfpUV-HR2$^{\wedge}$ pBR322 amp$^{r}$ | This study |
| pAL1834 | $P_{T7}$:sfgfp pBR322 amp$^{r}$ | This study |
| pAL1845 | ΔlacZ HR1$^{\#}$-HR2$^{\wedge}$ ColE1 amp$^{r}$ | This study |
| pAL1846 | sgRNA-lacZ pMB1 spec$^{r}$ | This study |
| pAL1851 | sgRNA-lacZ pMB1 amp$^{r}$ | This study |
| pAL1853 | sgRNA-ss9 pMB1 amp$^{r}$ | This study |
| pAL1854 | $P_{lacUV5}$:lacZα-T7rnap ColE1 amp$^{r}$ | This study |
| pAL1855 | $P_{lacUV5}$:T7rnap ColE1 amp$^{r}$ | This study |
| pAL1856 | HR1-$P_{lacUV5}$:T7rnap-HR2 pBR322 amp$^{r}$ | This study |
| pAL1864 | sgRNA-fucU pMB1 amp$^{r}$ | This study |
| pAL2026 | BBa_K1824896*, $P_{L}$lacO1:fkp-wbgL colE1 amp$^{r}$ | This study |
| pAL2027 | BBa_K1824896*:lacY, $P_{LlacO1}$:fkp-wbgL ColE1 amp$^{r}$ | This study |
| pAL2028 | BBa_K1824896*:fucP, $P_{LlacO1}$:fkp-wbgL ColE1 amp$^{r}$ | This study |
| pAL2029 | BBa_K1824896*:lacY-fucP, $P_{LlacO1}$:fkp-wbgL ColE1 amp$^{r}$ | This study |
| pAL2054 | $P_{lacUV5}$:sfgfp ColE1 amp$^{r}$ | This study |
| pAL2059 | BBa_K1824896*:lacY, $P_{LlacO1}$:fkp ColE1 amp$^{r}$ | This study |

[#]upstream homologous region,
^downstream homologous region,
*iGEM part #: BBa_K1824896

TABLE 5

| Oligonucleotides used in this study | | | | |
|---|---|---|---|---|
| SEQ ID NO | Name | Sequence 5'→3' | Plasmid(s) produced | Used for PCR and/or sequencing |
| 27 | AZ52 | GTCTTGTCGATCAGGATGATC | | pAL1817 |
| 28 | AZ55 | CGAGCCCGTATAAACTGAAAGC | | pAL1760 |
| 29 | AZ56 | CTAGGTCTAGGGCGGCGGATTTG | | pAL1759, pAL1845, pAL1854, pAL2054 |

TABLE 5-continued

Oligonucleotides used in this study

| SEQ ID NO | Name | Sequence 5'→3' | Plasmid(s) produced | Used for PCR and/or sequencing |
|---|---|---|---|---|
| 30 | AZ57 | CGTAAGATACTGACAGAAAACGC | | pAL1759, pAL1779, pAL2059 |
| 31 | AZ60 | GGAGGAAGGAAAGAATATCTGG | | pAL1759 |
| 32 | AZ61 | GTGACTTTATTGGCTGCTATTCC | | pAL1759 |
| 33 | AZ64 | CAAATAGGGGTTCCGCGCACAT | | pAL1759, pAL1779, pAL1854, pAL1855 |
| 34 | AZ65 | GATATGACTGTTCTCGATCCA | | pAL1759 |
| 35 | AZ82 | CCCTGGCAAATGTTGATTGA | | fucU upstream |
| 36 | AZ83 | CAGGCTGTTACCAAAGAAGT | | fucU downstream |
| 37 | AZ105 | CGGCCTTATTGTCTCTCTGC | | pAL1817 |
| 38 | AZ154 | CCTAGGTCTAGGGCGGCGGATTTG | | pAL2059 |
| 39 | AZ155 | CATTATAACATTCTTCAAGCAGCC | | pAL2026, pAL2059 |
| 40 | AZ224 | AATTCATTAAAGAGGAGAAAAGATATA CCATGGGCAGCAG | pAL1759 | |
| 41 | AZ225 | CATATGTATATCTCCTTCTTTTATGATCG TGATACTTGGAATC | pAL1759 | |
| 42 | AZ226 | AAGAAGGAGATATACATATGAGCATTA TTCG | pAL1759 | |
| 43 | AZ227 | TTAGCAGCCGGATCTCAGTG | pAL1759 | |
| 44 | AZ228 | CACTGAGATCCGGCTGCTAAGGTACCTA ATCTAGAGGCATC | pAL1759 | |
| 45 | AZ229 | TTTCTCCTCTTTAATGAATTCGGTCAGTG CGTCC | pAL1759 | |
| 46 | AZ230 | AATTCATTAAAGAGGAGAAACATATGTT CCAACCGCTGCTG | pAL1760 | |
| 47 | AZ231 | CTCTAGAGTCATTAGGTACCGCTTTGTT AGCAGCCGGATC | pAL1760 | |
| 48 | AZ233 | TTTCTCCTCTTTAATGAATTCGG | pAL1760 | |
| 49 | AZ259 | GAATTCGGTCAGTGCGTCCTGCTG | | pAL2027, pAL2028 |
| 50 | AZ274 | AAGGATCCGGCTGCTAACAAAAGGAGA TATACATATGAGC | pAL1779 | |
| 51 | AZ275 | ACTCAGCTTCCTTTCGGGCTAGCAGCCG GATCTCAGTG | pAL1779 | |
| 52 | AZ276 | AGCCCGAAAGGAAGCTGAGTTGGCTGC TG | pAL1779 | |
| 53 | AZ277 | TTGTTAGCAGCCGGATCCTTATGATCGT GATACTTG | pAL1779 | |
| 54 | AZ293 | ATGATTGAACAAGATGGATTGCACGC | pAL1817 | pAL1817 |
| 55 | AZ294 | AGGAGAGCGTTCACCGACAAAACGCCA GCAACGCGG | pAL1817 | |
| 56 | AZ295 | AATCCATCTTGTTCAATCATACTCTTCCT TTTTCAATATTATTGAAGCATTTATCAG GG | pAL1817 | |
| 57 | AZ307 | CACTTTACTACCCACGCCGC | | BL21 Star (DE3) attB locus |

TABLE 5-continued

Oligonucleotides used in this study

| SEQ ID NO | Name | Sequence 5'→3' | Plasmid(s) produced | Used for PCR and/or sequencing |
|---|---|---|---|---|
| 58 | AZ308 | GACTGGCAGCAACAGGTGGC | | BL21 Star (DE3) attB locus |
| 59 | AZ309 | GTTGAGCTACAGGCGGTCAG | | ss9::$P_{lacUV5}$:T7rnap |
| 60 | AZ310 | ATTTACTAACTGGAAGAGGC | | pAL1854, pAL1856, ss9::$P_{lacuV5}$:T7rnap |
| 61 | AZ311 | CATTGAGTCAACCGGAATGG | | pAL1854, pAL1856, ss9::$_{PlacuV5}$:T7rnap |
| 62 | AZ312 | AAACCAATCGGTAAGGAAGG | | pAL1854, pAL1856, ss9::$P_{lacUV5}$:T7rnap |
| 63 | AZ313 | TTTTACCGTTCACGCGCTGG | | ss9::$P_{lacUV5}$:T7rnap |
| 64 | AZ336 | TGGTGCCGCGCGGCAGCCATATGGGTCA TCACCACCATCATC | pAL1834 | |
| 65 | AZ337 | TTCGGGCTAGCAGCCGGATCTTATTTGT ACAGTTCGTCCATGCCG | pAL1834 | |
| 66 | AZ338 | GATCCGGCTGCTAGCCCGAAAGGAAGC TGAGTTGGCTG | pAL1834 | |
| 67 | AZ339 | ATGGCTGCCGCGCGGCACCAG | pAL1834 | |
| 68 | AZ340 | AATGCGCGCCATTACCGAGTCCG | pAL1845 | lacZ upstream |
| 69 | AZ341 | AGCTGTTTCCTGTGTGAAATTGTTATCC GC | pAL1845 | |
| 70 | AZ342 | ATTTCACACAGGAAACAGCTTAATAACC GGGCAGGCCATGTCTG | pAL1845 | |
| 71 | AZ343 | ACTTTCTCAATAAATGCCTCTACTGCTG GCGCACC | pAL1845 | lacZ downstream |
| 72 | AZ344 | GAGGCATTTATTGAGAAAGTTAATCTAG AGGCATCAAATAAAACGAAAGGCTCAG TCG | pAL1845 | |
| 73 | AZ345 | ACTCGGTAATGGCGCGCATTGGTCAGTG CGTCCTGCTGATG | pAL1845 | |
| 74 | AZ347 | GCCGACACCAGTTTTAGAGCTAGAAATA G | pAL1846 | |
| 75 | AZ348 | TCCGCCGCCTACTAGTATTATACCTAGG ACTGAG | pAL1846 | |
| 76 | AZ359 | CAGCGGTGGAGTGCAATGTCATGAGTAT TCAACATTTCCG | pAL1851 | |
| 77 | AZ360 | ATCGACTGGCGAGCGGCATCTTACCAAT GCTTAATCAGTG | pAL1851 | |
| 78 | AZ361 | GATGCCGCTCGCCAGTCGATTGGC | pAL1851 | |
| 79 | AZ362 | GACATTGCACTCCACCGCTGATGAC | pAL1851 | |
| 80 | AZ364 | TCCGGATTTACTAACTGGAAGAGGCACT AAATG | pAL1855 | |
| 81 | AZ365 | AGCTGTTTCCTGTGTGAAATTGTTATCC GCTC | pAL1855 | |
| 82 | AZ366 | CCTTTCGTCTTCACCTCGAGTCACTCATT AGGCACCCCAGGC | pAL1854 | |
| 83 | AZ367 | GGTACCTTAGCAGCCGGATCTTACGCGA ACGCGAAGTCCGAC | pAL1854 | |

TABLE 5-continued

| SEQ ID NO | Name | Sequence 5'→3' | Plasmid(s) produced | Used for PCR and/or sequencing |
|---|---|---|---|---|
| Oligonucleotides used in this study | | | | |
| 84 | AZ368 | GATCCGGCTGCTAAGGTACCTAATCTAG AGGC | pAL1854 | |
| 85 | AZ369 | CTCGAGGTGAAGACGAAAGGGCCT | pAL1854 | |
| 86 | AZ370 | AGTTGATATGTCAAACAGGTTCACTCAT TAGGCACCCCAGGC | pAL1856 | |
| 87 | AZ371 | CGGCGCTCAGTTGGAATTCAACAACAGA TAAAACGAAAGGCC | pAL1856 | |
| 88 | AZ372 | TGAATTCCAACTGAGCGCCGGTC | pAL1856 | |
| 89 | AZ373 | ACCTGTTTGACATATCAACTGCGCC | pAL1856 | |
| 90 | AZ384 | GTGATGATGGGTTTTAGAGCTAGAAATA GC | pAL1864 | |
| 91 | AZ385 | CAGCGGCGGTACTAGTATTATACCTAGG AC | pAL1864 | |
| 92 | AZ403 | ACTCTTCCTTTTTCAATATTATTGAAGCA TTTATCAGGG | | pAL2027, pAL2028, pAL2029, pAL2054, pAL2059 |
| 93 | AZ411 | CGCGCGGCACACTAGTATTATACCTAGG AC | | pAL2029 |
| 94 | AZ710 | GTGCCACCTGACGTCTAAGACTAGTACT CTAGTATTTCTCCTCTTTA | pAL2026 | pAL2026 |
| 95 | AZ711 | GCTACTAGAGTACTAGAGTACTAGAGAT TAAAGAGGAGAAATACTAGAGTACTAG TCTTA | pAL2026 | |
| 96 | AZ712 | TCTCTAGTACTCTAGTACTCTAGTAGCT AGCACTGTACCTAGGACTGAGCTAGCCG T | pAL2026 | |
| 97 | AZ713 | ACGCCTATTTTTATAGGTTAATGTCATG ATAATAATGGTTTTGACGGCTAGCTCAG TCC | pAL2026 | |
| 98 | AZ714 | TGACATTAACCTATAAAAATAGGCGTAT CACGAGGCCCTTTCGTCTTCACCTCGAG AAT | pAL2026 | |
| 99 | AZ715 | TTGTTATCCGCTCACAATGTCAATTGTTA TCCGCTCACAATTCTCGAGGTGAAGACG AA | pAL2026 | pAL2026 |
| 100 | AZ716 | CAATTGACATTGTGAGCGGATAACAAG | pAL2026 | |
| 101 | AZ717 | TCTTAGACGTCAGGTGGCACTTTTCG | pAL2026, pAL2027, pAL2028. pAL2029 | |
| 102 | AZ718 | GTGCCACCTGACGTCTAAGATTAAGCGA CTTCATTCACCTG | pAL2027 | |
| 103 | AZ719 | GAGAAATACTAGAGTACTAGATGTACTA TTTAAAAAACACAAACTTTTGGATG | pAL2027 | |
| 104 | AZ720 | CTAGTACTCTAGTATTTCTCCTCTTTAAT CTCTAGTAC | pAL2027, pAL2028 | |
| 105 | AZ721 | GTGCCACCTGACGTCTAAGATCAGTTAG TTGCCGTTTGAGAAC | pAL2028, pAL2029 | |
| 106 | AZ722 | GAGAAATACTAGAGTACTAGATGGGAA ACACATCAATACAAACGCAGAG | pAL2028 | |

TABLE 5-continued

Oligonucleotides used in this study

| SEQ ID NO | Name | Sequence 5'→3' | Plasmid(s) produced | Used for PCR and/or sequencing |
|---|---|---|---|---|
| 107 | AZ723 | GAAAGAGGGGACAAACTAGTATGGGAAACACATCAATACAAACG | pAL2029 | |
| 108 | AZ724 | TTGTCCCCTCTTTCTCTAGATTAAGCGACTTCATTCACCTGACG | pAL2029 | |
| 109 | AZ819 | CTAACTGGAAGAGGCACTAAATGGGTCATCACCACCATCATCACG | pAL2054 | |
| 110 | AZ820 | GGTACCTTAGCAGCCGGATCTTATTTGTACAGTTCGTCCATGCCG | pAL2054 | |
| 111 | AZ821 | GATCCGGCTGCTAAGGTACCTAATC | pAL2054 | |
| 112 | AZ822 | TTAGTGCCTCTTCCAGTTAGTAAATCCGG | pAL2054 | |
| 113 | AZ851 | CTGCTAAGGTACCTAATCTAGAGGCATC | pAL2059 | |
| 114 | AZ852 | CCGGATCTTATGATCGTGATACTTGGAATC | pAL2059 | |
| 115 | JO232 | GGTTCCGCGCACATTTCCC | | pAL1845 |
| 116 | MMM40 | GAGTCAGTGAGCGAGGAAGC | | pAL1846, pAL1851, pAL1864 |
| 117 | MMM131 | GCTTGGTTGAGAATACGCCG | | pAL1856, ss9 upstream |
| 118 | MMM132 | GCCTACGATTACGCATGGCTTG | | pAL1856, ss9 downstream |
| 119 | SD62 | GGCCCTTTCGTCTTCACCTCGAG | | pAL1760 |
| 120 | SL005 | AACGCAGTCAGGCACCGTGTATGAGTATTCAACATTTCCG | pAL1783 | pAL1783 |
| 121 | SL006 | GAGGTGCCGCCGGCTTCCATTTACCAATGCTTAATCAGTG | pAL1783 | pAL1783 |
| 122 | SL007 | ATGGAAGCCGGCGGCACCTC | pAL1783 | |
| 123 | SL008 | ACACGGTGCCTGACTGCGTTAGC | pAL1783 | |
| 124 | YT167 | TAATGACTCTAGAGGCATCAAATAA | pAL1760 | |
| 125 | YT054 | TTGTCGGTGAACGCTCTCCTG | pAL1817 | pAL1817 |
| 126 | YT400 | ATGGGTCATCACCACCATCATCA | | pAL1834 |
| 127 | YT430 | CCAGTAGTAGGTTGAGGCCGTTGAG | | pAL1834 |
| 128 | YT092 | CTACTCAGGAGAGCGTTCAC | | pAL1760 |
| 129 | YT101 | GCTTCCCAACCTTACCAGAG | | pAL1760 |
| 130 | YTC427 | CAAGCAGCAGATTACGCGCAG | | pAL1851 |

TABLE 6

Guide for CRISPR-Cas9-mediate gene deletions and insertions

| | pTargetF | | PCR Linear Repair Fragment | |
|---|---|---|---|---|
| Modification | Plasmid | 20 bp sgRNA sequence 5'→3' | Primers | Template |
| ΔfucU | pAL1864 | ACCGCCGCTGGTGATGATGG (SEQ ID NO: 131) | AZ82 (F), AZ83 (R) | AL3271 gDNA |

TABLE 6-continued

| Guide for CRISPR-Cas9-mediate gene deletions and insertions | | | | |
|---|---|---|---|---|
| | pTargetF | | PCR Linear Repair Fragment | |
| Modification | Plasmid | 20 bp sgRNA sequence 5'→3' | Primers | Template |
| ΔlacZ | pAL1851 | AGGCGGCGGAGCCGACACCA (SEQ ID NO: 132) | AZ340 (F), AZ343 (R) | pAL1845 |
| ss9::$P_{lacUV5}$:T7rnap | pAL1853 | TCTGGCGCAGTTGATATGTA (SEQ ID NO: 133) | MMM131 (F), MMM132 (R) | pAL1856 |

Plasmids for sfGFP fluorescence assays, LDFT production, and 3-FL production were constructed using sequence and ligation independent cloning (SLIC) (Li and Elledge, 2007). Plasmids encoding sgRNAs for CRISPR-Cas9-mediated homologous recombination were constructed with Q5 site-directed mutagenesis using a modified template pTargetF (Addgene plasmid #62226). Templates used for DNA amplification and cloning are listed in Table 7. All plasmids were verified by PCR and Sanger sequencing. Culture conditions Overnight cultures were grown at 37° C., 250 rpm, in 3 mL of Luria-Bertani (LB) media with appropriate antibiotics. Antibiotic concentrations were as follows: spectinomycin (50 μg/mL), ampicillin (200 μg/mL), and kanamycin (50 μg/mL). Growth assays were carried out in M9 minimal medium (33.7 mM $Na_2HPO_4$, 22 mM $KH_2PO_4$, 8.6 mM NaCl, 9.4 mM $NH_4Cl$, 1 mM $MgSO_4$, 0.1 mM $CaCl_2$)) including 1000×A5 trace metal mix (2.86 g $H_3BO_3$, 1.81 g $MnCl_2 \cdot 4H_2O$, 0.079 g $CuSO_4 \cdot 5H_2O$, 49.4 mg $Co(NO_3)_2 \cdot 6H_2O$ per liter water). LDFT production was carried out in M9 minimal medium supplemented with 5 g/L yeast extract (M9P). Optical densities were measured at 600 nm ($OD_{600}$) with a Synergy H1 hybrid plate reader (BioTek Instruments, Inc.).

Growth Assays

Overnight cultures were inoculated at 1% in 3 mL of M9 minimal medium supplemented with 1 g/L D-lactose or 1 g/L L-fucose. Cultures were grown at 37° C., 250 rpm, for 24 h and $OD_{600}$ was measured.

Fluorescence Assays

Overnight cultures were inoculated at 1% in 3 mL of LB media and grown at 37° C., 250 rpm, until $OD_{600}$ reached 0.4-0.6. Cultures were respectively induced with isopropyl β-D-1-thiogalactopyranoside (IPTG, 1.0 mM) and grown at 37° C., 250 rpm, for 24 h.

TABLE 7

| Plasmid construction guide | | | | | | | |
|---|---|---|---|---|---|---|---|
| | PCR for Vector | | | PCR for Insert(s) | | | |
| Plasmid | Primer (F) | Primer (R) | Template | Primer (F) | Primer (R) | Template | Sequence of Interest |
| pAL1759 | AZ228 | AZ229 | pAL1354 | AZ224 | AZ225 | pAL1687 | fkp |
| | | | | AZ226 | AZ227 | pAL1688 | wbgL |
| pAL1760 | YT167 | AZ233 | pAL1023 | AZ230 | AZ231 | pAL1689 | Hp3/4ft |
| pAL1779 | AZ276 | AZ277 | pAL1687 | AZ274 | AZ275 | pAL1688 | wbgL |
| pAL1817 | AZ294 | AZ295 | pAL1689 | AZ293 | YT054 | pAL1023 | ColA-kan$^r$ |
| pAL1762* | MMM139 | MMM140 | pTargetF | | | | |
| pAL1783 | SL007 | SL008 | pss9 | SL005 | SL006 | pAL1354 | amp$^r$ |
| pAL1845 | AZ344 | AZ345 | pAL1354 | AZ340 | AZ341 | AL1050 gDNA | 400 bp upstream HR1 lacZ |
| | | | | AZ342 | AZ343 | AL1050 gDNA | 400 bp downstream HR2 lacZ |
| pAL1854 | AZ368 | AZ369 | pAL1759 | AZ366 | AZ367 | BL21 Star (DE3) gDNA | $P_{lacUV5}$:lacZ□ T7rnap |
| pAL1855* | AZ364 | AZ365 | pAL1854 | | | | |
| pAL1856 | AZ372 | AZ373 | pAL1783 | AZ370 | AZ371 | pAL1855 | $P_{lacUV5}$:T7rnap |
| pAL1846* | AZ347 | AZ348 | pTargetT | | | | |
| pAL1851 | AZ361 | AZ362 | pAL1846 | AZ359 | AZ360 | pAL1687 | amp$^r$ |
| pAL1853 | AZ361 | AZ362 | pAL1762 | AZ359 | AZ360 | pAL1687 | amp$^r$ |
| pAL1864* | AZ384 | AZ385 | pAL1851 | | | | |
| pAL1834 | AZ338 | AZ339 | pAL1687 | AZ336 | AZ337 | pAL421 | sfgfp |
| pAL2026 | AZ716 | AZ717 | pAL1759 | AZ710, AZ712, AZ714 | AZ711, AZ713, AZ715 | N/A | BBa_K1824896 |
| pAL2027 | AZ720 | AZ717 | pAL2026 | AZ718 | AZ719 | AL1050 gDNA | lacY |
| pAL2028 | AZ721 | AZ722 | pAL2026 | AZ718 | AZ719 | AL1050 gDNA | fucP |
| pAL2029 | AZ724 | AZ717 | pAL2027 | AZ721 | AZ723 | AL1050 gDNA | fucP |
| pAL2054 | AZ821 | AZ822 | pAL1855 | AZ819 | AZ820 | pAL631 | sfgfp |
| pAL2059* | AZ851 | AZ852 | pAL2029 | | | | |

*Q5-site directed mutagenesis (NEB).

Fluorescence emission was measured at 510 nm with a Synergy H1 hybrid plate reader (BioTek Instruments, Inc.).

LDFT Production

Overnight cultures were inoculated at 1% in 3 mL of M9P supplemented with 5 g/L glucose, 10 g/L glycerol, or 20 g/L glycerol. Cultures were grown at 37° C., 250 rpm, until $OD_{600}$ reached 0.4-0.6. Appropriate concentrations of lactose, L-fucose, IPTG, and anhydrotetracycline (aTc) were added and the cultures were grown at 30° C., 250 rpm, for 24 h. The produced LDFT was confirmed by high resolution electrospray ionization mass spectrometry using a Thermo Electron LTQ-Orbitrap Hybrid MS at the Mass Spectrometry Facility in the University of California, Davis.

HPLC Analysis

To measure glycerol, L-fucose, lactose, 2'-FL, 3-FL, and LDFT, cell culture supernatant was analyzed using HPLC (Shimadzu) equipped with a refractive index detector (RID) 10 A and a Luna Omega HILIC Sugar column (Phenomenex). The mobile phase consisted of 100% 70:30 HPLC-grade acetonitrile:MilliQ water was run at a flow rate of 1.0 mL/min for 12 min, with the column oven at 35° C. and RID cell temperature at 40° C.

To prepare samples for HPLC analysis, 125 μL of culture was collected and spun down at 17,000 g for 5 min. 15 μL of culture supernatant or compound standard in water was diluted with 45 μL of MilliQ water and 180 μL of acetonitrile. The mixture was vortexed and spun down at 17,000 g for 5 min. 40 μL of each sample was injected into the column for analysis.

Results

Pathway Design for LDFT Production in *E. coli*

HMO production does not naturally occur in *E. coli*, therefore the following three enzymes were employed for the production of LDFT: a bifunctional L-fucokinase/GDP-L-fucose pyrophosphorylase (Fkp) from *Bacteroides fragilis* (Yi et al., 2009), an α1-2-fucosyltransferase (WbgL) from *E. coli* 0126 (Engels and Elling, 2014; McArthur et al., 2019), and α1-3/4-fucosyltransferase (Hp3/4FT) from *Helicobacter pylori* UA948 (Rasko et al., 2000; Yu et al., 2017). Acceptor substrate specificity studies of both WbgL and Hp3/4FT have been reported (Engels and Elling, 2014; Ma et al., 2006; McArthur et al., 2019; Yu et al., 2017). WbgL exhibits high activity towards non-fucosylated acceptor substrates, such as lactose, N-acetyllactosamine (LacNAc), and lactulose, and no activity towards 3-FL. Hp3/4FT has been shown to be highly active towards LacNAc and 2'-fucosyl-LacNAc with low activity towards lactose. The acceptor preferences of the fucosyltransferases allow sequential fucosylation of lactose for the formation of LDFT in the presence of both fucosyltransferases. Fkp uses one ATP and GTP to convert L-fucose to GDP-fucose, which is taken as a donor substrate by WbgL to fucosylate lactose at the C2' position, forming the intermediate 2'-FL (FIG. 1). Due to its structural similarity to 2'-fucosyl-LacNAc, 2'-FL was hypothesized to be a suitable acceptor substrate for fucosylation by Hp3/4FT to produce LDFT, which is expected to be secreted to the supernatant by native membrane exporter SetA (Liu et al., 1999).

LDFT Production in *E. coli* B Strains

The relatively low soluble expression level of recombinant fucosyltransferases was of initial concern as a potential cause of bottlenecks for synthesizing fucosylated HMOs in microbial hosts (Nidetzky et al., 2018). In this study, the C-terminal 34-amino acid hydrophobic sequence of Hp3/4FT was truncated to increase its solubility (Yu et al., 2017). To increase the expression of fucosyltransferases, *E. coli* B strain BL21 Star (DE3) was selected as an LDFT production host. BL21 Star (DE3) is widely used for recombinant protein expression and is capable of high expression via the two-step IPTG-inducible T7 bacteriophage promoter (Rosano and Ceccarelli, 2014). The fkp and wbgL genes were cloned together into an expression vector under a T7-promoter ($P_{T7}$, pAL1779, Table 2) and the truncated Hp3/4 ft gene was cloned into a second expression vector under $P_{T7}$ (pAL1817, Table 2).

Figure 2A:
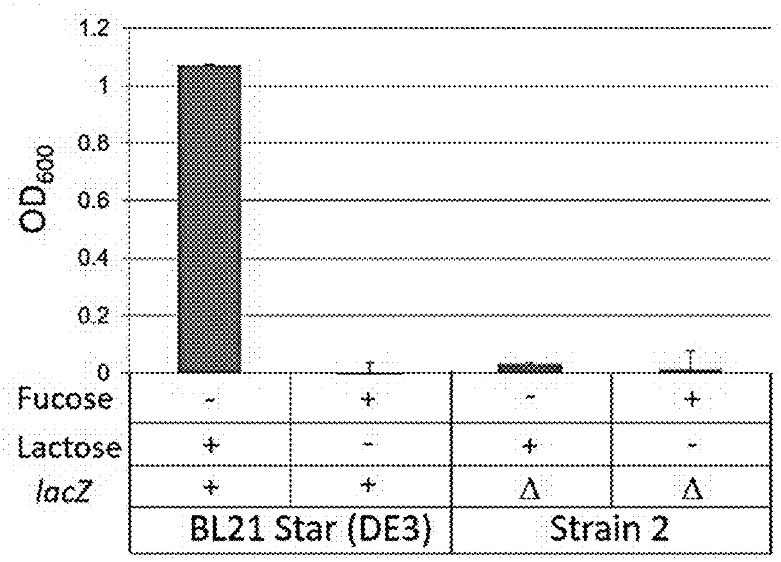
FIG. 2A shows cell growth and protein expression resulting from modifications in *E. coli* B-strains for LDFT production. Growth of BL21 Star (DE3) and ΔlacZ mutant (Strain 2, Table 1) in M9 minimal media with or without 1 g/L L-fucose or D-lactose.

Lactose and L-fucose were used as starting substrates for LDFT production, but *E. coli* is known to catabolize these two sugars for growth. It was hypothesized that minimizing assimilation of L-fucose and lactose for cellular growth would contribute to maximization of LDFT production. Therefore, the strain's ability to grow on these two carbon sources was evaluated to determine which carbon assimilating pathways to remove. Although the BL21 Star (DE3) encodes all genes involved in L-fucose degradation, the strain was not able to grow on L-fucose as the sole carbon source (FIG. 2A). The strain was able to grow on lactose as the sole carbon source (FIG. 2A). When the lacZ gene encoding for a β-galactosidase was deleted in the strain (Table 1: Strain 1), lactose did not enable growth anymore (FIG. 2).

Figure 2B:
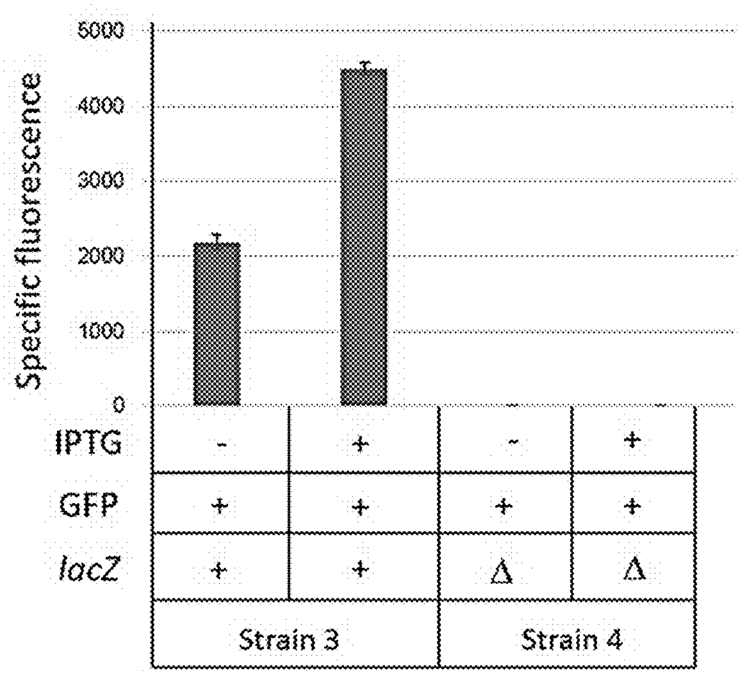
FIG. 2B shows expression of $P_{T7}$:sfgfp in BL21 Star (DE3) (Strain 3) and ΔlacZ mutant (Strain 4, Table 1) in LB-media. Cultures were induced with or without 1 mM IPTG, respectively. A indicates that the gene was removed from the genome. Error bars indicate s.d. (n=3 biological replicates).

The two plasmids containing the LDFT production pathway (pAL1779 and pAL1817, Tables 2 & 4) were introduced into Strain 1 to form Strain 2 (Table 1). To determine the best carbon source for growth and production, Strain 2 was grown in parallel with glucose, a common feedstock known for its catabolite repression towards lactose importation (Bruckner and Titgemeyer, 2002), and glycerol, an inexpensive feedstock that does not cause catabolite repression. Under both of these culturing conditions, Strain 2 did not produce LDFT nor its precursor, 2'-FL. To examine the expression from $P_{T7}$, the plasmid containing sfgfp under $P_{T7}$ (pAL1843, Table 2) was introduced into BL21 Star (DE3) and Strain 1 to form Strains 3 and 4, respectively (Table 1). Strain 3 produced a strong fluorescent signal after IPTG induction while Strain 4 did not produce fluorescence signal in either induction conditions, suggesting that T7 RNA polymerase expression was lacking (FIG. 2B). Sequencing of the attB integration locus in Strain 1 revealed an excision of the λDE3 lysogen containing $P_{lacUV5}$:lacZα-T7rnap. Several attempts were made to remove lacZ from BL21 Star (DE3) without off-target modifications to the λDE3 lysogen but resulted in failure.

Introduction of the T7 RNAP Gene into K-12 Derivative Strains

Figure 3A:
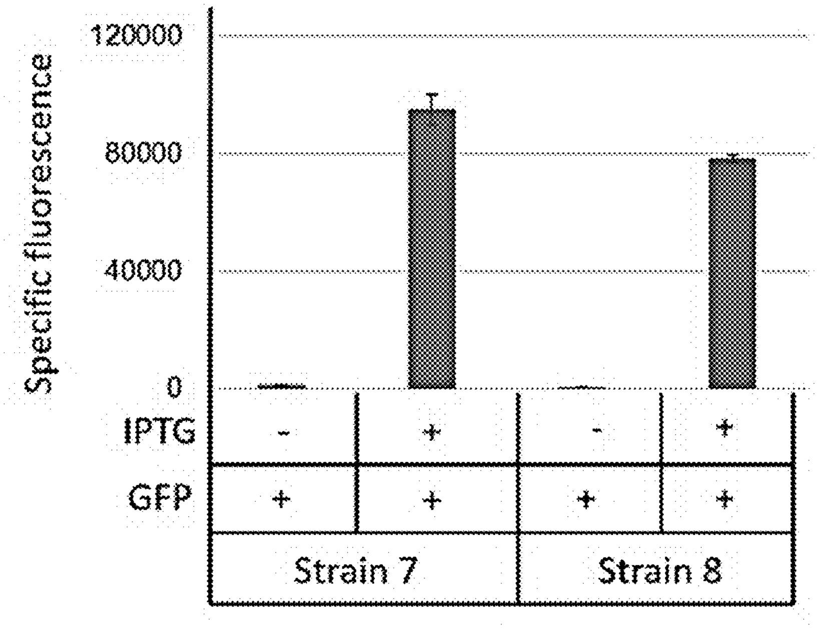
FIG. 3A shows cell growth and protein expression after installation of the T7 RNAP expression system into *E. coli* K-12-derivative strains. GFP fluorescence assay in K-12 derivative strains, BW25113 Z1 (Strain 7) and MG1655 Z1 (Strain 8, Table 1) with ss9::$P_{lacuv5}$:T7rnap. Cultures were induced with or without 1 mM IPTG at 37° C. for 24 h.
Figure 3B:
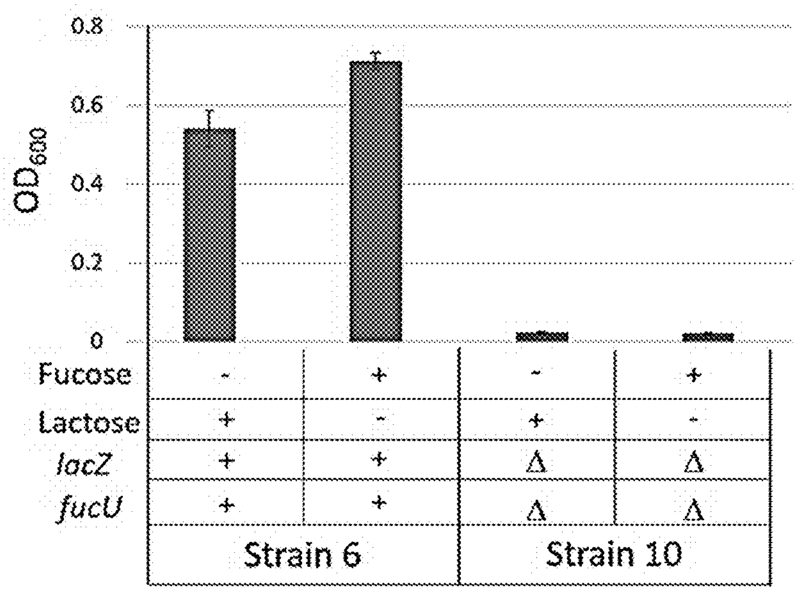
FIG. 3B shows a growth assay of MG1655 Z1 (Strain 6) and Strain 10 (Strain 6 with ΔfucU ΔlacZ, Table 1) in M9-minimal media with or without 1 g/L L-fucose or D-lactose at 37° C. for 24 h.

Due to difficulties in genetically modifying BL21 Star (DE3), $P_{lacUV5}$:T7rnap was integrated into the *E. coli* K-12 derivative strains, BW25113 Z1 and MG1655 Z1 (Table 3). The Z1 fragment containing $laci^q$, tetR, and $spec^r$ was integrated into the attB site of these strains. It has been shown that many regions in the *E. coli* genome are stable and high-efficiency integration sites for heterologous genes (Bassalo et al., 2016), therefore intergenic locus ss9 was chosen as the insertion site for $P_{lacUV5}$:T7rnap. The $P_{lacUV5}$:T7rnap cassette was integrated into ss9 of BW25113 Z1 and MG1655 Z1 to form Strains 5 and 6, respectively (Table 1).

pAL1834 containing $P_{T7}$:sfgfp was introduced into Strains 5 and 6 to form Strains 7 and 8, respectively (Table 1) to assess the repression and induction efficiencies of $P_{T7}$ through a fluorescence assay. Tight repression of GFP expression without IPTG was observed in Strains 7 and 8 (FIG. 3A). IPTG induction in Strains 7 and 8 increased GFP fluorescence 95-fold and 440-fold, respectively (FIG. 3A). Strain 6 was chosen as the base strain for further genetic modification due to its tighter repression and stronger inducibility of $P_{T7}$. The growth of Strain 6 on L-fucose and lactose was tested. Strain 6 was able to grow on L-fucose or lactose as a sole carbon source (FIG. 3B). To remove L-fucose and lactose assimilation, fucU encoding an L-fucose mutarotase and lacZ were deleted to form Strain 10 (Table 1). Strain 10 was not able to grow on L-fucose or lactose as a sole carbon source (FIG. 3B).

Figure 3C:
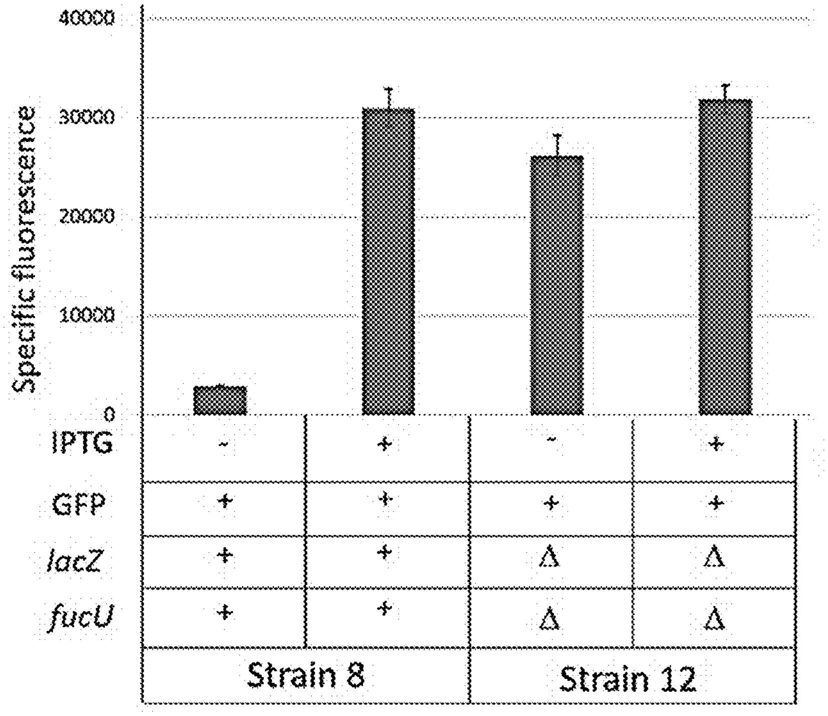
FIG. 3C shows a fluorescence assay to evaluate GFP expression from $P_{T7}$ in Strain 8 and Strain 12 (Strain 8 with ΔfucU ΔlacZ, Table 1). Cultures were grown in LB-media and induced with or without 1 mM IPTG at 37° C. for 24 h.

The LDFT production plasmids (pAL1779 and pAL1817, Table 2) were introduced into Strain 10 to form Strain 11 (Table 1). Strain 11 was grown to test LDFT production from lactose and L-fucose. Glucose or glycerol was used to maintain cellular growth. Under both conditions, LDFT was not produced in Strain 11. This prompted the examination of the T7 RNA polymerase expression system in Strain 10. pAL1834 containing $P_{T7}$:sfgfp was introduced into Strain 10 to form Strain 12 (Table 1). Strain 12 produced strong GFP fluorescence without IPTG induction, indicating the expression from $P_{T7}$ was leaky in Strain 12 (FIG. 3C). In Strain 10, a mutation in the promoter region of the $P_{lacUV5}$:T7rnap cassette was found. The deletion of lacZ in Strain 9 without incurring $P_{lacUV5}$ mutations was attempted several times, but the attempts were unsuccessful. Without wishing to be bound by any particular theory, it is believed that that the mutations in $P_{lacUV5}$ are correlated with the CRISPR-Cas9-mediated gene removal of lacZ due to the similarity of the lacZ promoter to $P_{lacUV5}$.

Figure 3D:
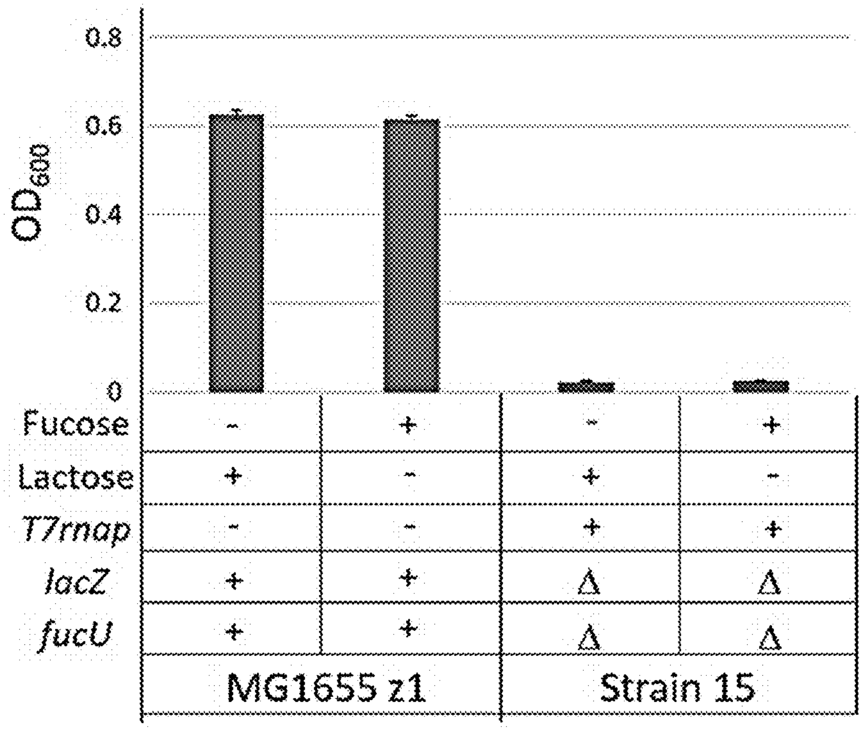
FIG. 3D shows a growth assay of MG1655 Z1 and Strain 15 (MG1655 Z1 with ΔfucU ΔlacZ, Table 1) in M9-minimal media with 1 g/L L-fucose or D-lactose. A indicates gene was removed from the genome. Error bars indicate s.d. (n=3 biological replicates).
Figure 4A:
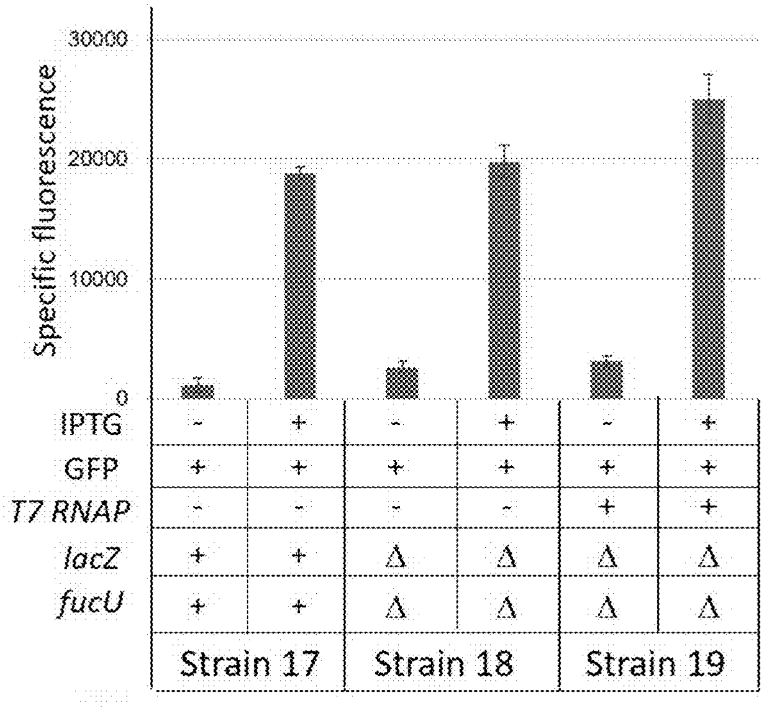
FIG. 4A, taken with FIG. 4B, shows GFP expression under lac-promoter variants in K-12 derivative strains. Cultures were grown in LB-media and induced with or without 1 mM IPTG at 37° C. for 24 h. GFP expression under promoter $P_{L1acO1}$ in Strain 17 (MG1655 Z1), Strain 18 (MG1655 Z1 with ΔfucU ΔlacZ) and Strain 19 (Strain 18 with ss9::$P_{lacUV5}$:T7rnap, Table 1).
Figure 4B:
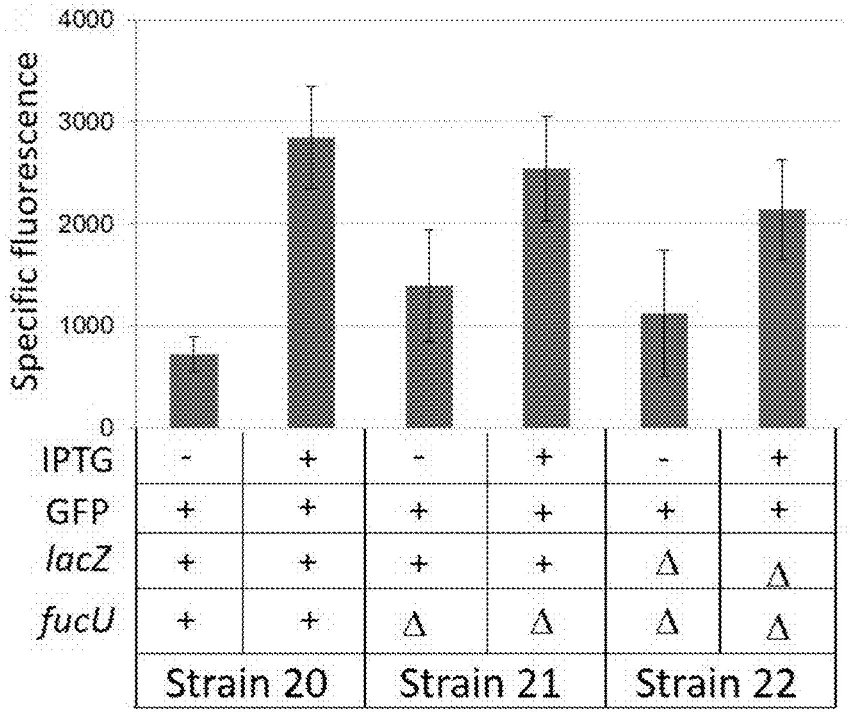
FIG. 4B shows GFP expression under promoter $P_{lacUV5}$ in Strain 20 (MG1655 Z1), Strain 21 (Strain 20 with ΔfucU) and Strain 22 (Strain 20 with ΔfucU ΔlacZ, Table 1). A indicates gene was removed from the genome. Error bars indicate s.d. (n=3 biological replicates).

To avoid the potential sequence similarity issues observed for $P_{lacUV5}$ and the native lacZ promoter, the three modifications into MG1655 Z1 were introduced in a different order. First, fucU and lacZ in MG1655 Z1 were deleted to form Strain 13 (ΔfucU) and Strain 14 (ΔfucU ΔlacZ)). Then, $P_{lacUV5}$: T7rnap was integrated into the ss9 locus to form Strain 15 (Table 1). Strain 15 was unable to grow on L-fucose or lactose as a sole carbon source (FIG. 3D). Although the $P_{lacUV5}$:T7rnap cassette in Strain 15 had no mutations, Strain 15 with pAL1834 harboring $P_{T7}$:sfgfp (Table 1: Strain 16) showed leaky GFP expression without IPTG. To determine if other lac-based promoters are deregulated by the strain modifications, pAL421 containing $P_{LlacO1}$:sfgfp was introduced into MG1655 z1, Strains 14 and 15 to form Strains 17, 18, and 19, respectively (Table 1) to assess the regulation of the lac-based promoter in these strains. The expressions from $P_{LlacO1}$ without IPTG were well repressed in Strains 17, 18 and 19 (FIG. 4A). Next, pAL2045 containing $P_{lacUV5}$:sfgfp was introduced into MG1655 z1, Strains 13 and 14 to form Strains 20, 21, and 22, respectively (Table 1). The expression of sfgfp in Strains 21 and 22 was leakier than that in Strain 20 (FIG. 4B), suggesting that the deletion of fucU caused the leaky expression of $P_{lacUV5}$.

Production of LDFT in K-12 Derivative Strains

Figure 5:
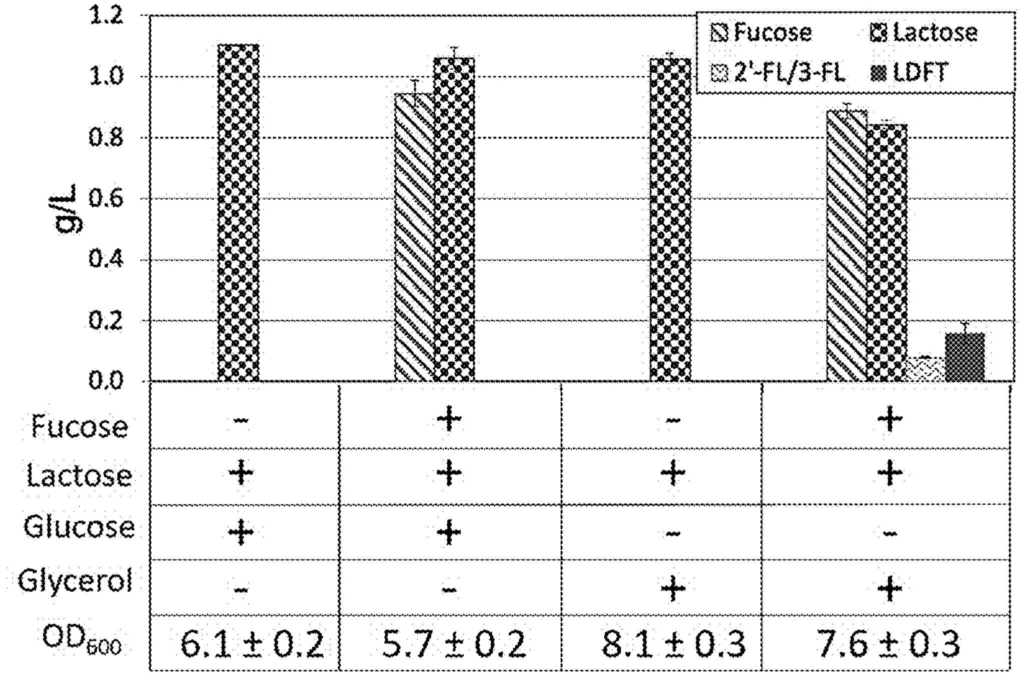
FIG. 5 shows the effects of carbon sources on LDFT production. Strain 23 (MG1655 Z1 ΔfucU ΔlacZ with the LDFT production plasmids, Table 1) was grown in M9P with 5 g/L glucose or 10 g/L glycerol at 30° C. for 24 h. Cultures were supplemented with 1 g/L lactose and with or without 1 g/L L-fucose and induced with 1 mM IPTG and 100 ng/mL aTc. L-Fucose concentration (diagonal), lactose concentration (checkered), monofucosides (2'-FL/3-FL) concentration (zigzag) and LDFT concentration (filled) were measured at 24 h. Error bars indicate s.d. (n=3 biological replicates).

Rather than pursuing alternative promoters for T7rnap, other induction systems for the LDFT biosynthetic pathway genes were used. The fkp and wbgL genes were cloned under $P_{LlacO1}$ (pAL1759, Tables 2 & 4) and the Hp3/4 ft gene was cloned under an aTc-inducible promoter $P_{LetO1}$ (pAL1760, Tables 2 & 4) (Lutz and Bujard, 1997). The LDFT production plasmids (pAL1759 and pAL1760) were introduced to Strain 14 to form Strain 23 (Table 1). Strain 23 was grown in M9P containing L-fucose and lactose with glucose or glycerol. After 24 h, Strain 23 produced 0.08 g/L 2'-FL and 0.16 g/L LDFT under the glycerol conditions, but neither were produced under the glucose conditions (FIG. 5).

Enhancing Substrate Levels by Overexpressing Transporter Genes

Figure 6:
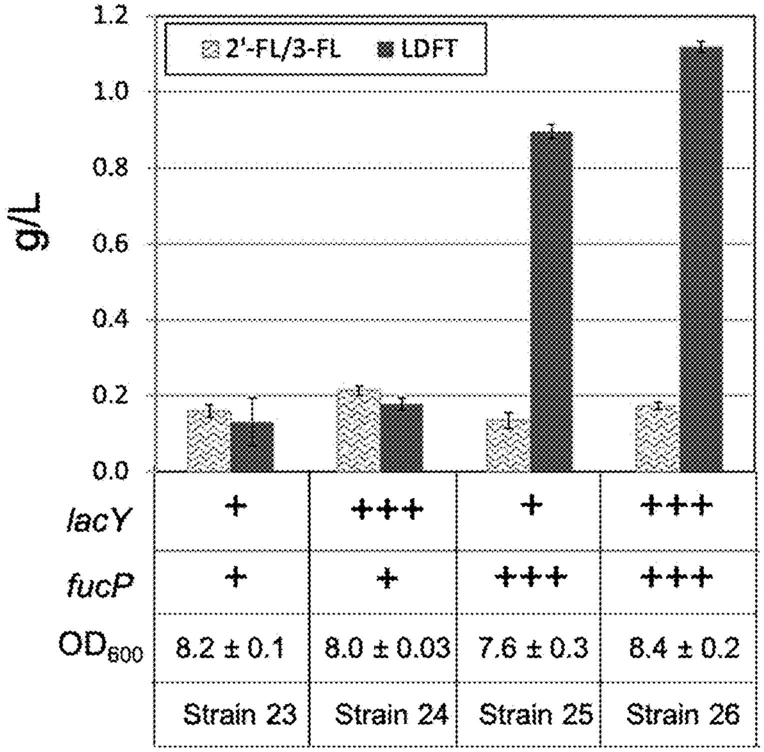
FIG. 6 shows the additional expression of lactose and L-fucose permease genes to enhance lactose and L-fucose availabilities. Strain 14 (MG1655 Z1 ΔfucU ΔlacZ, Table 1) was used as a host strain. Strain 23 (Strain 14 with the LDFT production plasmids), Strain 24 (Strain 14 with the LDFT production plasmids with lacY), Strain 25 (Strain 14 with the LDFT production plasmids with fucU), and Strain 26 (Strain 14 with the LDFT production plasmids with lacY and fucU) were grown in M9P with 10 g/L glycerol at 30° C. for 24 h. Cultures were supplemented with 1 g/L lactose and 1 g/L L-fucose and induced with 1 mM IPTG and 100 ng/mL aTc. Growth and production of monofucosides (2'-FL/3-FL, zigzag) and LDFT (filled) were determined at 24 h. + indicates the corresponding gene was expressed from the genome and +++ indicates the corresponding gene was additionally expressed from a plasmid. Error bars indicate s.d. (n=3 biological replicates).

Intracellular availability of L-fucose and lactose is important for efficient LDFT production. It was hypothesized that additional expression of the substrate transporter genes would increase the substrate supply and improve LDFT production. The lactose and L-fucose membrane symporter genes, lacY and fucP, were expressed under a constitutive promoter (iGEM part No. BBa_K1824896, Tables 2 & 4). The lacY gene was expressed from the fkp-wbgL plasmid pAL2027 (Tables 2 & 4). The LDFT production plasmids with lacY (pAL2027 and pAL1760) were introduced into Strain 14 to form Strain 24 (Table 1) but the overexpression of lacY did not improve LDFT production (FIG. 6). The fucP gene was expressed from the fkp-wbgL plasmid pAL2028 (Table 2). The LDFT production plasmids with fucP (pAL2028 and pAL1760) were introduced into Strain 14 to form Strain 25 (Table 1). After 24 h, Strain 25 produced 0.9 g/L LDFT, a 6.9-fold improvement compared to Strain 23.

Next, both lacY and fucU were expressed from the fkp-wbgL plasmid pAL2029 (Table 2). The LDFT-production plasmids with lacY and fucU (pAL2029 and pAL1760) were introduced into Strain 14 to form Strain 26 (Table 1). Strain 26 produced 1.1 g/L LDFT after 24 h, representing 59% of the theoretical maximum yield (TMY) from lactose and accumulated 0.17 g/L 2'-FL and/or 3-FL (FIG. 6). As the HPLC and the MS methods used were unable to discriminate between the two mono-fucosylated lactose, the combined concentrations of 2'-FL and 3-FL are reported here.

Tuning of the Expression Levels of the LDFT Biosynthetic Pathway Genes

Figure 7A:
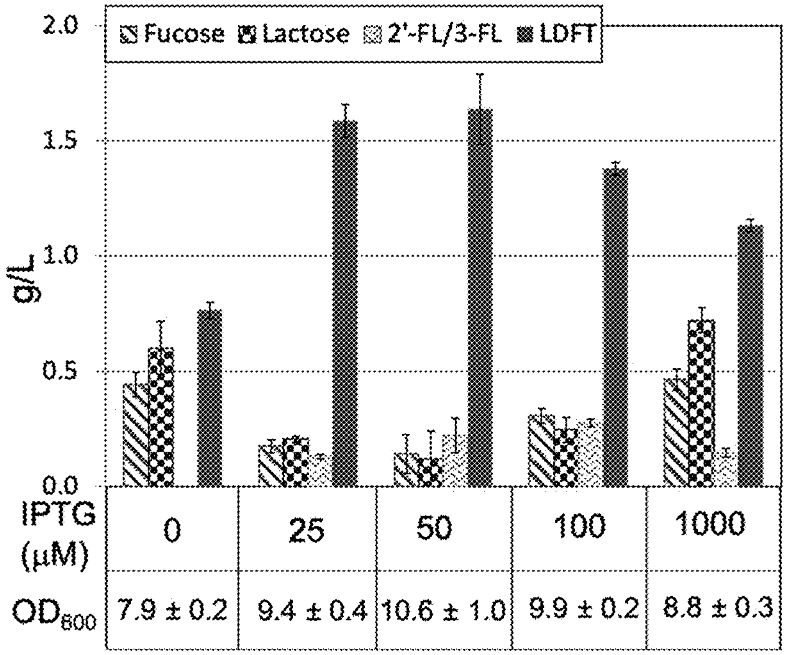
FIG. 7A, taken with FIG. 7B, shows the effects of IPTG and aTc concentrations on LDFT production. Strain 26 (MG1655 Z1 ΔfucU ΔlacZ with the LDFT production plasmids with lacY and fucU) was grown in M9P with 10 g/L glycerol at 30° C. for 24 h. Cultures were supplemented with 1 g/L lactose and 1 g/L fucose and induced with 100 ng/mL aTc and various concentrations of IPTG (0, 25, 50, 100 and 1000 μM).
Figure 7B:
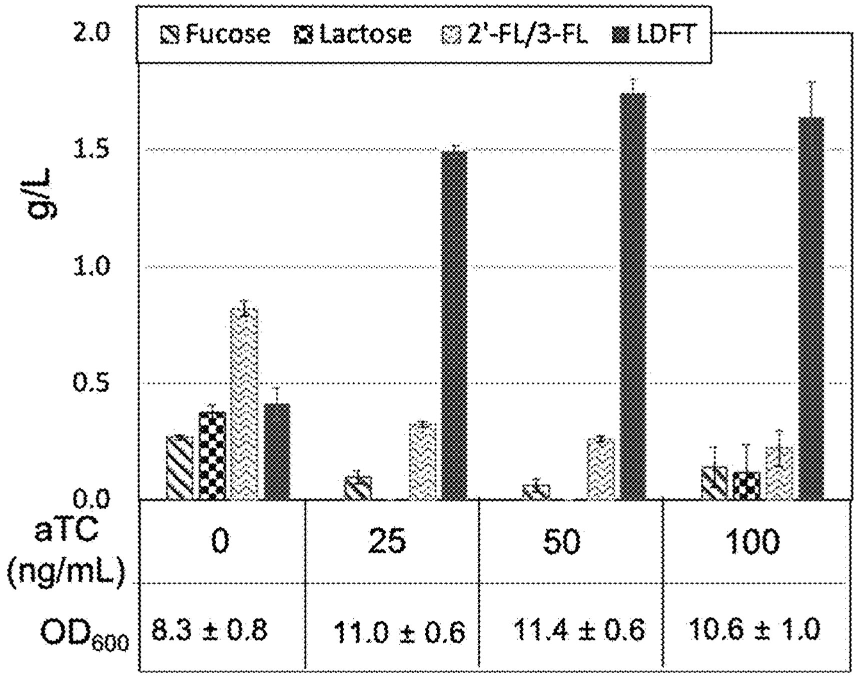
FIG. 7B shows results for Strain 26, grown as described for FIG. 7A except with 50 M IPTG and various concentrations of aTc (0, 25, 50, 100 ng/mL). $OD_{600}$, L-Fucose concentration (diagonal), lactose concentration (checkered), monofucosides (2'-FL/3-FL) concentration (zigzag) and LDFT concentration (filled) were measured at 24 h. Error bars indicate s.d. (n≥3 biological replicates).

To fine-tune the nucleotide activation of L-fucose and the fucosylation reactions, a range of IPTG concentrations (0, 25, 50, 100, and 1,000 μM) were screened for the expression of $P_{LlacO1}$:fkp-wbgL in the presence of 100 ng/mL aTc for induction of $P_{LtetO1}$:Hp3/4 ft. The best growth, greatest lactose and L-fucose consumption, and the highest level LDFT production (1.6 g/L, 89% of TMY) was observed with 50 μM IPTG (FIG. 7A). A range of aTc concentrations (0, 25, 50 and 100 ng/mL) were tested for the LDFT production in the presence of 50 μM IPTG to determine if adjusting Hp3/4FT expression levels could improve LDFT production. Strain 26 produced more LDFT with higher concentrations of aTc (FIG. 7B). Thus, the induction condition with 50 μM IPTG and 100 ng/mL aTc was used for further studies.

Characterization of LDFT Production

Figure 8A:
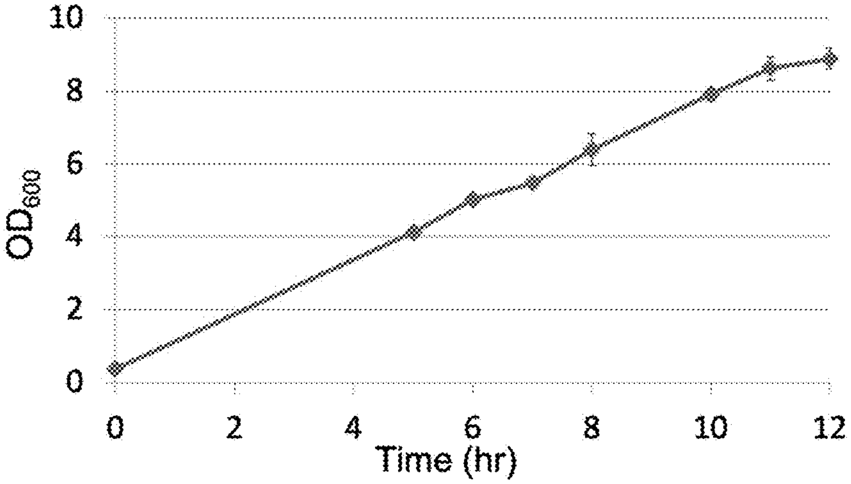
FIG. 8A shows growth ($OD_{600}$) of strain 26 (MG1655 z1 ΔfucU ΔlacZ with the LDFT production plasmids with lacY and fucU) in M9P with 20 g/L glycerol at 30° C. for 12 h. Cultures were supplemented with 1 g/L lactose and 1 g/L L-fucose and induced with 50 M IPTG and 100 ng/mL aTc. Error bars indicate s.d. (n=3 biological replicates).
Figure 8B:
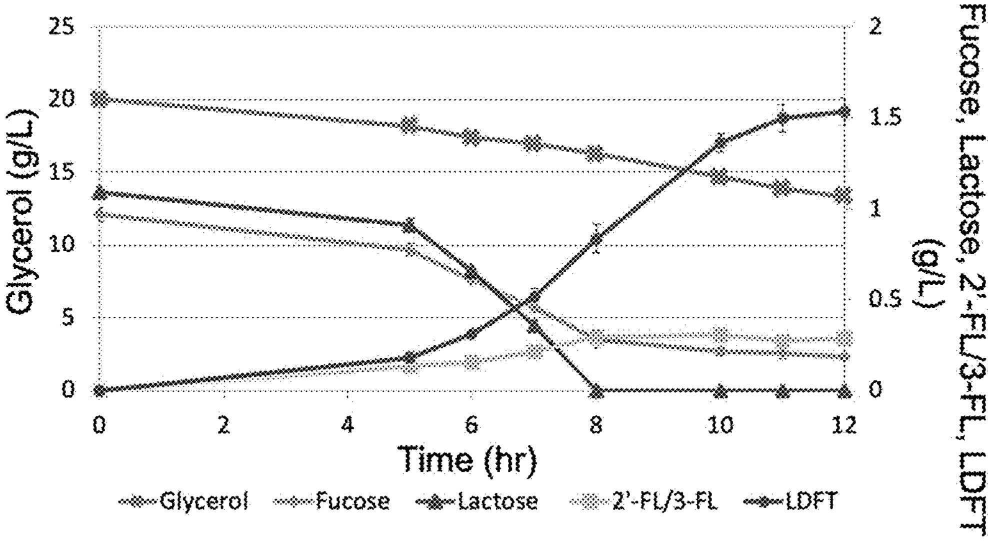
FIG. 8B shows glycerol concentration (cross), fucose concentration (diamond), lactose concentration (triangle), monofucosides (2'-FL/3-FL) concentration (square) and LDFT concentration (circle) were monitored during growth of Strain 26 as described for FIG. 8A. Error bars indicate s.d. (n=3 biological replicates).

The LDFT production profile in Strain 26 was characterized for 12 h post-induction by monitoring substrate, intermediate, side product, and LDFT levels using HPLC (FIG. 8). LDFT was first detected at 5 h, and between 5 to 10 h the production rate was 0.24 g/L/h (FIG. 8). Monofucosides (2'-FL/3-FL) were accumulated up to 0.3 g/L until lactose was depleted at 8 h and remained constant at ~0.3 g/L between 8 to 12 h. The lack of monofucoside consumption after 8 h indicated that most of the remaining monofucoside was 3-FL, which was the side product produced by Hp3/4FT from lactose that cannot be fucosylated further by WbgL to produce LDFT.

Figure 9:
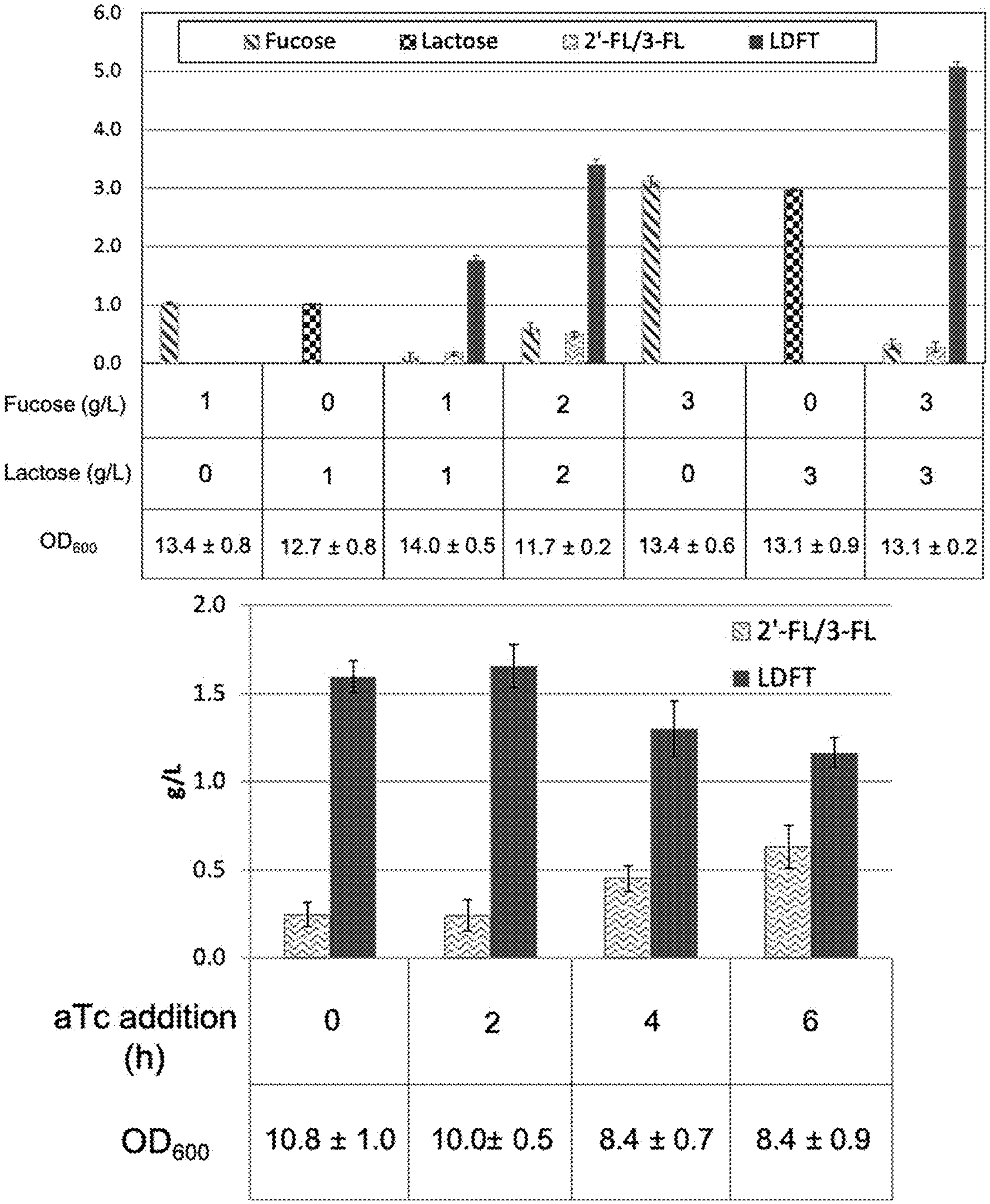
FIG. 9 shows sugar levels in cultures upon delayed expression of Hp3/4 ft in Strain 26. Strain 26 (MG1655 Z1 ΔfucU ΔlacZ with the LDFT production plasmids with lacY and fucU) was grown in M9P with 10 g/L glycerol at 30° C. for 24 h. Cultures were supplemented with 1 g/L lactose and 1 g/L L-fucose and induced with 50 μM IPTG at 0 h. 100 ng/mL aTc was added to cultures at 0, 2, 4, and 6 h. $OD_{600}$, monofucosides (2'-FL/3-FL) concentration (zigzag) and LDFT concentration (filled) were measured at 24 h. Error bars indicate s.d. (n=3 biological replicates).

When WbgL and Hp3/4FT are expressed at the same time, both enzymes can compete to fucosylate lactose into 2'-FL and 3-FL, respectively. In the presence of lactose and 2'-FL, Hp3/4FT can also convert the respective acceptor substrates into 3-FL and LDFT. It was hypothesized that the delayed induction of Hp3/4 ft would decrease the competition between WbgL and Hp3/4FT for lactose and decrease the production of the side product, 3-FL. Therefore, delaying of the Hp3/4FT expression was tested by adding 100 ng/mL aTc at 2, 4, and 6 h. However, the delayed expressions of Hp3/4 ft resulted in increased monofucoside accumulation and decreased LDFT production (FIG. 9). This increase in monofucoside in the supernatant suggests that 2'-FL formed by WbgL may be secreted to media and its reimport may be limited, which decreases the substrate availability of Hp3/4FT for LDFT production.

Figure 10:
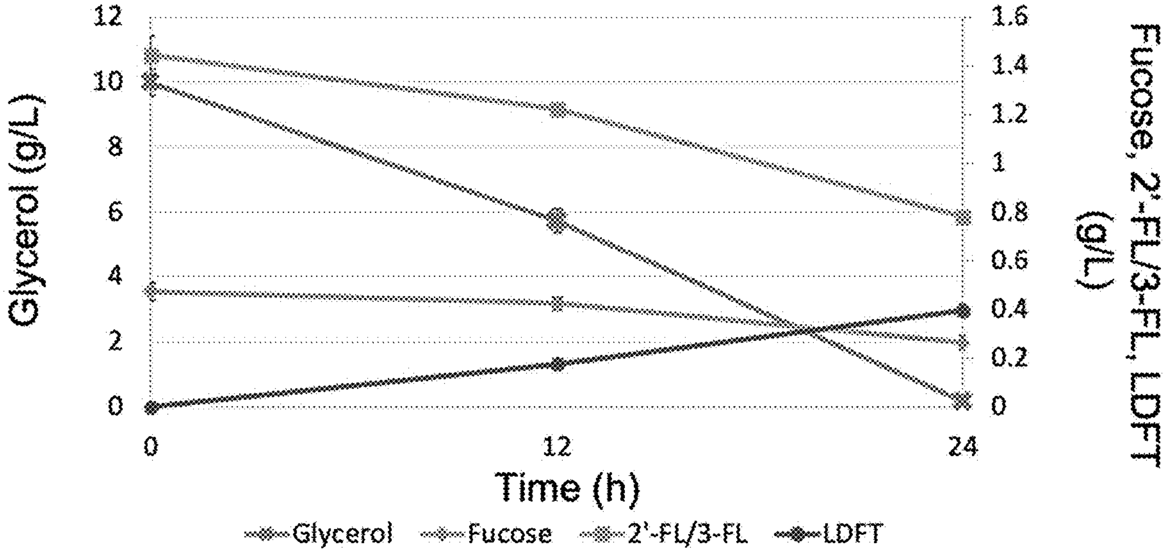
FIG. 10 shows LDFT production with 2'-FL feeding. The wbgL gene was removed from pAL2029, generating pAL2059 (Table 2). Strain 27 (MG1655 Z1 ΔfucU ΔlacZ harboring pAL1760 (Hp3/4 ft) and pAL2059 (fkp, lacY, and fucU), Table 1) was grown in M9P with 10 g/L glycerol at 30° C. for 24 h. Cultures were supplemented with 1.4 g/L 2'-FL (mole equivalent to 1 g/L lactose) and 0.5 g/L L-fucose and induced with 50 μM IPTG and 100 ng/mL aTc. Glycerol concentration (cross), L-fucose concentration (diamond), 2'-FL concentration (square) and LDFT concentration (circle) were monitored during the experiment. Error bars indicate s.d. (n=3 biological replicates).

To examine the import efficiency of 2'-FL, 2'-FL was fed to the production cultures. The wbgL gene was removed from pAL2029 to form pAL2059 (Table 2). pAL2059 and pAL1760 were introduced into Strain 14 to form Strain 27 (Table 1). Strain 27 was grown in M9P with 10 g/L glycerol. Cultures were induced with 50 μM IPTG and 100 ng/mL aTc and supplemented with 1.42 g/L of 2'-FL (mole equivalent to 1 g/L lactose) and 0.5 g/L L-fucose. Lactose was not fed to the cultures and wbgL was not present in system, making it unlikely for Strain 27 to produce 2'-FL and 3-FL. Under these conditions, LDFT should be produced only from the fed 2'-FL. Strain 27 produced only 0.4 g/L LDFT in 24 h, further supporting that the import of 2'-FL is not efficient in *E. coli* (FIG. 10).

LDFT Production with Higher Substrate Concentrations

Figure 11:
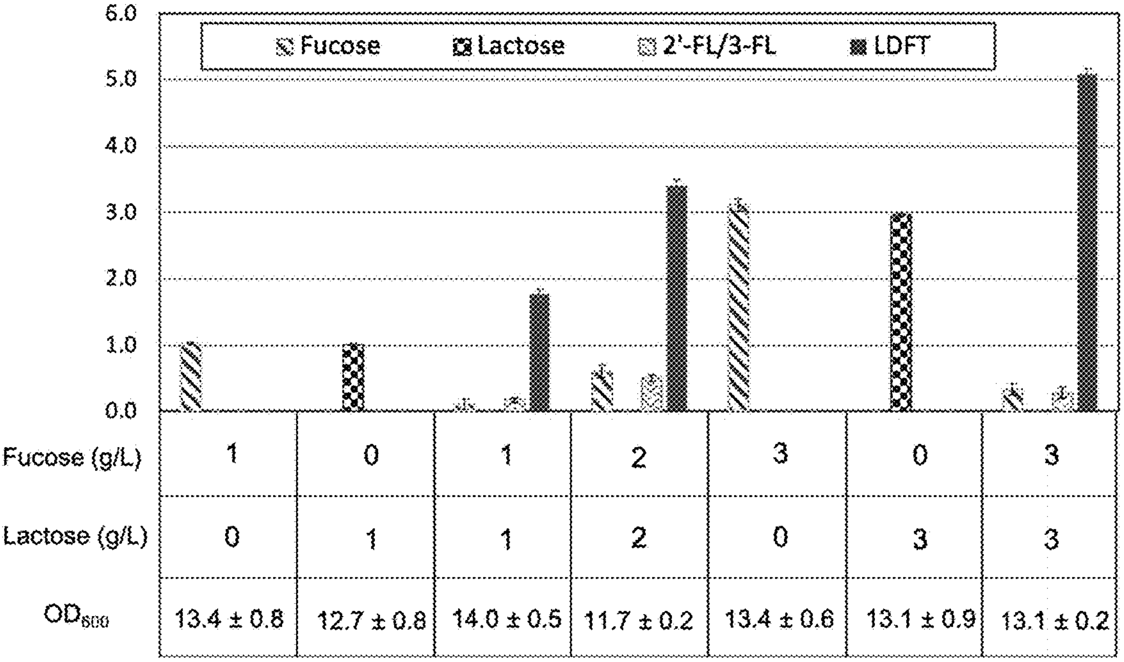
FIG. 11 shows LDFT production in Strain 26 with various concentrations of lactose and fucose. Strain 26 (MG1655 Z1 ΔfucU ΔlacZ with the LDFT production plasmids with lacY and fucU) was grown in M9P with 20 g/L glycerol at 30° C. for 24 h. Cultures were supplemented with lactose and L-fucose and induced with 50 μM IPTG and 100 ng/mL aTc. $OD_{600}$, L-fucose concentration (diagonal), lactose concentration (dotted), 2'-FL concentration (wave) and LDFT concentration (filled) were measured at 24 h. Error bars indicate s.d. (n≥3 biological replicates).

Strain 26 consumed 1 g/L lactose within 8 h and LDFT production reached completion at 12 h post-induction (FIG. 8). To evaluate LDFT production with higher substrate concentrations, Strain 26 was grown in M9P with 20 g/L glycerol and various amounts of lactose and L-fucose (1, 2, or 3 g/L) for 24 h. In conditions with only lactose or L-fucose as the added substrate, Strain 26 did not produce any detectable amounts of fucosides. In the presence of both substrates, the increase in LDFT yield was nearly proportional to the increase of substrate concentrations (FIG. 11). Strain 26 consumed 3.0 g/L lactose and 2.6 g/L L-fucose and produced 5.1 g/L LDFT in 24 h. LDFT was produced at 910% of TMY.

Discussion

LDFT has been identified as an effective gastrointestinal and immunological modulator and has the potential to be developed to treat human diseases. Its high cost and limited commercial access make LDFT a desirable target for production in microbial hosts. Systems developed in *E. coli, B. subtilis*, and *S. cerevisiae* have successfully produced HMOs such as 2'-FL, 3-FL, LNT, and LNnT, which represent only a small fraction of over 200 naturally occurring HMOs. Developing microbial production systems dedicated to synthesizing HMOs with a higher structural complexity is still challenging. In this study, a microbial system that specifically and efficiently produces LDFT was established.

The greatest challenge of this study was pairing an α1-2-fucosyltransferase with an α1-3-fucosyltransferase that can efficiently produce LDFT with minimal accumulation of monofucoside intermediates. WbgL was chosen to drive lactose fucosylation into 2'-FL because it expresses well in *E. coli* and has been characterized to prefer β1-4-linked galactose substrates, such as lactose and LacNAc (Engels and Elling, 2014). From acceptor substrate screenings of α1-3-fucosylatransferases, Hp3/4FT was annotated with high activity towards 2'-fucosyl LacNAc, which suggested 2'-FL may also be a suitable acceptor for Hp3/4FT (Ma et al., 2006; Yu et al., 2017). Characterization of LDFT production as described herein demonstrated that Hp3/4FT had preferential activity towards 2'-FL over lactose and LDFT was formed as the dominant product (FIG. 8). The presence of residual monofucosides indicates possible formation of the side product 3-FL, which is an unsuitable acceptor for WbgL (Engels and Elling, 2014). Monofucoside titers were relatively low and can be separated from LDFT in downstream purification processes. Other fucosyltransferases that may be employed include, but are not limited to, α1-2-fucosyltransferases such as Hm2FT (GenBank: CBG40460), *E. coli* 0128:B12 α1-2-fucosyltransferase WbsJ (GenBank: AAO37698.1), *H. pylori* UA1234 α1-2-fucosyltransferase (Hp2FTa) (GenBank: AAD29863.1), *H. pylori* UA802 α1-2-fucosyltransferase (Hp2FTb) (GenBank: AAC99764.1), and related eukaryotic α1-2-fucosyltransferases (see, e.g., cazy.org/GT11_characterized.html); as well as α1-3-fucosyltransferases such as *H. pylori* ATCC43504 α1-3-fucosyltransferase (Hp3FT) (GenBank: AAB93985), *H. pylori* J99 α1-3-fucosyltransferase (Hp3FT) (GenBank: AAD06169.1, AAD06573.1), *H. pylori* NCTC11639 α1-3-fucosyltransferase (Hp3FT) (GenBank: AAB93985), and related eukaryotic α1-3-fucosyltransferases and α1-3/4-fucosyltransferases (see, e.g., cazy.org/GT10_characterized.html). It is possible to screen α1-3-fucosyltransferases for lower activity towards lactose and higher activity towards 2'-FL, and also pursue protein engineering strategies to expand α1-2-fucosyltransferase's acceptor substrate range to 3-FL so that this side product can be fucosylated into LDFT.

The rate of LDFT formation was dictated by carbon catabolite repression (CCR) and the activity of sugar transporters, which firmly control the import of carbohydrates across the inner membrane (Görke and Stülke, 2008). It has been shown that import of glucose through the phosphotransferase system inhibits transcription of lac operon genes, including lacY. From the experiments described above, glucose conditions led to suppressed LDFT production while glycerol conditions resulted in improved LDFT production. This suggests glucose inhibits lactose import whereas glycerol allows for lactose import through sufficient lacY expression. Although glucose is a traditional carbon feedstock for microbial fermentation, it is unsuitable for HMO production systems that use lactose as a substrate. In the absence of CCR, LDFT production was still limited by the native expression levels of lacY and fucP (FIG. 6). Additional expression of fucP increased LDFT production by 6.9-fold to 0.9 g/L (FIG. 6), indicating that L-fucose import was one of the bottlenecks for LDFT production. While native expression levels of lacY without CCR were adequate for supplying lactose, overexpression of lacY and fucU further balanced the donor-acceptor substrate ratio and improved LDFT titers to 1.1 g/L in 24 h (FIG. 6).

Lastly, balancing expression levels of the LDFT biosynthetic pathway genes (fkp, wbgL, and Hp3/4 ft) increased efficiency of LDFT production. Decreasing expression of fkp reduces excessive ATP and GTP consumption in GDP-fucose production, potentially relieving the metabolic burden of regenerating nucleotide cofactors (FIG. 7A). Decreasing expression of wbgL helps synchronize 2'-FL production with Hp3/4FT's slower turnover rate, streamlining 2'-FL towards LDFT production (FIG. 7A). Decreasing or delaying Hp3/4 ft expression causes build-up of 2'-FL, which is rapidly exported from the cell (FIG. 7B). It has been hypothesized that LacY is an importer for 2'-FL (Shin et al., 2020), but enhanced lacY expression was still insufficient for LDFT production from 2'-FL feeding (FIG. 10). Expression of additional heterologous importers may improve 2-FL transport. Fucosyllactose transporters have been identified in gut prebiotic *Bifidobacterium* species and are ideal candidates for screening in further studies to improve LDFT production (Sakanaka et al., 2019). Examples of such transporters include ABC transporters FL transporter-1 and FL transporter 2-from *Bifidobacterium longum* subsp. *infantis* ATCC 15697. FL transporter-1 is made up of the domains set forth in SEQ ID NOS:19-21 and transports 2'-fucosyllactose and 3-fucosyllactose, while FL transporter-2 is made up of the domains set forth in SEQ ID NOS:22-24 and transports 2'-FL, 3-FL, LDFT, and LNFP I.

Due to concerns about strain virulence for the production of bioactive compounds, the HMO production technologies can be translated to nonpathogenic generally-recognized-as-safe (GRAS) strains such as *Bacillus subtilis, Corynebacterium glutamicum*, and *Saccharomyces cerevisiae* (Becker et al., 2018; Kaspar et al., 2019; Lian et al., 2018). For example, lactose transporters can also be introduced into hosts such as *C. glutamicum* as described by Shen et al. (*Microb Cell Fact* (2019) 18:51). Expression of known FucU and LacZ homologes (e.g., *B. subtilis* homologs set forth in SEQ ID NO:25 and SEQ ID NO:26), can be reduced or eliminated as described above for *E. coli*. Alternatively, host cells such as *S. cerevisiae* which are not known to express FucU homologs would not require such modifications. Advancements in GRAS strains' synthetic biology toolbox such as genome editing, vector expression systems, and tuning of gene expression has improved their industrial application in producing nutraceuticals, food additives and biofuels. Some of these GRAS hosts also enable post-translational modification of enzymes and localization of proteins into organelles or on membranes. Development of GRAS HMO fucosylation systems would also forge production routes for other fucosylated compounds for pharmaceutical research.

REFERENCES

Ágoston, K., Hederos, M., Bajza, I., Dekany, G., 2019. Kilogram scale chemical synthesis of 2'-fucosyllactose. Carbohydr. Res. 476, 71-77.

Ayechu-Muruzabal, V., van Stigt, A. H., Mank, M., Willemsen, L. E. M., Stahl, B., Garssen, J., van't Land, B., 2018. Diversity of Human Milk Oligosaccharides and Effects on Early Life Immune Development. Front. Pediatr. 6, 239.

Bai, J., Wu, Z., Sugiarto, G., Gadi, M. R., Yu, H., Li, Y., Xiao, C., Ngo, A., Zhao, B., Chen, X., Guan, W., 2019. Biochemical characterization of *Helicobacter pylori* α1-3-fucosyltransferase and its application in the synthesis of fucosylated human milk oligosaccharides. Carbohydr. Res. 480, 1-6.

Ballard, O., Morrow, A. L., 2013. Human milk composition: nutrients and bioactive factors. Pediatr. Clin. North Am. 60, 49-74.

Bandara, M. D., Stine, K. J., Demchenko, A. V, 2020. Chemical synthesis of human milk oligosaccharides: lacto-N-neohexaose (Galβ1→4GlcNAβ1→)2 3,6Galβ1→4Glc. Org. Biomol. Chem. 18, 1747-1753.

Bandara, M. D., Stine, K. J., Demchenko, A. V, 2019. The chemical synthesis of human milk oligosaccharides: Lacto-N-neotetraose (Galβ1→4GlcNAcβ1→3Galβ1→4Glc). Carbohydr. Res. 483, 107743.

Bassalo, M. C., Garst, A. D., Halweg-Edwards, A. L., Grau, W. C., Domaille, D. W., Mutalik, V. K., Arkin, A. P., Gill, R. T., 2016. Rapid and Efficient One-Step Metabolic Pathway Integration in *E. coli*. ACS Synth. Biol. 5, 561-568.

Baumgärtner, F., Conrad, J., Sprenger, G. A., Albermann, C., 2014. Synthesis of the human milk oligosaccharide lacto-N-tetraose in metabolically engineered, plasmid-free *E. coli*. Chembiochem 15, 1896-1900.

Becker, J., Rohles, C. M., Wittmann, C., 2018. Metabolically engineered *Corynebacterium glutamicum* for bio-based production of chemicals, fuels, materials, and healthcare products. Metab. Eng. 50, 122-141.

Berger, P. K., Plows, J. F., Jones, R. B., Alderete, T. L., Yonemitsu, C., Poulsen, M., Ryoo, J. H., Peterson, B. S., Bode, L., Goran, M. I., 2020. Human milk oligosaccharide 2'-fucosyllactose links feedings at 1 month to cognitive development at 24 months in infants of normal and overweight mothers. PLoS One 15, e0228323.

Bode, L., 2012. Human milk oligosaccharides: every baby needs a sugar mama. Glycobiology 22, 1147-1162.

Borewicz, K., Gu, F., Saccenti, E., Hechler, C., Beijers, R., de Weerth, C., van Leeuwen, S. S., Schols, H. A., Smidt, H., 2020. The association between breastmilk oligosaccharides and faecal microbiota in healthy breastfed infants at two, six, and twelve weeks of age. Sci. Rep. 10, 4270.

Brückner, R., Titgemeyer, F., 2002. Carbon catabolite repression in bacteria: choice of the carbon source and autoregulatory limitation of sugar utilization. FEMS Microbiol. Lett. 209, 141-148.

Chaturvedi, P., Warren, C. D., Altaye, M., Morrow, A. L., Ruiz-Palacios, G., Pickering, L. K., Newburg, D. S., 2001. Fucosylated human milk oligosaccharides vary between individuals and over the course of lactation. Glycobiology 11, 365-372.

Chen, X., 2015. Human Milk Oligosaccharides (HMOS): Structure, Function, and Enzyme-Catalyzed Synthesis. Adv. Carbohydr. Chem. Biochem. 72, 113-190.

Choi, Y. H., Park, B. S., Seo, J.-H., Kim, B.-G., 2019. Biosynthesis of the human milk oligosaccharide 3-fucosyllactose in metabolically engineered *Escherichia coli* via the salvage pathway through increasing GTP synthesis and β-galactosidase modification. Biotechnol. Bioeng. 116, 3324-3332.

Dong, X., Li, N., Liu, Z., Lv, X., Li, J., Du, G., Wang, M., Liu, L., 2019. Modular pathway engineering of key precursor supply pathways for lacto-N-neotetraose production in *Bacillus subtilis*. Biotechnol. Biofuels 12, 212.

Engels, L., Elling, L., 2014. WbgL: a novel bacterial α1,2-fucosyltransferase for the synthesis of 2'-fucosyllactose. Glycobiology 24, 170-178.

Gorke, B., Stülke, J., 2008. Carbon catabolite repression in bacteria: many ways to make the most out of nutrients. Nat. Rev. Microbiol. 6, 613-624.

Hegar, B., Wibowo, Y., Basrowi, R. W., Ranuh, R. G., Sudarmo, S. M., Munasir, Z., Atthiyah, A. F., Widodo, A. D., Supriatmo, Kadim, M., Suryawan, A., Diana, N. R., Manoppo, C., Vandenplas, Y., 2019. The Role of Two Human Milk Oligosaccharides, 2'-Fucosyllactose and Lacto-N-Neotetraose, in Infant Nutrition. Pediatr. Gastroenterol. Hepatol. Nutr. 22, 330-340.

Huang, D., Yang, K., Liu, J., Xu, Y., Wang, Y., Wang, R., Liu, B., Feng, L., 2017. Metabolic engineering of *Escherichia coli* for the production of 2'-fucosyllactose and 3-fucosyllactose through modular pathway enhancement. Metab. Eng. 41, 23-38.

Jiang, Y., Chen, B., Duan, C., Sun, B., Yang, J., Yang, S., 2015. Multigene Editing in the *Escherichia coli* Genome via the CRISPR-Cas9 System. Appl. Environ. Microbiol. 81, 2506-2514.

Kaspar, F., Neubauer, P., Gimpel, M., 2019. Bioactive Secondary Metabolites from *Bacillus subtilis*: A Comprehensive Review. J. Nat. Prod. 82, 2038-2053.

Kopp, J., Slouka, C., Ulonska, S., Kager, J., Fricke, J., Spadiut, O., Herwig, C., 2017. Impact of Glycerol as Carbon Source onto Specific Sugar and Inducer Uptake Rates and Inclusion Body Productivity in *E. coli* BL21 (DE3). Bioeng. (Basel, Switzerland) 5, 1.

Kulinich, A., Liu, L., 2016. Human milk oligosaccharides: The role in the fine-tuning of innate immune responses. Carbohydr. Res. 432, 62-70.

Li, M. Z., Elledge, S. J., 2007. Harnessing homologous recombination in vitro to generate recombinant DNA via SLIC. Nat. Methods 4, 251-256.

Lian, J., Mishra, S., Zhao, H., 2018. Recent advances in metabolic engineering of *Saccharomyces cerevisiae*: New tools and their applications. Metab. Eng. 50, 85-108.

Liu, J. Y., Miller, P. F., Willard, J., Olson, E. R., 1999. Functional and Biochemical Characterization of *Escherichia coli* Sugar Efflux Transporters. J. Biol. Chem. 274, 22977-22984.

Liu, Y.-H., Wang, L., Huang, P., Jiang, Z.-Q., Yan, Q.-J., Yang, S.-Q., 2020. Efficient sequential synthesis of lacto-N-triose II and lacto-N-neotetraose by a novel β-N-acetylhexosaminidase from *Tyzzerella nexilis*. Food Chem. 332, 127438.

Lutz, R., Bujard, H., 1997. Independent and tight regulation of transcriptional units in *Escherichia coli* via the LacR/O, the TetR/O and AraC/I1-I2 regulatory elements. Nucleic Acids Res. 25, 1203-1210.

Ma, B., Audette, G. F., Lin, S., Palcic, M. M., Hazes, B., Taylor, D. E., 2006. Purification, Kinetic Characterization, and Mapping of the Minimal Catalytic Domain and the Key Polar Groups of *Helicobacter pylori* α-(1,3/1,4)-Fucosyltransferases. J. Biol. Chem. 281, 6385-6394.

McArthur, J. B., Yu, H., Chen, X., 2019. A Bacterial β1-3-Galactosyltransferase Enables Multigram-Scale Synthesis of Human Milk Lacto-N-tetraose (LNT) and Its Fucosides. ACS Catal. 9, 10721-10726.

Newburg, D. S., Tanritanir, A. C., Chakrabarti, S., 2016. Lactodifucotetraose, a human milk oligosaccharide, attenuates platelet function and inflammatory cytokine release. J. Thromb. Thrombolysis 42, 46-55.

Nidetzky, B., Gutmann, A., Zhong, C., 2018. Leloir Glycosyltransferases as Biocatalysts for Chemical Production. ACS Catal. 8, 6283-6300.

Orczyk-Pawilowicz, M., Lis-Kuberka, J., 2020. The Impact of Dietary Fucosylated Oligosaccharides and Glycoproteins of Human Milk on Infant Well-Being. Nutrients 12, 1105.

Paulsen, I. T., Chauvaux, S., Choi, P., Saier Jr, M. H., 1998. Characterization of glucose-specific catabolite repression-resistant mutants of *Bacillus subtilis*: identification of a novel hexose:H+ symporter. J. Bacteriol. 180, 498-504.

Rasko, D. A., Wang, G., Palcic, M. M., Taylor, D. E., 2000. Cloning and Characterization of the α(1,3/4) Fucosyltransferase of *Helicobacter pylori*. J. Biol. Chem. 275, 4988-4994.

Rosano, G. L., Ceccarelli, E. A., 2014. Recombinant protein expression in *Escherichia coli*: advances and challenges. Front. Microbiol. 5, 172.

Rudloff, S., Kunz, C., 2012. Milk oligosaccharides and metabolism in infants. Adv. Nutr. 3, 3985-4055.

Sakanaka, M., Hansen, M. E., Gotoh, A., Katoh, T., Yoshida, K., Odamaki, T., Yachi, H., Sugiyama, Y., Kurihara, S., Hirose, J., Urashima, T., Xiao, J., Kitaoka, M., Fukiya, S., Yokota, A., Lo Leggio, L., Abou Hachem, M., Katayama, T., 2019. Evolutionary adaptation in fucosyllactose uptake systems supports bifidobacteria-infant symbiosis. Sci. Adv. 5, eaaw7696.

Shin, J., Park, M., Kim, C., Kim, H., Park, Y., Ban, C., Yoon, J.-W., Shin, C.-S., Lee, J. W., Jin, Y.-S., Park, Y.-C., Min, W.-K., Kweon, D.-H., 2020. Development of fluorescent *Escherichia coli* for a whole-cell sensor of 2'-fucosyllactose. Sci. Rep. 10, 10514.

Smilowitz, J. T., Lebrilla, C. B., Mills, D. A., German, J. B., Freeman, S. L., 2014. Breast Milk Oligosaccharides: Structure-Function Relationships in the Neonate. Annu. Rev. Nutr. 34, 143-169.

Triantis, V., Bode, L., van Neerven, R. J. J., 2018. Immunological Effects of Human Milk Oligosaccharides. Front. Pediatr. 6, 190.

Wiciński, M., Sawicka, E., Gębalski, J., Kubiak, K., Malinowski, B., 2020. Human Milk Oligosaccharides: Health Benefits, Potential Applications in Infant Formulas, and Pharmacology. Nutrients 12, 266.

Xiao, Z., Guo, Y., Liu, Y., Li, L., Zhang, Q., Wen, L., Wang, X., Kondengaden, S. M., Wu, Z., Zhou, J., Cao, X., Li, X., Ma, C., Wang, P. G., 2016. Chemoenzymatic Synthesis of a Library of Human Milk Oligosaccharides. J. Org. Chem. 81, 5851-5865.

Ye, J., Xia, H., Sun, N., Liu, C.-C., Sheng, A., Chi, L., Liu, X.-W., Gu, G., Wang, S.-Q., Zhao, J., Wang, P., Xiao, M., Wang, F., Cao, H., 2019. Reprogramming the enzymatic assembly line for site-specific fucosylation. Nat. Catal. 2, 514-522.

Yi, W., Liu, X., Li, Y., Li, J., Xia, C., Zhou, G., Zhang, W., Zhao, W., Chen, X., Wang, P. G., 2009. Remodeling bacterial polysaccharides by metabolic pathway engineering. Proc. Natl. Acad. Sci. U.S.A. 106, 4207-4212.

Yu, H., Chen, X., 2019. CHAPTER 11 Enzymatic and Chemoenzymatic Synthesis of Human Milk Oligosaccharides (HMOS), in: Synthetic Glycomes. The Royal Society of Chemistry, pp. 254-280.

Yu, H., Li, Y., Wu, Z., Li, L., Zeng, J., Zhao, C., Wu, Y., Tasnima, N., Wang, J., Liu, H., Gadi, M. R., Guan, W., Wang, P. G., Chen, X., 2017. *H. pylori* α1-3/4-fucosyltransferase (Hp3/4FT)-catalyzed one-pot multienzyme (OPME) synthesis of Lewis antigens and human milk fucosides. Chem. Commun. 53, 11012-11015.

Yu, H., Thon, V., Lau, K., Cai, L., Chen, Y., Mu, S., Li, Y., Wang, P. G., Chen, X., 2010. Highly efficient chemoenzymatic synthesis of β1-3-linked galactosides. Chem. Commun. (Camb). 46, 7507-7509.

Yu, S., Liu, J.-J., Yun, E. J., Kwak, S., Kim, K. H., Jin, Y.-S., 2018. Production of a human milk oligosaccharide 2'-fucosyllactose by metabolically engineered *Saccharomyces cerevisiae*. Microb. Cell Fact. 17, 101.

Zhao, C., Wu, Y., Yu, H., Shah, I. M., Li, Y., Zeng, J., Liu, B., Mills, D. A., Chen, X., 2016. The one-pot multienzyme (OPME) synthesis of human blood group H antigens and a human milk oligosaccharide (HMOS) with highly active *Thermosynechococcus elongatus* α1-2-fucosyltransferase. Chem. Commun. 52, 3899-3902.

IV. Exemplary Embodiments

Exemplary embodiments provided in accordance with the presently disclosed subject matter include, but are not limited to, the claims and the following embodiments:

1. A recombinant cell for production of an oligosaccharide product, the recombinant cell comprising:
   a polynucleotide encoding a first glycosyltransferase polypeptide having a first substrate selectivity, and
   a polynucleotide encoding a second glycosyltransferase polypeptide having a second substrate selectivity.
2. The recombinant cell of embodiment 1, further comprising one or more polynucleotides selected from the group consisting of:

a polynucleotide encoding a nucleotide sugar pyrophosphorylase polypeptide,
a monosaccharide transporter polypeptide, and
an oligosaccharide transporter polypeptide.

3. The recombinant cell of embodiment 1 or 2, for production of an oligosaccharide comprising two or more fucose moieties, comprising:
a polynucleotide encoding a first fucosyltransferase polypeptide having a first substrate selectivity, and
a polynucleotide encoding a second fucosyltransferase polypeptide having a second substrate selectivity;
and optionally comprising one or more of:
a polynucleotide encoding a nucleotide sugar pyrophosphorylase polypeptide,
a polynucleotide encoding a lactose transporter polypeptide, and
a polynucleotide encoding an L-fucose transporter polypeptide.

4. The recombinant cell of embodiment 2 or embodiment 3, wherein the nucleotide sugar pyrophosphorylase polypeptide is a bifunctional glycokinase and nucleotide sugar pyrophosphorylase polypeptide.

5. The recombinant cell of embodiment 3 or embodiment 4, wherein the first fucosyltransferase polypeptide is an α1-2-fucosyltransferase polypeptide.

6. The recombinant cell of embodiment 5, wherein the α1-2-fucosyltransferase polypeptide is an *E. coli* 0126 α1-2-fucosyltransferase WbgL polypeptide.

7. The recombinant cell of embodiment 5 or embodiment 6, wherein the α1-2-fucosyltransferase polypeptide is an *E. coli* O126 α1-2-fucosyltransferase (WbgL) polypeptide (GenBank: ABE98421.1), an *H. mustelae* 12198 α1-2-fucosyltransferase (Hm2FT) polypeptide (GenBank: CBG40460), an *E. coli* 0128:B12 α1-2-fucosyltransferase (WbsJ) polypeptide (GenBank: AAO37698.1), an *H. pylori* UA1234 α1-2-fucosyltransferase (Hp2FTa) polypeptide (GenBank: AAD29863.1), or an *H. pylori* UA802 α1-2-fucosyltransferase (Hp2FTb) polypeptide (GenBank: AAC99764.1).

8. The recombinant cell of any one of embodiments 3-7, wherein the second fucosyltransferase polypeptide is an α1-3-fucosyltransferase polypeptide.

9. The recombinant cell of embodiment 8, wherein the α1-3-fucosyltransferase polypeptide is a truncated α1-3-fucosyltransferase polypeptide.

10. The recombinant cell of embodiment 8 or embodiment 9, wherein the α1-3-fucosyltransferase polypeptide is an *H. pylori* UA948 α1-3/4-fucosyltransferase (Hp3/4FT) polypeptide (GenBank: AAF35291.2), an *H. pylori* ATCC43504 α1-3-fucosyltransferase (Hp3FT) polypeptide (GenBank: AAB93985), an *H. pylori* J99 α1-3-fucosyltransferase (Hp3FT) polypeptide (GenBank: AAD06169.1, AAD06573.1), an *H. pylori* NCTC11637 α1-3-fucosyltransferase (Hp3FT) polypeptide (GenBank: AAB93985), a *B. fragilis* NCTC 9343 α1-3/4-fucosyltransferase polypeptide (GenBank: CAH09495.1), or an *H. hepaticus* ATCC 51449 Hh0072 polypeptide (GenBank: AAP76669.1).

11. The recombinant cell of any one of embodiments 2-10, wherein the nucleotide sugar pyrophosphorylase polypeptide is a *B. fragilis* bifunctional L-fucokinase/GDP-L-fucose pyrophosphorylase (Fkp) polypeptide.

12. The recombinant cell of any one of embodiments 3-11, which is transformed with a first expression vector comprising:
the polynucleotide encoding the first fucosyltransferase polypeptide,
the polynucleotide encoding the nucleotide sugar pyrophosphorylase polypeptide,
the polynucleotide encoding the lactose transporter polypeptide, and
the polynucleotide encoding the L-fucose transporter polypeptide.

13. The recombinant cell of any one of embodiments 3-12, wherein the polynucleotide encoding the first fucosyltransferase polypeptide and the polynucleotide encoding the nucleotide sugar pyrophosphorylase polypeptide are operably linked to a first inducible promoter.

14. The recombinant cell of embodiment 13, wherein the first inducible promoter is a $P_{LLacO1}$ promoter.

15. The recombinant cell of any one of embodiments 3-14, wherein the polynucleotide encoding the second fucosyltransferase polypeptide is operably linked to a second inducible promoter.

16. The recombinant cell of embodiment 15, wherein the second inducible promoter is a $P_{LtetO1}$ promoter.

17. The recombinant cell of any one of embodiments 3-16, wherein the L-fucose transporter polypeptide is an *E. coli* FucP polypeptide.

18. The recombinant cell of any one of embodiments 3-17, wherein the lactose transporter polypeptide is an *E. coli* LacY polypeptide.

19. The recombinant cell of any one of embodiments 3-18, wherein the polynucleotide encoding the lactose transporter polypeptide and the polynucleotide encoding the L-fucose transporter polypeptide are operably linked to a constitutive promoter.

20. The recombinant cell of any one of embodiments 1-19, which is modified to eliminate or reduce expression of an L-fucose mutarotase.

21. The recombinant cell of embodiment 20, wherein the L-fucose mutarotase is *E. coli* fucU.

22. The recombinant cell of any one of embodiments 1-21, which is modified to reduce or eliminate expression of a β-galactosidase.

23. The recombinant cell of embodiment 22, wherein the β-galactosidase is *E. coli* LacZ.

24. The recombinant cell of any one of embodiments 1-23, further comprising an polynucleotide encoding an additional transporter polypeptide.

25. The recombinant cell of embodiment 24, wherein the additional transporter polypeptide is a *Bifidobacterium* fucosyllactose transporter polypeptide.

26. The recombinant cell of any one of embodiments 1-25, which is an *E. coli* cell, a *B. subtilis* cell, a *C. glutamicum* cell, or an *S. cerevisiae* cell.

27. The recombinant cell of embodiment 26, which is an *E. coli* BW25113 Z1 cell or an *E. coli* MG1655 Z1 cell.

28. A method for producing an oligosaccharide product comprising two or more fucose moieties, the method comprising culturing a recombinant cell according to any one of embodiments 1-27 in a cell culture medium comprising L-fucose, an oligosaccharide acceptor, and a carbon source;
wherein first glycosyltransferase is a first fucosyltransferase; the second glycosyltransferase is a second fucosyltransferase; and
wherein the cell is cultured under conditions in which the first fucosyltransferase polypeptide, the second fucosyltransferase polypeptide, and the oligosaccharide acceptor is converted to the difucosylated oligosaccharide.

29. The method of embodiment 28, wherein the oligosaccharide transporter polypeptide is a lactose transporter polypeptide; the monosaccharide transporter polypeptide is an L-fucose transporter polypeptide; and the nucleotide sugar pyrophosphorylase polypeptide, the lactose transporter polypeptide, and the L-fucose transporter polypeptide are expressed under the culture conditions.

30. The method of embodiment 28 or embodiment 29, wherein the oligosaccharide acceptor is lactose and the oligosaccharide product is lactodifucotetraose (LDFT).

31. The method of any one of embodiments 28-29, wherein the carbon source comprises glucose, glycerol, or a combination thereof.

32. The method of any one of embodiments 28-31, wherein expression of the nucleotide sugar pyrophosphorylase polypeptide and the first fucosyltransferase polypeptide is induced at a level corresponding to 30-40% of maximum level (e.g., with isopropyl β-D-1-thiogalactopyranoside in an amount around 50 μM).

33. The method of embodiment 32, wherein expression of the second fucosyltransferase polypeptide is induced at a maximum level (e.g., with anhydrotetracycline at around 100 ng/mL).

Although the foregoing has been described in some detail by way of illustration and example for purposes of clarity and understanding, one of skill in the art will appreciate that certain changes and modifications can be practiced within the scope of the appended claims. In addition, each reference provided herein is incorporated by reference in its entirety to the same extent as if each reference was individually incorporated by reference.

V. Informal Sequence Listing

SEQ ID NO: 1. *E. coli* 0126 α1-2-fucosyltransferase (WbgL) (GenBank: ABE98421.1)

```
  1   MSIIRLQGGL GNQLFQFSFG YALSKINGTP LYFDISHYAE NDDHGGYRLN NLQIPEEYLQ
 61   YYTPKINNIY KLLVRGSRLY PDIFLFLGFC NEFHAYGYDF EYIAQKWKSK KYIGYWQSEH
121   FFHKHILDLK EFFIPKNVSE QANLLAAKIL ESQSSLSIHI RRGDYIKNKT ATLTHGVCSL
181   EYYKKALNKI RDLAMIRDVF IFSDDIFWCK ENIETLLSKK YNIYYSEDLS QEEDLWLMSL
241   ANHHIIANSS FSWWGAYLGS SASQIVIYPT PWYDITPKNT YIPIVNHWIN VDKHSSC
```

SEQ ID NO: 2. *H. pylori* UA948 α1-3/4-fucosyltransferase (Hp3/4FT) (GenBank: AAF35291.2),

```
  1   MFQPLLDAFI DSTHLDETTH KPPLNVALAN WWPLKNSEKK GERDFILHFI LKQRYKIILH
 61   SNPNEPSDLV FGNPLEQARK ILSYQNTKRV FYTGENEVPN FNLEDYAIGF DELDENDRYL
121   RMPLYYAYLH YKAMLVNDTT SPYKLKALYT LKKPSHKFKE NHPNLCALIH NESDPWKRGE
181   ASFVASNPNA PIRNAFYDAL NAIEPVASGG SVKNTLGYKV KNKNEFLSQY KENLCFENSQ
241   GYGYVTEKIL DAYFSHTIPI YWGSPSVAKD FNPKSFVNVH DENNEDEAID YIRYLHAHQN
301   AYLDMLYENP LNTIDGKAGF YQDLSFEKIL DFFKNILEND TIYHCNDAHY SALHRDLNEP
361   LVSVDDLRRD HDDLRVNYDD LRVNYDDLRV NYDDLRVNYD DLRVNYDDLR RDHDDLRRDH
421   ERLLSKATPL LELSQNTSFK IYRKAYQKSL PLLRAIRRWV RK
```

SEQ ID NO: 3. *Bacteroides fragilis* bifunctional L fucokinase/GDP-L-fucose pyrophosphorylase (BfFKP) (GenBank: CAH08307.1)

```
  1   MQKLLSLPSN LVQSFHELER VNRTDWFCTS DPVGKKLGSG GGTSWLLEEC YNEYSDGATE
 61   GEWLEKEKRI LLHAGGQSRR LPGYAPSGKI LTPVPVERWE RGQHLGQNLL SLQLPLYEKI
121   MSLAPDKLHT LIASGDVYIR SEKPLQSIPE ADVVCYGLWV DPSLATHHGV FASDRKHPEQ
181   LDEMLQKPSL AELESLSKTH LFLMDIGIWL LSDRAVEILM KRSHKESSEE LKYYDLYSDF
241   GLALGTHPRI EDEEVNTLSV AILPLPGGEF YHYGTSKELI SSTLSVQNKV YDQRRIMHRK
301   VKPNPAMFVQ NAVVRIPLCA ENADLWIENS HIGPKWKIAS RHIITGVPEN DWSLAVPAGV
361   CVDVVPMGDK GFVARPYGLD DVFKGDLRDS KTTLTGIPFG EWMSKRGLSY TDLKGRTDDL
421   QAVSVFPMVN SVEELGLVLR WMLSEPELEE GKNIWLRSEH FSADEISAGA NLKRLYAQRE
481   EFRKGNWKAL AVNHEKSVFY QLDLADAAED FVRLGLDMPE LLPEDALQMS RIHNRMLRAR
541   ILKLDGKDYR PEEQAAFDLL RDGLLDGISN RKSTPKLDVY SDQIVWGRSP VRIDMAGGWT
601   DTPPYSLYSG GNVVNLAIEL NGQPPLQVYV KPCKDFHIVL RSIDMGAMEI VSTFDELQDY
661   KKIGSPFSIP KAALSLAGFA PAFSAVSYAS LEEQLKDEGA GIEVTLLAAI PAGSGLGTSS
721   ILASTVLGAI NDFCGLAWDK NEICQRTLVL EQLLTTGGGW QDQYGGVLQG VKLLQTEAGF
781   AQSPLVRWLP DHLFTHPEYK DCHLLYYTGI TRTAKGILAE IVSSMELNSS LHLNLLSEMK
841   AHALDMNEAI QRGSFVEFGR LVGKTWEQNK ALDSGTNPPA VEAIIDLIKD YTLGYKLPGA
901   GGGGYLYMVA KDPQAAVRIR KILTENAPNP RARFVEMTLS DKGFQVSRS
```

SEQ ID NO: 4. *E. coli* str. K-12 substr. MG1655 LacY (GenBank: AAC73446.1)

```
  1   MYYLKNTNFW MFGLFFFFYF FIMGAYFPFF PIWLHDINHI SKSDTGIIFA AISLESLLFQ
 61   PLFGLLSDKL GLRKYLLWII TGMLVMFAPF FIFIFGPLLQ YNILVGSIVG GIYLGFCENA
121   GAPAVEAFIE KVSRRSNFEF GRARMFGCVG WALCASIVGI MFTINNQFVF WLGSGCALIL
181   AVLLFFAKTD APSSATVANA VGANHSAFSL KLALELFRQP KLWFLSLYVI GVSCTYDVED
241   QQFANFFTSF FATGEQGTRV FGYVTTMGEL LNASIMFFAP LIINRIGGKN ALLLAGTIMS
301   VRIIGSSFAT SALEVVILKT LHMFEVPFLL VGCFKYITSQ FEVRESATIY LVCFCFFKQL
361   AMIFMSVLAG NMYESIGFQG AYLVLGLVAL GFTLISVFTL SGPGPLSLLR RQVNEVA
```

SEQ ID NO: 5. *E. coli* K-12 substr. MG1655 FucP (AAC75843.1)

```
  1   MGNTSIQTQS YRAVDKDAGQ SRSYIIPFAL LCSLFFLWAV ANNLNDILLP QFQQAFTLTN
 61   FQAGLIQSAF YFGYFIIPIP AGILMKKLSY KAGIITGLFL YALGAALFWP AAEIMNYTLE
121   LVGLFIIAAG LGCLETAANP FVTVLGPESS GHERLNLAQT FNSFGAIIAV VFGQSLILSN
181   VPHQSQDVLD KMSPEQLSAY KHSLVLSVQT PYMIIVAIVL LVALLIMLTK FPALQSDNHS
241   DAKQGSFSAS LSRLARIRHW RWAVLAQFCY VGAQTACWSY LIRYAVEEIP GMTAGFAANY
301   LTGTMVCFFI GRFTGTWLIS RFAPHKVLAA YALIAMALCL ISAFAGGHVG LIALTLCSAF
361   MSIQYPTIFS LGIKNLGQDT KYGSSFIVMT IIGGGIVTPV MGFVSDAAGN IPTAELIPAL
421   CFAVIFIFAR FRSQTATN
```

-continued

| V. Informal Sequence Listing |
| --- |

SEQ ID NO: 6. *E. coli* K-12 substr. MG1655 FucU (AAC75846.1)
1 MLKTISPLIS PELLKVLAEM GHGDEIIFSD AHFPAHSMGP QVIRADGLLV SDLLQAIIPL
61 FELDSYAPPL VMMAAVEGDT LDPEVERRYR NALSLQAPCP DIIRINRFAF YERAQKAFAI
121 VITGERAKYG NILLKKGVTP SEQ ID NO: 7. *E. coli* LacZ K-12 substr. MG1655 (AAC73447.1)
1 MTMITDSLAV VLQRRDWENP GVTQLNRLAA HPPFASWRNS EEARTDRPSQ QLRSLNGEWR
61 FAWFPAPEAV PESWLECDLP EADTVVVPSN WQMHGYDAPI YTNVTYPITV NPPFVPTENP
121 TGCYSLTFNV DESWLQEGQT RIIFDGVNSA FHLWCNGRWV GYGQDSRLPS EFDLSAFLRA
181 GENRLAVMVL RWSDGSYLED QDMWRMSGIF RDVSLLHKPT TQISDEHVAT RENDDESRAV
241 LEAEVQMCGE LRDYLRVTVS LWQGETQVAS GTAPFGGEII DERGGYADRV TLRLNVENPK
301 LWSAEIPNLY RAVVELHTAD GTLIEAEACD VGFREVRIEN GLLLLNGKPL LIRGVNRHEH
361 HPLHGQVMDE QTMVQDILLM KQNNENAVRC SHYPNHPLWY TLCDRYGLYV VDEANIETHG
421 MVPMNRLTDD PRWLPAMSER VTRMVQRDRN HPSVIIWSLG NESGHGANHD ALYRWIKSVD
481 PSRPVQYEGG GADTTATDII CPMYARVDED QPFPAVPKWS IKKWLSLPGE TRPLILCEYA
541 HAMGNSLGGF AKYWQAFRQY PRLQGGFVWD WVDQSLIKYD ENGNPWSAYG GDFGDTPNDR
601 QFCMNGLVFA DRTPHPALTE AKHQQQFFQF RLSGQTIEVT SEYLFRHSDN ELLHWMVALD
661 GKPLASGEVP LDVAPQGKQL IELPELPQPE SAGQLWLTVR VVQPNATAWS EAGHISAWQQ
721 WRLAENLSVT LPAASHAIPH LTTSEMDFCI ELGNKRWQFN RQSGFLSQMW IGDKKQLLTP
781 LRDQFTRAPL DNDIGVSEAT RIDPNAWVER WKAAGHYQAE AALLQCTADT LADAVLITTA
841 HAWQHQGKTL FISRKTYRID GSGQMAITVD VEVASDTPHP ARIGLNCQLA QVAERVNWLG
901 LGPQENYPDR LTAACFDRWD LPLSDMYTPY VFPSENGLRC GTRELNYGPH QWRGDFQFNI
961 SRYSQQQLME TSHRHLLHAE EGTWLNIDGF HMGIGGDDSW SPSVSAEFQL SAGRYHYQLV
1021 WCQK SEQ ID NO: 8. *H. mustelae* 12198 α1-2-fucosyltransferase (Hm2FT) (GenBank: CBG40460),
1 MDFKIVQVHG GLGNQMFQYA FAKSLQTHLN IPVLLDTTWF DYGNRELGLH LEPIDLQCAS
61 AQQIAAAHMQ NLPRLVRGAL RRMGLGRVSK EIVFEYMPEL FEPSRIAYFH GYFQDPRYFE
121 DISPLIKQTF TLPHPTEHAE QYSRKLSQIL AAKNSVFVHI RRGDYMRLGW QLDISYQLRA
181 IAYMAKRVQN LELFLFCEDL EFVQNLDLGY PFVDMTTRDG AAHWDMMLMQ SCKHGIITNS
241 TYSWWAAYLI KNPEKIIIGP SHWIYGNENI LCKDWVKIES QFETKS SEQ ID NO: 9. *E. coli* 0128:B12 α1-2-fucosyltransferase (WbsJ) (GenBank: AA037698.1),
1 MEVKIIGGLG NQMFQYATAF AIAKRTHQNL TVDISDAVKY KTHPLRLVEL SCSSEFVKKA
61 WPFEKYLESE KIPHEMKKGM FRKHYVEKSL EYDPDIDTKS INKKIVGYFQ TEKYFKEFRH
121 ELIKEFQPKT KENSYQNELL NLIKENDTCS LHIRRGDYVS SKIANETHGT CSEKYFERAI
181 DYLMNKGVIN KKTLLFIFSD DIKWCRENIF FNNQICFVQG DAYHVELDML LMSKCKNNII
241 SNSSFSWWAA WLNENKNKTV IAPSKWFKKD IKHDIIPESW VKL SEQ ID NO: 10. *H. pylori* UA1234 α1-2-fucosyltransferase (Hp2FTa) (GenBank: AAD29863.1),
1 MAFKVVQICG GLGNQMFQYA FAKSLQKHSN TPVLLDITSF DWSNRKMQLE LFPIDLPYAS
61 EKEIAIAKMQ HLPKLVRNVL KCMGEDRVSQ EIVFEYEPKL LKTSRLTYFY GYFQDPRYED
121 AISPLIKQTF TLPPPPENGN NKKKEEEYHR KLALILAAKN SVEVHIRRGD YVGIGCQLGI
181 DYQKKALEYM AKRVPNMELF VFCEDLEFTQ NLDLGYPEMD MTTRDKEEEA YWDMLLMQSC
241 KHGIIANSTY SWWAAYLINN PEKIIIGPKH WLFGHENILC KEWVKIESHF EVKSQKYNA SEQ ID NO: 11. *H. pylori* UA802 α1-2-fucosyltransferase (Hp2FTb) (GenBank: AAC99764.1).
1 MAFKVVQICG GLGNQMFQYA FAKSLQKHLN TPVLLDTTSF DWSNRKMQLE LFPIDLPYAN
61 AKEIAIAKMQ HLPKLVRDAL KYIGFDRVSQ EIVFEYEPKL LKPSRLTYFF GYFQDPRYED
121 AISSLIKQTF TLPPPPENNK NNNKKEEEYQ RKLSLILAAK NSVFVHIRRG DYVGIGCQLG
181 IDYQKKALEY MAKRVPNMEL FVFCEDLKFT QNLDLGYPFT DMTTRDKEEE AYWDMLLMQS
241 CKHGIIANST YSWWAAYLME NPEKIIIGPK HWLFGHENIL CKEWVKIESH FEVKSQKYNA SEQ ID NO: 12. *H. pylori* ATCC43504 α1-3-fucosyltransferase (Hp43504 3FT) (GenBank: AAB93985),
1 MPLYYDRLHH KAESVNDTTA PYKIKGNSLY TLKKPSHCFK ENHPNLCALI NNESDPLKRG
61 FASEVASNAN APMRNAFYDA LNSIEPVTGG GAVKNTLGYK VGNKSEFLSQ YKENLCFENS
121 QGYGYVTEKI IDAYFSHTIP IYWGSPSVAK DENPKSFVNV HDENNEDEAI DYVRYLHTHP
181 NAYLDMLYEN PLNTLDGKAY FYQNLSFKKI LDFFKTILEN DTIYHNNPFI FYRDLNEPLV
241 SIDNLRINYD NLRVNYDDLR VNYDDLRVNY DDLRINYDDL RINYDDLRIN YERLLQNASP
301 LLELSQNTSF KIYRKIYQKS LPLLRVIRRW VKK SEQ ID NO: 13. *H.* pylori J99 α1-3-fucosyltransferase (HpJ99 3FT) (GenBank: AAD06169.1),
1 MFQPLLDAYT DSTRLDETDY KPPLNIALAN WWPLDKRESK GFRRFILYFI LSQRYTITLH
61 QNPNEPSDLV FGSPIGSARK ILSYQNTKRV FYTGENEVPN FNLFDYAIGF DELDERDRYL
121 RMPLYYASLH YKAESVNDTT APYKLKDNSL YALKKPSHHF KENHPNLCAV VNDESDPLKR
181 GFASFVASNP NAPIRNAFYD ALNSIEPVTG GGSVKNTLGY NVKNKSEFLS QYKENLCFEN
241 TQGYGYVTEK IIDAYFSHTI PIYWGSPSVA KDENPKSFVN VCDFKNFDEA IDYVRYLHTH
301 PNAYLDMLYE NPLNTLDGKA YFYQNLSFKK ILDFFKTILE NDTIYHDNPF IFYRDLNEPL
361 VAIDDLRVNY DDLRVNYDDL RVNYDDLRVN YDDLRVNYDD LRVNYDDLRV NYDRLLQNAS
420 PLLELSQNTT FKIYRKAYQK SLPLLRTIRR WVKK -continued

| V. Informal Sequence Listing |
| --- |

SEQ ID NO: 14. *H. pylori* J99 α1-3-fucosyltransferase (HpJ99 3FT) (GenBank: AAD06573.1),

```
  1   MFQPLLDAFI ESTPIKKKIT FKSPPPPLKI AVANWWGGAE EFKKSTLYFI LSQRYTITLH
 61   QNPNEPSDLV LGSPIGSARK ILSYQNTKRV FYTGENEVPN FNLFDYAIGF DELDERDRYL
121   RMPLYYASLH YKAESVNDTT APYKLKDNSL YALKKPSHHF KENHPNLCAV VNDESDPLKR
181   GFASEVASNP NAPIRNAFYD ALNSIEPVTG GGSVKNTLGY NVKNKSEFLS QYKENLCFEN
241   TQGYGYVTEK IIDAYFSHTI PIYWGSPSVA KDENPKSFVN VCDFKNFDEA IDYVRYLHTH
301   PNAYLDMLYE NPLNTLDGKA YFYQNLSFKK ILDFFKTILE NDTIYHDNPF IFYRDLNEPL
361   VAIDDLRVNY DDLRVNYDDL RVNYDDLRVN YDRLLQNASP LLELSQNTTF KIYRKAYQKS
421   LPLLRAIRRW VKKLGL
```

SEQ ID NO: 15. *H. pylori* NCTC11637 α1-3-fucosyltransferase (Hp11637 3FT) (GenBank: AAB93985).

```
  1   MPLYYDRLHH KAESVNDTTA PYKIKGNSLY TLKKPSHCFK ENHPNLCALI NNESDPLKRG
 61   FASFVASNAN APMRNAFYDA LNSIEPVTGG GAVKNTLGYK VGNKSEFLSQ YKENLCFENS
121   QGYGYVTEKI IDAYFSHTIP IYWGSPSVAK DENPKSFVNV HDENNEDEAI DYVRYLHTHP
181   NAYLDMLYEN PLNTLDGKAY FYQNLSFKKI LDFFKTILEN DTIYHNNPFI FYRDLNEPLV
241   SIDNLRINYD NLRVNYDDLR VNYDDLRVNY DDLRINYDDL RINYDDLRIN YERLLQNASP
301   LLELSQNTSF KIYRKIYQKS LPLLRVIRRW VKK
```

SEQ ID NO: 16. *B. fragilis* NCTC 9343 α1-3/α1-4-fucosyltransferase (Bf3/4ft) (GenBank: CAH09495.1)

```
  1   MDILILFYNT MWGFPLEFRK EDLPGGCVIT TDRNLIAKAD AVVFHLPDLP SVMEDEIDKR
 61   EGQLWVGWSL ECEENYSWTK DPEFRESEDL WMGYHQEDDI VYPYYGPDYG KMLVTARREK
121   PYKKKACMFI SSDMNRSHRQ EYLKELMQYT DIDSYGKLYR NCELPVEDRG RDTLLSVIGD
181   YQFVISFENA IGKDYVTEKF FNPLLAGTVP VYLGAPNIRE FAPGENCFLD ICTFDSPEGV
241   AAFMNQCYDD EALYERFYAW RKRPLLLSFT NKLEQVRSNP LIRLCQKIHE LKLGGI
```

SEQ ID NO: 17. *H. hepaticus* ATCC 51449 Hh0072 (GenBank: AAP76669.1)

```
  1   MKDDLVILHP DGGIASQIAF VALGLAFEQK GAKVKYDLSW FAEGAKGEWN PSNGYDKVYD
 61   ITWDISKAFP ALHIEIANEE EIERYKSKYL IDNDRVIDYA PPLYCYGYKG RIFHYLYAPF
121   FAQSFAPKEA QDSHTPFAAL LQEIESSPSP CGVHIRRGDL SQPHIVYGNP TSNEYFAKSI
181   ELMCLLHPQS SFYLESDDLA FVKEQIVPLL KGKTYRICDV NNPSQGYLDL YLLSRCRNII
241   GSQGSMGEFA KVLSPHNPLL ITPRYRNIFK EVENVMCVNW GESVQHPPLV CSAPPPLVSQ
301   LKRNAPLNSR LYKEKDNASA
```

SEQ ID NO: 18. *A. thaliana* FKGP (UniProt: Q9LNJ9)

```
  1   MSKQRKKADL ATVLRKSWYH LRLSVRHPTR VPTWDAIVLT AASPEQAELY DWQLRRAKRM
 61   GRIASSTVTL AVPDPDGKRI GSGAATLNAI YALARHYEKL GFDLGPEMEV ANGACKWVRF
121   ISAKHVLMLH AGGDSKRVPW ANPMGKVFLP LPYLAADDPD GPVPLLEDHI LAIASCARQA
181   FQDQGGLFIM TGDVLPCFDA FKMTLPEDAA SIVTVPITLD IASNHGVIVT SKSESLAESY
241   TVSLVNDLLQ KPTVEDLVKK DAILHDGRTL LDTGIISARG RAWSDLVALG CSCQPMILEL
301   IGSKKEMSLY EDLVAAWVPS RHDWLRTRPL GELLVNSLGR QKMYSYCTYD LQFLHFGTSS
361   EVLDHLSGDA SGIVGRRHLC SIPATTVSDI AASSVILSSE IAPGVSIGED SLIYDSTVSG
421   AVQIGSQSIV VGIHIPSEDL GTPESFREML PDRHCLWEVP LVGHKGRVIV YCGLHDNPKN
481   SIHKDGTFCG KPLEKVLFDL GIEESDLWSS YVAQDRCLWN AKLFPILTYS EMLKLASWLM
541   GLDDSRNKEK IKLWRSSQRV SLEELHGSIN FPEMCNGSSN HQADLAGGIA KACMNYGMLG
601   RNLSQLCHEI LQKESLGLEI CKNFLDQCPK FQEQNSKILP KSRAYQVEVD LLRACGDEAK
661   AIELEHKVWG AVAEETASAV RYGFREHLLE SSGKSHSENH ISHPDRVFQP RRTKVELPVR
721   VDFVGGWSDT PPWSLERAGY VLNMAITLEG SLPIGTIIET TNQMGISIQD DAGNELHIED
781   PISIKTPFEV NDPFRLVKSA LLVTGIVQEN FVDSTGLAIK TWANVPRGSG LGTSSILAAA
841   VVKGLLQISN GDESNENIAR LVLVLEQLMG TGGGWQDQIG GLYPGIKFTS SFPGIPMRLQ
901   VVPLLASPQL ISELEQRLLV VFTGQVRLAH QVLHKVVTRY LQRDNLLISS IKRLTELAKS
```

SEQ ID NO: 19. *B. longum* subsp. *infantis* ATCC 15697 FL transporter-1 domain Blon-0341 (ACJ51465.1)

```
  1   MTNATAQPDT SVMRKPKRQY IGILYCLPYV VVFLFGMIVP MFYALYLSFF KQSLLGGTTE
 61   AGFDNFIRAF KDEALWGGFR NVLIYAAIQI PMNLILSLVA ALVLDSQRIR HIAVPRILLF
121   LPYAVPGVIA ALMWGYIYGD KYGLFGQIAG MFGVAAPNML SKQLMLFAIA NICTWCFLGY
181   NMLIYYSALI GIPNDLYESA RIDGASELRI AWSVKIPQIK STIVMTVLES VIGTLQLENE
241   PNILRTSAPD VINSSYTPNI YTYNLAFNGQ NVNYAAAVSL VIGIIVMALV AVVKIIGNKW
301   ENK
```

SEQ ID NO: 20. *B. longum* subsp. *infantis* ATCC 15697 FL transporter-1 domain Blon-0342 (ACJ51466.1)

```
  1   MSEAIARPRS KSLQRRDAKL ALKASKHYKR MQQREPAPKL TGKQRVLNWL LHIIMAVMVI
 61   YCLVPLLWVV FSSTKTSEGI FSSFGLWEDD KNVEWQNVQD TFAYQHGVYT RWLENTIMYA
121   VVAGVGATII ATFAGYAIAT MRFPGRNALL AVTLAFMSIP STVITVPLFL MYSKIGLVGT
181   PWAVIIPQLA TPFGLYLMII YAQTSIPVSL IEAAKLDGAN TWTIFWKVGF PLLSPGFVTV
241   LLFTLVGVWN NYFLPLIMLT NTNDYPLTVG LNMWLKMGAQ GTSDGQVPNN LIITGSLIAV
301   VPLIIAFMFL QKYWQSGLAA GSVKQ
```

SEQ ID NO: 21. *B. longum* subsp. *infantis* ATCC 15697 FL transporter-1 domain Blon-0343 (ACJ51467.1)

```
  1   MTHKGVIMKK SIRLIAAVAA LAMTAGAAAC GSGTSQKNNK ADVSLNDINS ALTDTSKTTD
 61   LTVWAYSAKQ IEGPVKAFQE RYPHIKINFV NTGAASDHFT KFQNVVSANK GVPDVVQMSI
121   SEYEQYAVSG ALLNFESDEI EKAWGTQYAQ AAWKNVHFGG GLYGTPQDAA PLALYVRKDI
```

-continued

| V. Informal Sequence Listing |
| --- |

181 LDEHGLKVPT TWQEFYDEGV KLHKQDPSKY MGFISSSDTS LFGVLRTVGA KPWTVKDTTN
241 IDFSLTTGRV AEFIKFIQKC LDDGVLRAAA TGTDEFNREV NDGVYATRLE GCWQGNIYKD
301 QNPSLKGKMV VAHPLAWGND GESYQSESTG SMFSVSSATP KDKQAAALAF IQWVNGSKDG
361 VSEFLTANKG NYFMASNYYQ KDKSKRDQQE TDGYFANTNV NEIYFESMDK VNMDWDYIPF
421 PAQLTVAFGD TVAPALTGKG DLLTAFTKLQ DNLKSYAEDN GFKVTTDAD

SEQ ID NO: 22. *B. longum* subsp. *infantis* ATCC 15697 FL transporter-2 domain Blon-2202 (ACJ51465.1)
1 MKKSIRLVAA IAALAMTAGI SACGSSTNGN QAKSDVTAQD VENALTDTSK NVELTVWAYS
61 AKQMEPTVKA FEKKYPHIKI NFVNTGAAED HFTKFQNVVQ AQKDIPDVVQ MSANKFQQFA
121 VSGALLNFAN DSIEKAWSKL YTKTAWAQVH YAGGLYGAPQ DATPLANYVR KDILDEHNLQ
181 VPESWEDIYN EGIKLHKEDS NKYMGILGSD ISFFTNLYRS VGARLWKVNS VDDVELTMNS
241 GKAKEFTEFL QKCLKDGVLE GGTVFTDEFN RSINDGRYAT FINENWMGNT YKEQNPSLKG
301 KMVVAAPPSW KGQPYQSSSV GSMMSVSAAC PKEKQAAALA FINWLDSDKD AIQSWQDTNN
361 GNFFMAASVY QDDENQRNKK ETDGYYANDD VNAVYFDSMD KVNTDWEYLP FMSQVEVVEN
421 DVIVPEMNEN GDLVGAMAKA QQKLKAYAED NGFKVTTDAD SEQ ID NO: 23. *B. longum* subsp. *infantis* ATCC 15697 FL transporter-2 domain Blon-2203 (ACJ53263.1)
1 MSEAIARPRS KSLQRRDAKL ALKASKHYKR MQQREPAPKL TGKQRVLNWL LHIIMAVMVI
61 YCLVPLLWVV FSSTKTSEGI FSSFGLWEDD KNVFWQNVQD TFAYQHGVYT RWLENTIMYA
121 VVAGVGATII ATFAGYAIAT MRFPGRNALL AVTLAFMSIP STVITVPLEL MYSKIGLVGT
181 PWAVIIPQLA TPFGLYLMII YAQTSIPVSL IEAAKLDGAN TWTIFWKVGF PLLSPGFVTV
241 LLFTLVGVWN NYFLPLIMLT NTNDYPLTVG LNMWLKMGAQ GTSDGQVPNN LIITGSLIAV
301 VPLIIAFMFL QKYWQSGLAA GSVKQ SEQ ID NO: 24. *B. longum* subsp. *infantis* ATCC 15697 FL transporter-2 domain Blon-2204 (ACJ53264.1)
1 MTNATAQPDT SVMRKPKRQY IGILYCLPYV VVFLFGMIVP MFYALYLSFF KQSLLGGTTF
61 AGFDNFIRAF KDEALWGGFR NVLIYAAIQI PMNLILSLVA ALVLDSQRIR HIAVPRILLE
121 LPYAVPGVIA ALMWGYIYGD KYGLFGQIAG MFGVAAPNML SKQLMLFAIA NICTWCFLGY
181 NMLIYYSALI GIPNDLYESA RIDGASELRI AWSVKIPQIK STIVMTVLES VIGTLQLENE
241 PNILRTSAPD VINSSYTPNI YTYNLAFNGQ NVNYAAAVSL VIGIIVMALV AVVKIIGNKW
301 ENK SEQ ID NO: 25. *B. subtilus* FucU homolog (WP_158321581.1)
1 MLKGIPAILS PDLMKVLMEM GHGDEIVLAD GNFPSASHAQ NLLRCDGHGI PALLEAILKE
61 FPLDTYVEHP VTLMDVVEGE QFQPTIWQDF EKVIQKEHGP ALQMEYLDRF TFYERAKKAY
121 AIVATGEAAQ YANIILKKGV VK SEQ ID NO: 26. *B. subtilus* LacZ homolog (MBA5241670.1)
1 MEVTDVRLRV DRENPGVTQL NRLAAHPPFA SWRNSEEART DRPSQQLRSL NGEWRFAWFP
61 APEAVPESWL ECDLPEADTV VVPSNWQMHG YDAPIYTNVT YPITVNPPFV PTENPTGCYS
121 LTFNVDESWL QEGQTRIIFD GVNSAFHLWC NGRWVGYGQD SRLPSEFDLS AFLRAGENRL
181 AVMVLRWSDG SYLEDQDMWR MSGIFRDVSL LHKPTTQISD FHVATRENDD FSRAVLEAEV
241 QMCGELRDYL RVTVSLWQGE TQVASGTAPF GGEIIDERGG YADRVTLRLN VENPKLWSAE
301 IPNLYRAVVE LHTADGTLIE AEACDVGFRE VRIENGLLLL NGKPLLIRGV NRHEHHPLHG
361 QVMDEQTMVQ DILLMKQNNF NAVRCSHYPN HPLWYTLCDR YGLYVVDEAN IETHGMVPMN
421 RLTDDPRWLP AMSERVTRMV QRDRNHPSVI IWSLGNESGH GANHDALYRW IKSVDPSRPV
481 QYEGGGADTT ATDIICPMYA RVDEDQPFPA VPKWSIKKWL SLPGETRPLI LCEYAHAMGN
541 SLGGFAKYWQ AFRQYPRLQG GFVWDWVDQS LIKYDENGNP WSAYGGDFGD TPNDRQFCMN
601 GLVFADRTPH PALTEAKHQQ QFFQFRLSGQ TIEVTSEYLF RHSDNELLHW MVALDGKPLA
661 SGEVPLDVAP QGKQLIELPE LPQPESAGQL WLTVRVVQPN ATAWSEAGHI SAWQQWRLAE
721 NLSVTLPAAS HAIPHLTTSE MDFCIELGNK RWQFNRQSGF LSQMWIGDKK QLLTPLRDQF
781 TRAPLDNDIG VSEATRIDPN AWVERWKAAG HYQAEAALLQ CTADTLADAV LITTAHAWQH
841 QGKTLFISRK TYRIDGSGQM AITVDVEVAS DTPHPARIGL NCQLAQVAER VNWLGLGPQE
901 NYPDRLTAAC FDRWDLPLSD MYTPYVEPSE NGLRCGTREL NYGPHQWRGD FQFNISRYSQ
961 QQLMETSHRH LLHAEEGTWL NIDGFHMGIG GDDSWSPSVS AELQLSAGRY HYQLVWCQK

What is claimed is:

1. A method for producing a tetrasaccharide lactodifucotetraose (LDFT) product, the method comprising culturing a recombinant cell in a cell culture medium comprising L-fucose, lactose, and glycerol, wherein the recombinant cell comprises
- a polynucleotide encoding an 1-2-fucosyltransferase polypeptide,
- a polynucleotide encoding an α1-3-fucosyltransferase polypeptide,
- a polynucleotide encoding a nucleotide sugar pyrophosphorylase polypeptide,
- a polynucleotide encoding a lactose transporter polypeptide, and
- a polynucleotide encoding an L-fucose transporter polypeptide, wherein the cell is cultured under conditions in which the α1-2-fucosyltransferase polypeptide and the α1-3-fucosyltransferase polypeptide are expressed, wherein the cell culture media does not comprise glucose, wherein the recombinant cell is modified to eliminate or reduce expression of an L-fucose mutarotase, and wherein the recombinant cell is modified to eliminate or reduce expression of a β-galactosidase.

2. The method claim 1, wherein the α1-2-fucosyltransferase polypeptide is an *E. coli* O126 α1-2-fucosyltransferase WbgL polypeptide.

3. The method claim 1, wherein the α1-3-fucosyltransferase polypeptide is a truncated α1-3-fucosyltransferase polypeptide.

4. The method claim 1, wherein the α1-3-fucosyltransferase polypeptide is an *H. pylori* UA948 α1-3/4-fucosyltransferase (Hp3/4 FT) polypeptide.

5. The method claim 1, wherein the nucleotide sugar pyrophosphorylase polypeptide is a *B. fragilis* bifunctional L-fucokinase/GDP-L-fucose pyrophosphorylase (Fkp) polypeptide.

6. The method claim 1, wherein the lactose transporter polypeptide is an *E. coli* LacY polypeptide.

7. The method claim 1, wherein the L-fucose transporter polypeptide is an *E. coli* FucP polypeptide.

8. The method claim 1, wherein the L-fucose mutarotase is *E. coli* fucU.

9. The method claim 1, wherein the β-galactosidase is *E. coli* LacZ.

10. The method claim 1, further comprising an polynucleotide encoding an additional transporter polypeptide.

11. The method claim 10, wherein the additional transporter polypeptide is a *Bifidobacterium* fucosyllactose transporter polypeptide.

12. The method claim 1, wherein the recombinant cell is an *E. coli* cell, a *B. subtilis* cell, a *C. glutamicum* cell, or an *S. cerevisiae* cell.

13. The method of claim 1, wherein expression of the α1-2-fucosyltransferase polypeptide is induced at a level corresponding to 30-40% of maximum, and wherein expression of the α1-3-fucosyltransferase polypeptide is induced at a maximum level.

* * * * *

SEQUENCE LISTING

Sequence total quantity: 133
SEQ ID NO: 1 moltype = AA length = 297
FEATURE Location/Qualifiers
source 1..297
mol_type = protein
organism = Escherichia coli
SEQUENCE: 1
MSIIRLQGGL GNQLFQFSFG YALSKINGTP LYFDISHYAE NDDHGGYRLN NLQIPEEYLQ 60
YYTPKINNIY KLLVRGSRLY PDIFLFLGFC NEFHAYGYDF EYIAQKWKSK KYIGYWQSEH 120
FFHKHILDLK EFFIPKNVSE QANLLAAKIL ESQSSLSIHI RRGDYIKNKT ATLTHGVCSL 180
EYYKKALNKI RDLAMIRDVF IFSDDIFWCK ENIETLLSKK YNIYYSEDLS QEEDLWLMSL 240
ANHHIIANSS FSWWGAYLGS SASQIVIYPT PWYDITPKNT YIPIVNHWIN VDKHSSC 297

```
SEQ ID NO: 2            moltype = AA  length = 462
FEATURE                 Location/Qualifiers
source                  1..462
                        mol_type = protein
                        organism = Helicobacter pylori
SEQUENCE: 2
MFQPLLDAFI DSTHLDETTH KPPLNVALAN WWPLKNSEKK GFRDFILHFI LKQRYKIILH  60
SNPNEPSDLV FGNPLEQARK ILSYQNTKRV FYTGENEVPN FNLFDYAIGF DELDFNDRYL  120
RMPLYYAYLH YKAMLVNDTT SPYKLKALYT LKKPSHKFKE NHPNLCALIH NESDPWKRGF  180
ASFVASNPNA PIRNAFYDAL NAIEPVASGG SVKNTLGYKV KNKNEFLSQY KFNLCFENSQ  240
GYGYVTEKIL DAYFSHTIPI YWGSPSVAKD FNPKSFVNVH DFNNFDEAID YIRYLHAHQN  300
AYLDMLYENP LNTIDGKAGF YQDLSFEKIL DFFKNILEND TIYHCNDAHY SALHRDLNEP  360
LVSVDDLRRD HDDLRVNYDD LRVNYDDLRV NYDDLRVNYD DLRVNYDDLR RDHDDLRRDH  420
ERLLSKATPL LELSQNTSFK IYRKAYQKSL PLLRAIRRWV RK                    462

SEQ ID NO: 3            moltype = AA  length = 949
FEATURE                 Location/Qualifiers
source                  1..949
                        mol_type = protein
                        organism = Bacteroides fragilis
SEQUENCE: 3
MQKLLSLPSN LVQSFHELER VNRTDWFCTS DPVGKKLGSG GGTSWLLEEC YNEYSDGATF  60
GEWLEKEKRI LLHAGGQSRR LPGYAPSGKI LTPVPVFRWE RGQHLGQNLL SLQLPLYEKI  120
MSLAPDKLHT LIASGDVYIR SEKPLQSIPE ADVVCYGLWV DPSLATHHGV FASDRKHPEQ  180
LDFMLQKPSL AELESLSKTH LFLMDIGIWL LSDRAVEILM KRSHKESSEE LKYYDLYSDF  240
GLALGTHPRI EDEEVNTLSV AILPLPGGEF YHYGTSKELI SSTLSVQNKV YDQRRIMHRK  300
VKPNPAMFVQ NAVVRIPLCA ENADLWIENS HIGPKWKIAS RHIITGVPEN DWSLAVPAGV  360
CVDVVPMGDK GFVARPYGLD DVFKGDLRDS KTTLTGIPFG EWMSKRGLSY TDLKGRTDDL  420
QAVSVFPMVN SVEELGLVLR WMLSEPELEE GKNIWLRSEH FSADEISAGA NLKRLYAQRE  480
EFRKGNWKAL AVNHEKSVFY QLDLADAAED FVRLGLDMPE LLPEDALQMS RIHNRMLRAR  540
ILKLDGKDYR PEEQAAFDLL RDGLLDGISN RKSTPKLDVY SDQIVWGRSP VRIDMAGGWT  600
DTPPYSLYSG GNVVNLAIEL NGQPPLQVYV KPCKDFHIVL RSIDMGAMEI VSTFDELQDY  660
KKIGSPFSIP KAALSLAGFA PAFSAVSYAS LEEQLKDFGA GIEVTLLAAI PAGSGLGTSS  720
ILASTVLGAI NDFCGLAWDK NEICQRTLVL EQLLTTGGGW QDQYGGVLQG VKLLQTEAGF  780
AQSPLVRWLP DHLFTHPEYK DCHLLYYTGI TRTAKGILAE IVSSMFLNSS LHLNLLSEMK  840
AHALDMNEAI QRGSFVEFGR LVGKTWEQNK ALDSGTNPPA VEAIIDLIKD YTLGYKLPGA  900
GGGGYLYMVA KDPQAAVRIR KILTENAPNP RARFVEMTLS DKGFQVSRS             949

SEQ ID NO: 4            moltype = AA  length = 417
FEATURE                 Location/Qualifiers
source                  1..417
                        mol_type = protein
                        organism = Escherichia coli
SEQUENCE: 4
MYYLKNTNFW MFGLFFFFYF FIMGAYFPFF PIWLHDINHI SKSDTGIIFA AISLFSLLFQ  60
PLFGLLSDKL GLRKYLLWII TGMLVMFAPF FIFIFGPLLQ YNILVGSIVG GIYLGFCFNA  120
GAPAVEAFIE KVSRRSNFEF GRARMFGCVG WALCASIVGI MFTINNQFVF WLGSGCALIL  180
AVLLFFAKTD APSSATVANA VGANHSAFSL KLALELFRQP KLWFLSLYVI GVSCTYDVFD  240
QQFANFFTSF FATGEQGTRV FGYVTTMGEL LNASIMFFAP LIINRIGGKN ALLLAGTIMS  300
VRIIGSSFAT SALEVVILKT LHMFEVPFLL VGCFKYITSQ FEVRFSATIY LVCFCFFKQL  360
AMIFMSVLAG NMYESIGFQG AYLVLGLVAL GFTLISVFTL SGPGPLSLLR RQVNEVA     417

SEQ ID NO: 5            moltype = AA  length = 438
FEATURE                 Location/Qualifiers
source                  1..438
                        mol_type = protein
                        organism = Escherichia coli
SEQUENCE: 5
MGNTSIQTQS YRAVDKDAGQ SRSYIIPFAL LCSLFFLWAV ANNLNDILLP QFQQAFTLTN  60
FQAGLIQSAF YFGYFIIPIP AGILMKKLSY KAGIITGLFL YALGAALFWP AAEIMNYTLF  120
LVGLFIIAAG LGCLETAANP FVTVLGPESS GHFRLNLAQT FNSFGAIIAV VFGQSLILSN  180
VPHQSQDVLD KMSPEQLSAY KHSLVLSVQT PYMIIVAIVL LVALLIMLTK FPALQSDNHS  240
DAKQGSFSAS LSRLARIRHW RWAVLAQFCY VGAQTACWSY LIRYAVEEIP GMTAGFAANY  300
LTGTMVCFFI GRFTGTWLIS RFAPHKVLAA YALIAMALCL ISAFAGGHVG LIALTLCSAF  360
MSIQYPTIFS LGIKNLGQDT KYGSSFIVMT IIGGGIVTPV MGFVSDAAGN IPTAELIPAL  420
CFAVIFIFAR FRSQTATN                                               438

SEQ ID NO: 6            moltype = AA  length = 140
FEATURE                 Location/Qualifiers
source                  1..140
                        mol_type = protein
                        organism = Escherichia coli
SEQUENCE: 6
MLKTISPLIS PELLKVLAEM GHGDEIIFSD AHFPAHSMGP QVIRADGLLV SDLLQAIIPL  60
FELDSYAPPL VMMAAVEGDT LDPEVERRYR NALSLQAPCP DIIRINRFAF YERAQKAFAI  120
VITGERAKYG NILLKKGVTP                                             140

SEQ ID NO: 7            moltype = AA  length = 1024
```

```
FEATURE                Location/Qualifiers
source                 1..1024
                       mol_type = protein
                       organism = Escherichia coli
SEQUENCE: 7
MTMITDSLAV VLQRRDWENP GVTQLNRLAA HPPFASWRNS EEARTDRPSQ QLRSLNGEWR  60
FAWFPAPEAV PESWLECDLP EADTVVVPSN WQMHGYDAPI YTNVTYPITV NPPFVPTENP  120
TGCYSLTFNV DESWLQEGQT RIIFDGVNSA FHLWCNGRWV GYGQDSRLPS EFDLSAFLRA  180
GENRLAVMVL RWSDGSYLED QDMWRMSGIF RDVSLLHKPT TQISDFHVAT RFNDDFSRAV  240
LEAEVQMCGE LRDYLRVTVS LWQGETQVAS GTAPFGGEII DERGGYADRV TLRLNVENPK  300
LWSAEIPNLY RAVVELHTAD GTLIEAEACD VGFREVRIEN GLLLLNGKPL LIRGVNRHEH  360
HPLHGQVMDE QTMVQDILLM KQNNFNAVRC SHYPNHPLWY TLCDRYGLYV VDEANIETHG  420
MVPMNRLTDD PRWLPAMSER VTRMVQRDRN HPSVIIWSLG NESGHGANHD ALYRWIKSVD  480
PSRPVQYEGG GADTTATDII CPMYARVDED QPFPAVPKWS IKKWLSLPGE TRPLILCEYA  540
HAMGNSLGGF AKYWQAFRQY PRLQGGFVWD WVDQSLIKYD ENGNPWSAYG GDFGDTPNDR  600
QFCMNGLVFA DRTPHPALTE AKHQQQFFQF RLSGQTIEVT SEYLFRHSDN ELLHWMVALD  660
GKPLASGEVP LDVAPQGKQL IELPELPQPE SAGQLWLTVR VVQPNATAWS EAGHISAWQQ  720
WRLAENLSVT LPAASHAIPH LTTSEMDFCI ELGNKRWQFN RQSGFLSQMW IGDKKQLLTP  780
LRDQFTRAPL DNDIGVSEAT RIDPNAWVER WKAAGHYQAE AALLQCTADT LADAVLITTA  840
HAWQHQGKTL FISRKTYRID GSGQMAITVD VEVASDTPHP ARIGLNCQLA QVAERVNWLG  900
LGPQENYPDR LTAACFDRWD LPLSDMYTPY VFPSENGLRC GTRELNYGPH QWRGDFQFNI  960
SRYSQQQLME TSHRHLLHAE EGTWLNIDGF HMGIGGDDSW SPSVSAEFQL SAGRYHYQLV  1020
WCQK                                                              1024

SEQ ID NO: 8           moltype = AA  length = 286
FEATURE                Location/Qualifiers
source                 1..286
                       mol_type = protein
                       organism = Helicobacter mustelae
SEQUENCE: 8
MDFKIVQVHG GLGNQMFQYA FAKSLQTHLN IPVLLDTTWF DYGNRELGLH LFPIDLQCAS  60
AQQIAAAHMQ NLPRLVRGAL RRMGLGRVSK EIVFEYMPEL FEPSRIAYFH GYFQDPRYFE  120
DISPLIKQTF TLPHPTEHAE QYSRKLSQIL AAKNSVFVHI RRGDYMRLGW QLDISYQLRA  180
IAYMAKRVQN LELFLFCEDL EFVQNLDLGY PFVDMTTRDG AAHWDMMLMQ SCKHGIITNS  240
TYSWWAAYLI KNPEKIIIGP SHWIYGNENI LCKDWVKIES QFETKS                286

SEQ ID NO: 9           moltype = AA  length = 283
FEATURE                Location/Qualifiers
source                 1..283
                       mol_type = protein
                       organism = Escherichia coli
SEQUENCE: 9
MEVKIIGGLG NQMFQYATAF AIAKRTHQNL TVDISDAVKY KTHPLRLVEL SCSSEFVKKA  60
WPFEKYLFSE KIPHFMKKGM FRKHYVEKSL EYDPDIDTKS INKKIVGYFQ TEKYFKEFRH  120
ELIKEFQPKT KFNSYQNELL NLIKENDTCS LHIRRGDYVS SKIANETHGT CSEKYFERAI  180
DYLMNKGVIN KKTLLFIFSD DIKWCRENIF FNNQICFVQG DAYHVELDML LMSKCKNNII  240
SNSSFSWWAA WLNENKNKTV IAPSKWFKKD IKHDIIPESW VKL                   283

SEQ ID NO: 10          moltype = AA  length = 299
FEATURE                Location/Qualifiers
source                 1..299
                       mol_type = protein
                       organism = Helicobacter pylori
SEQUENCE: 10
MAFKVVQICG GLGNQMFQYA FAKSLQKHSN TPVLLDITSF DWSNRKMQLE LFPIDLPYAS  60
EKEIAIAKMQ HLPKLVRNVL KCMGFDRVSQ EIVFEYEPKL LKTSRLTYFY GYFQDPRYFD  120
AISPLIKQTF TLPPPPENGN NKKKEEEYHR KLALILAAKN SVFVHIRRGD YVGIGCQLGI  180
DYQKKALEYM AKRVPNMELF VFCEDLEFTQ NLDLGYPFMD MTTRDKEEEA YWDMLLMQSC  240
KHGIIANSTY SWWAAYLINN PEKIIIGPKH WLFGHENILC KEWVKIESHF EVKSQKYNA   299

SEQ ID NO: 11          moltype = AA  length = 300
FEATURE                Location/Qualifiers
source                 1..300
                       mol_type = protein
                       organism = Helicobacter pylori
SEQUENCE: 11
MAFKVVQICG GLGNQMFQYA FAKSLQKHLN TPVLLDTTSF DWSNRKMQLE LFPIDLPYAN  60
AKEIAIAKMQ HLPKLVRDAL KYIGFDRVSQ EIVFEYEPKL LKPSRLTYFF GYFQDPRYFD  120
AISSLIKQTF TLPPPPENNK NNNKKEEEYQ RKLSLILAAK NSVFVHIRRG DYVGIGCQLG  180
IDYQKKALEY MAKRVPNMEL FVFCEDLKFT QNLDLGYPFT DMTTRDKEEE AYWDMLLMQS  240
CKHGIIANST YSWWAAYLME NPEKIIIGPK HWLFGHENIL CKEWVKIESH FEVKSQKYNA  300

SEQ ID NO: 12          moltype = AA  length = 333
FEATURE                Location/Qualifiers
source                 1..333
                       mol_type = protein
                       organism = Helicobacter pylori
SEQUENCE: 12
MPLYYDRLHH KAESVNDTTA PYKIKGNSLY TLKKPSHCFK ENHPNLCALI NNESDPLKRG  60
```

```
FASFVASNAN APMRNAFYDA LNSIEPVTGG GAVKNTLGYK VGNKSEFLSQ YKFNLCFENS  120
QGYGYVTEKI IDAYFSHTIP IYWGSPSVAK DFNPKSFVNV HDFNNFDEAI DYVRYLHTHP  180
NAYLDMLYEN PLNTLDGKAY FYQNLSFKKI LDFFKTILEN DTIYHNNPFI FYRDLNEPLV  240
SIDNLRINYD NLRVNYDDLR VNYDDLRVNY DDLRINYDDL RINYDDLRIN YERLLQNASP  300
LLELSQNTSF KIYRKIYQKS LPLLRVIRRW VKK                                333

SEQ ID NO: 13          moltype = AA  length = 454
FEATURE                Location/Qualifiers
source                 1..454
                       mol_type = protein
                       organism = Helicobacter pylori
SEQUENCE: 13
MFQPLLDAYT DSTRLDETDY KPPLNIALAN WWPLDKRESK GFRRFILYFI LSQRYTITLH  60
QNPNEPSDLV FGSPIGSARK ILSYQNTKRV FYTGENEVPN FNLFDYAIGF DELDFRDRYL  120
RMPLYYASLH YKAESVNDTT APYKLKDNSL YALKKPSHHF KENHPNLCAV VNDESDPLKR  180
GFASFVASNP NAPIRNAFYD ALNSIEPVTG GGSVKNTLGY NVKNKSEFLS QYKFNLCFEN  240
TQGYGYVTEK IIDAYFSHTI PIYWGSPSVA KDFNPKSFVN VCDFKNFDEA IDYVRYLHTH  300
PNAYLDMLYE NPLNTLDGKA YFYQNLSFKK ILDFFKTILE NDTIYHDNPF IFYRDLNEPL  360
VAIDDLRVNY DDLRVNYDDL RVNYDDLRVN YDDLRVNYDD LRVNYDDLRV NYDRLLQNAS  420
PLLELSQNTT FKIYRKAYQK SLPLLRTIRR WVKK                               454

SEQ ID NO: 14          moltype = AA  length = 436
FEATURE                Location/Qualifiers
source                 1..436
                       mol_type = protein
                       organism = Helicobacter pylori
SEQUENCE: 14
MFQPLLDAFI ESTPIKKKIT FKSPPPPLKI AVANWWGGAE EFKKSTLYFI LSQRYTITLH  60
QNPNEPSDLV LGSPIGSARK ILSYQNTKRV FYTGENEVPN FNLFDYAIGF DELDFRDRYL  120
RMPLYYASLH YKAESVNDTT APYKLKDNSL YALKKPSHHF KENHPNLCAV VNDESDPLKR  180
GFASFVASNP NAPIRNAFYD ALNSIEPVTG GGSVKNTLGY NVKNKSEFLS QYKFNLCFEN  240
TQGYGYVTEK IIDAYFSHTI PIYWGSPSVA KDFNPKSFVN VCDFKNFDEA IDYVRYLHTH  300
PNAYLDMLYE NPLNTLDGKA YFYQNLSFKK ILDFFKTILE NDTIYHDNPF IFYRDLNEPL  360
VAIDDLRVNY DDLRVNYDDL RVNYDDLRVN YDRLLQNASP LLELSQNTTF KIYRKAYQKS  420
LPLLRAIRRW VKKLGL                                                   436

SEQ ID NO: 15          moltype = AA  length = 333
FEATURE                Location/Qualifiers
source                 1..333
                       mol_type = protein
                       organism = Helicobacter pylori
SEQUENCE: 15
MPLYYDRLHH KAESVNDTTA PYKIKGNSLY TLKKPSHCFK ENHPNLCALI NNESDPLKRG  60
FASFVASNAN APMRNAFYDA LNSIEPVTGG GAVKNTLGYK VGNKSEFLSQ YKFNLCFENS  120
QGYGYVTEKI IDAYFSHTIP IYWGSPSVAK DFNPKSFVNV HDFNNFDEAI DYVRYLHTHP  180
NAYLDMLYEN PLNTLDGKAY FYQNLSFKKI LDFFKTILEN DTIYHNNPFI FYRDLNEPLV  240
SIDNLRINYD NLRVNYDDLR VNYDDLRVNY DDLRINYDDL RINYDDLRIN YERLLQNASP  300
LLELSQNTSF KIYRKIYQKS LPLLRVIRRW VKK                                333

SEQ ID NO: 16          moltype = AA  length = 296
FEATURE                Location/Qualifiers
source                 1..296
                       mol_type = protein
                       organism = Bacteroides fragilis
SEQUENCE: 16
MDILILFYNT MWGFPLEFRK EDLPGGCVIT TDRNLIAKAD AVVFHLPDLP SVMEDEIDKR  60
EGQLWVGWSL ECEENYSWTK DPEFRESFDL WMGYHQEDDI VYPYYGPDYG KMLVTARREK  120
PYKKKACMFI SSDMNRSHRQ EYLKELMQYT DIDSYGKLYR NCELPVEDRG RDTLLSVIGD  180
YQFVISFENA IGKDYVTEKF FNPLLAGTVP VYLGAPNIRE FAPGENCFLD ICTFDSPEGV  240
AAFMNQCYDD EALYERFYAW RKRPLLLSFT NKLEQVRSNP LIRLCQKIHE LKLGGI       296

SEQ ID NO: 17          moltype = AA  length = 320
FEATURE                Location/Qualifiers
source                 1..320
                       mol_type = protein
                       organism = Helicobacter hepaticus
SEQUENCE: 17
MKDDLVILHP DGGIASQIAF VALGLAFEQK GAKVKYDLSW FAEGAKGFWN PSNGYDKVYD  60
ITWDISKAFP ALHIEIANEE EIERYKSKYL IDNDRVIDYA PPLYCYGYKG RIFHYLYAPF  120
FAQSFAPKEA QDSHTPFAAL LQEIESSPSP CGVHIRRGDL SQPHIVYGNP TSNEYFAKSI  180
ELMCLLHPQS SFYLFSDDLA FVKEQIVPLL KGKTYRICDV NNPSQGYLDL YLLSRCRNII  240
GSQGSMGEFA KVLSPHNPLL ITPRYRNIFK EVENVMCVNW GESVQHPPLV CSAPPPLVSQ  300
LKRNAPLNSR LYKEKDNASA                                               320

SEQ ID NO: 18          moltype = AA  length = 1055
FEATURE                Location/Qualifiers
source                 1..1055
                       mol_type = protein
                       organism = Arabidopsis thaliana
```

-continued

```
SEQUENCE: 18
MSKQRKKADL ATVLRKSWYH LRLSVRHPTR VPTWDAIVLT AASPEQAELY DWQLRRAKRM  60
GRIASSTVTL AVPDPDGKRI GSGAATLNAI YALARHYEKL GFDLGPEMEV ANGACKWVRF  120
ISAKHVLMLH AGGDSKRVPW ANPMGKVFLP LPYLAADDPD GPVPLLFDHI LAIASCARQA  180
FQDQGGLFIM TGDVLPCFDA FKMTLPEDAA SIVTVPITLD IASNHGVIVT SKSESLAESY  240
TVSLVNDLLQ KPTVEDLVKK DAILHDGRTL LDTGIISARG RAWSDLVALG CSCQPMILEL  300
IGSKKEMSLY EDLVAAWVPS RHDWLRTRPL GELLVNSLGR QKMYSYCTYD LQFLHFGTSS  360
EVLDHLSGDA SGIVGRRHLC SIPATTVSDI AASSVILSSE IAPGVSIGED SLIYDSTVSG  420
AVQIGSQSIV VGIHIPSEDL GTPESFRFML PDRHCLWEVP LVGHKGRVIV YCGLHDNPKN  480
SIHKDGTFCG KPLEKVLFDL GIEESDLWSS YVAQDRCLWN AKLFPILTYS EMLKLASWLM  540
GLDDSRNKEK IKLWRSSQRV SLEELHGSIN FPEMCNGSSN HQADLAGGIA KACMNYGMLG  600
RNLSQLCHEI LQKESLGLEI CKNFLDQCPK FQEQNSKILP KSRAYQVEVD LLRACGDEAK  660
AIELEHKVWG AVAEETASAV RYGFREHLLE SSGKSHSENH ISHPDRVFQP RRTKVELPVR  720
VDFVGGWSDT PPWSLERAGY VLNMAITLEG SLPIGTTIET TNQMGISIQD DAGNELHIED  780
PISIKTPFEV NDPFRLVKSA LLVTGIVQEN FVDSTGLAIK TWANVPRGSG LGTSSILAAA  840
VVKGLLQISN GDESNENIAR LVLVLEQLMG TGGGWQDQIG GLYPGIKFTS SFPGIPMRLQ  900
VVPLLASPQL ISELEQRLLV VFTGQVRLAH QVLHKVVTRY LQRDNLLISS IKRLTELAKS  960
GREALMNCEV DEVGDIMSEA WRLHQELDPY CSNEFVDKLF EFSQPYSSGF KLVGAGGGGF  1020
SLILAKDAEK AKELRQRLEE HAEFDVKVYN WSICI                            1055

SEQ ID NO: 19          moltype = AA  length = 303
FEATURE                Location/Qualifiers
source                 1..303
                       mol_type = protein
                       organism = Bifidobacterium longum
SEQUENCE: 19
MTNATAQPDT SVMRKPKRQY IGILYCLPYV VVFLFGMIVP MFYALYLSFF KQSLLGGTTF  60
AGFDNFIRAF KDEALWGGFR NVLIYAAIQI PMNLILSLVA ALVLDSQRIR HIAVPRILLF  120
LPYAVPGVIA ALMWGYIYGD KYGLFGQIAG MFGVAAPNML SKQLMLFAIA NICTWCFLGY  180
NMLIYYSALI GIPNDLYESA RIDGASELRI AWSVKIPQIK STIVMTVLFS VIGTLQLFNE  240
PNILRTSAPD VINSSYTPNI YTYNLAFNGQ NVNYAAAVSL VIGIIVMALV AVVKIIGNKW  300
ENK                                                               303

SEQ ID NO: 20          moltype = AA  length = 325
FEATURE                Location/Qualifiers
source                 1..325
                       mol_type = protein
                       organism = Bifidobacterium longum
SEQUENCE: 20
MSEAIARPRS KSLQRRDAKL ALKASKHYKR MQQREPAPKL TGKQRVLNWL LHIIMAVMVI  60
YCLVPLLWVV FSSTKTSEGI FSSFGLWFDD KNVFWQNVQD TFAYQHGVYT RWLFNTIMYA  120
VVAGVGATII ATFAGYAIAT MRFPGRNALL AVTLAFMSIP STVITVPLFL MYSKIGLVGT  180
PWAVIIPQLA TPFGLYLMII YAQTSIPVSL IEAAKLDGAN TWTIFWKVGF PLLSPGFVTV  240
LLFTLVGVWN NYFLPLIMLT NTNDYPLTVG LNMWLKMGAQ GTSDGQVPNN LIITGSLIAV  300
VPLIIAFMFL QKYWQSGLAA GSVKQ                                       325

SEQ ID NO: 21          moltype = AA  length = 469
FEATURE                Location/Qualifiers
source                 1..469
                       mol_type = protein
                       organism = Bifidobacterium longum
SEQUENCE: 21
MTHKGVIMKK SIRLIAAVAA LAMTAGAAAC GSGTSQKNNK ADVSLNDINS ALTDTSKTTD  60
LTVWAYSAKQ IEGPVKAFQE RYPHIKINFV NTGAASDHFT KFQNVVSANK GVPDVVQMSI  120
SEYEQYAVSG ALLNFESDEI EKAWGTQYAQ AAWKNVHFGG GLYGTPQDAA PLALYVRKDI  180
LDEHGLKVPT TWQEFYDEGV KLHKQDPSKY MGFISSSDTS LFGVLRTVGA KPWTVKDTTN  240
IDFSLTTGRV AEFIKFIQKC LDDGVLRAAA TGTDEFNREV NDGVYATRLE GCWQGNIYKD  300
QNPSLKGKMV VAHPLAWGND GESYQSESTG SMFSVSSATP KDKQAAALAF IQWVNGSKDG  360
VSEFLTANKG NYFMASNYYQ KDKSKRDQQE TDGYFANTNV NEIYFESMDK VNMDWDYIPF  420
PAQLTVAFGD TVAPALTGKG DLLTAFTKLQ DNLKSYAEDN GFKVTTDAD             469

SEQ ID NO: 22          moltype = AA  length = 460
FEATURE                Location/Qualifiers
source                 1..460
                       mol_type = protein
                       organism = Bifidobacterium longum
SEQUENCE: 22
MKKSIRLVAA IAALAMTAGI SACGSSTNGN QAKSDVTAQD VENALTDTSK NVELTVWAYS  60
AKQMEPTVKA FEKKYPHIKI NFVNTGAAED HFTKFQNVVQ AQKDIPDVVQ MSANKFQQFA  120
VSGALLNFAN DSIEKAWSKL YTKTAWAQVH YAGGLYGAPQ DATPLANYVR KDILDEHNLQ  180
VPESWEDIYN EGIKLHKEDS NKYMGILGSD ISFFTNLYRS VGARLWKVNS VDDVELTMNS  240
GKAKEFTEFL QKCLKDGVLE GGTVFTDEFN RSINDGRYAT FINENWMGNT YKEQNPSLKG  300
KMVVAAPPSW KGQPYQSSSV GSMMSVSAAC PKEKQAAALA FINWLDSDKD AIQSWQDTNN  360
GNFFMAASVY QDDENQRNKK ETDGYYANDD VNAVYFDSMD KVNTDWEYLP FMSQVEVVFN  420
DVIVPEMNEN GDLVGAMAKA QQKLKAYAED NGFKVTTDAD                        460

SEQ ID NO: 23          moltype = AA  length = 325
FEATURE                Location/Qualifiers
source                 1..325
```

```
                       mol_type = protein
                       organism = Bifidobacterium longum
SEQUENCE: 23
MSEAIARPRS KSLQRRDAKL ALKASKHYKR MQQREPAPKL TGKQRVLNWL LHIIMAVMVI  60
YCLVPLLWVV FSSTKTSEGI FSSFGLWFDD KNVFWQNVQD TFAYQHGVYT RWLFNTIMYA  120
VVAGVGATII ATFAGYAIAT MRFPGRNALL AVTLAFMSIP STVITVPLFL MYSKIGLVGT  180
PWAVIIPQLA TPFGLYLMII YAQTSIPVSL IEAAKLDGAN TWTIFWKVGF PLLSPGFVTV  240
LLFTLVGVWN NYFLPLIMLT NTNDYPLTVG LNMWLKMGAQ GTSDGQVPNN LIITGSLIAV  300
VPLIIAFMFL QKYWQSGLAA GSVKQ                                       325

SEQ ID NO: 24          moltype = AA  length = 303
FEATURE                Location/Qualifiers
source                 1..303
                       mol_type = protein
                       organism = Bifidobacterium longum
SEQUENCE: 24
MTNATAQPDT SVMRKPKRQY IGILYCLPYV VVFLFGMIVP MFYALYLSFF KQSLLGGTTF  60
AGFDNFIRAF KDEALWGGFR NVLIYAAIQI PMNLILSLVA ALVLDSQRIR HIAVPRILLF  120
LPYAVPGVIA ALMWGYIYGD KYGLFGQIAG MFGVAAPNML SKQLMLFAIA NICTWCFLGY  180
NMLIYYSALI GIPNDLYESA RIDGASELRI AWSVKIPQIK STIVMTVLFS VIGTLQLFNE  240
PNILRTSAPD VINSSYTPNI YTYNLAFNGQ NVNYAAAVSL VIGIIVMALV AVVKIIGNKW  300
ENK                                                               303

SEQ ID NO: 25          moltype = AA  length = 142
FEATURE                Location/Qualifiers
source                 1..142
                       mol_type = protein
                       organism = Bacillus subtilis
SEQUENCE: 25
MLKGIPAILS PDLMKVLMEM GHGDEIVLAD GNFPSASHAQ NLLRCDGHGI PALLEAILKF  60
FPLDTYVEHP VTLMDVVEGE QFQPTIWQDF EKVIQKEHGP ALQMEYLDRF TFYERAKKAY  120
AIVATGEAAQ YANIILKKGV VK                                          142

SEQ ID NO: 26          moltype = AA  length = 1019
FEATURE                Location/Qualifiers
source                 1..1019
                       mol_type = protein
                       organism = Bacillus subtilis
SEQUENCE: 26
MEVTDVRLRV DRENPGVTQL NRLAAHPPFA SWRNSEEART DRPSQQLRSL NGEWRFAWFP  60
APEAVPESWL ECDLPEADTV VVPSNWQMHG YDAPIYTNVT YPITVNPPFV PTENPTGCYS  120
LTFNVDESWL QEGQTRIIFD GVNSAFHLWC NGRWVGYGQD SRLPSEFDLS AFLRAGENRL  180
AVMVLRWSDG SYLEDQDMWR MSGIFRDVSL LHKPTTQISD FHVATRFNDD FSRAVLEAEV  240
QMCGELRDYL RVTVSLWQGE TQVASGTAPF GGEIIDERGG YADRVTLRLN VENPKLWSAE  300
IPNLYRAVVE LHTADGTLIE AEACDVGFRE VRIENGLLLL NGKPLLIRGV NRHEHHPLHG  360
QVMDEQTMVQ DILLMKQNNF NAVRCSHYPN HPLWYTLCDR YGLYVVDEAN IETHGMVPMN  420
RLTDDPRWLP AMSERVTRMV QRDRNHPSVI IWSLGNESGH GANHDALYRW IKSVDPSRPV  480
QYEGGGADTT ATDIICPMYA RVDEDQPFPA VPKWSIKKWL SLPGETRPLI LCEYAHAMGN  540
SLGGFAKYWQ AFRQYPRLQG GFVWDWVDQS LIKYDENGNP WSAYGGDFGD TPNDRQFCMN  600
GLVFADRTPH PALTEAKHQQ QFFQFRLSGQ TIEVTSEYLF RHSDNELLHW MVALDGKPLA  660
SGEVPLDVAP QGKQLIELPE LPQPESAGQL WLTVRVVQPN ATAWSEAGHI SAWQQWRLAE  720
NLSVTLPAAS HAIPHLTTSE MDFCIELGNK RWQFNRQSGF LSQMWIGDKK QLLTPLRDQF  780
TRAPLDNDIG VSEATRIDPN AWVERWKAAG HYQAEAALLQ CTADTLADAV LITTAHAWQH  840
QGKTLFISRK TYRIDGSGQM AITVDVEVAS DTPHPARIGL NCQLAQVAER VNWLGLGPQE  900
NYPDRLTAAC FDRWDLPLSD MYTPYVFPSE NGLRCGTREL NYGPHQWRGD FQFNISRYSQ  960
QQLMETSHRH LLHAEEGTWL NIDGFHMGIG GDDSWSPSVS AELQLSAGRY HYQLVWCQK   1019

SEQ ID NO: 27          moltype = DNA  length = 21
FEATURE                Location/Qualifiers
misc_feature           1..21
                       note = Description of Artificial Sequence: Synthetic
                        oligonucleotide
source                 1..21
                       mol_type = other DNA
                       organism = synthetic construct
SEQUENCE: 27
gtcttgtcga tcaggatgat c                                           21

SEQ ID NO: 28          moltype = DNA  length = 22
FEATURE                Location/Qualifiers
misc_feature           1..22
                       note = Description of Artificial Sequence: Synthetic
                        oligonucleotide
source                 1..22
                       mol_type = other DNA
                       organism = synthetic construct
SEQUENCE: 28
cgagcccgta taaactgaaa gc                                          22
```

```
SEQ ID NO: 29          moltype = DNA  length = 23
FEATURE                Location/Qualifiers
misc_feature           1..23
                       note = Description of Artificial Sequence: Synthetic
                        oligonucleotide
source                 1..23
                       mol_type = other DNA
                       organism = synthetic construct
SEQUENCE: 29
ctaggtctag ggcggcggat ttg                                          23

SEQ ID NO: 30          moltype = DNA  length = 23
FEATURE                Location/Qualifiers
misc_feature           1..23
                       note = Description of Artificial Sequence: Synthetic
                        oligonucleotide
source                 1..23
                       mol_type = other DNA
                       organism = synthetic construct
SEQUENCE: 30
cgtaagatac tgacagaaaa cgc                                          23

SEQ ID NO: 31          moltype = DNA  length = 22
FEATURE                Location/Qualifiers
misc_feature           1..22
                       note = Description of Artificial Sequence: Synthetic
                        oligonucleotide
source                 1..22
                       mol_type = other DNA
                       organism = synthetic construct
SEQUENCE: 31
ggaggaagga aagaatatct gg                                           22

SEQ ID NO: 32          moltype = DNA  length = 23
FEATURE                Location/Qualifiers
misc_feature           1..23
                       note = Description of Artificial Sequence: Synthetic
                        oligonucleotide
source                 1..23
                       mol_type = other DNA
                       organism = synthetic construct
SEQUENCE: 32
gtgactttat tggctgctat tcc                                          23

SEQ ID NO: 33          moltype = DNA  length = 22
FEATURE                Location/Qualifiers
misc_feature           1..22
                       note = Description of Artificial Sequence: Synthetic
                        oligonucleotide
source                 1..22
                       mol_type = other DNA
                       organism = synthetic construct
SEQUENCE: 33
caaatagggg ttccgcgcac at                                           22

SEQ ID NO: 34          moltype = DNA  length = 21
FEATURE                Location/Qualifiers
misc_feature           1..21
                       note = Description of Artificial Sequence: Synthetic
                        oligonucleotide
source                 1..21
                       mol_type = other DNA
                       organism = synthetic construct
SEQUENCE: 34
gatatgactg ttctcgatcc a                                            21

SEQ ID NO: 35          moltype = DNA  length = 20
FEATURE                Location/Qualifiers
misc_feature           1..20
                       note = Description of Artificial Sequence: Synthetic
                        oligonucleotide
source                 1..20
                       mol_type = other DNA
                       organism = synthetic construct
SEQUENCE: 35
ccctggcaaa tgttgattga                                              20

SEQ ID NO: 36          moltype = DNA  length = 20
FEATURE                Location/Qualifiers
```

```
misc_feature            1..20
                        note = Description of Artificial Sequence: Synthetic
                         oligonucleotide
source                  1..20
                        mol_type = other DNA
                        organism = synthetic construct
SEQUENCE: 36
caggctgtta ccaaagaagt                                              20

SEQ ID NO: 37           moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 37
cggccttatt gtctctctgc                                              20

SEQ ID NO: 38           moltype = DNA  length = 24
FEATURE                 Location/Qualifiers
misc_feature            1..24
                        note = Description of Artificial Sequence: Synthetic
                         oligonucleotide
source                  1..24
                        mol_type = other DNA
                        organism = synthetic construct
SEQUENCE: 38
cctaggtcta gggcggcgga tttg                                         24

SEQ ID NO: 39           moltype = DNA  length = 24
FEATURE                 Location/Qualifiers
misc_feature            1..24
                        note = Description of Artificial Sequence: Synthetic
                         oligonucleotide
source                  1..24
                        mol_type = other DNA
                        organism = synthetic construct
SEQUENCE: 39
cattataaca ttcttcaagc agcc                                         24

SEQ ID NO: 40           moltype = DNA  length = 40
FEATURE                 Location/Qualifiers
misc_feature            1..40
                        note = Description of Artificial Sequence: Synthetic
                         oligonucleotide
source                  1..40
                        mol_type = other DNA
                        organism = synthetic construct
SEQUENCE: 40
aattcattaa agaggagaaa agatatacca tgggcagcag                        40

SEQ ID NO: 41           moltype = DNA  length = 43
FEATURE                 Location/Qualifiers
misc_feature            1..43
                        note = Description of Artificial Sequence: Synthetic
                         oligonucleotide
source                  1..43
                        mol_type = other DNA
                        organism = synthetic construct
SEQUENCE: 41
catatgtata tctccttctt ttatgatcgt gatacttgga atc                    43

SEQ ID NO: 42           moltype = DNA  length = 31
FEATURE                 Location/Qualifiers
misc_feature            1..31
                        note = Description of Artificial Sequence: Synthetic
                         oligonucleotide
source                  1..31
                        mol_type = other DNA
                        organism = synthetic construct
SEQUENCE: 42
aagaaggaga tatacatatg agcattattc g                                 31

SEQ ID NO: 43           moltype = DNA  length = 20
FEATURE                 Location/Qualifiers
misc_feature            1..20
                        note = Description of Artificial Sequence: Synthetic
```

```
                        oligonucleotide
source                  1..20
                        mol_type = other DNA
                        organism = synthetic construct
SEQUENCE: 43
ttagcagccg gatctcagtg                                              20

SEQ ID NO: 44           moltype = DNA  length = 41
FEATURE                 Location/Qualifiers
misc_feature            1..41
                        note = Description of Artificial Sequence: Synthetic
                         oligonucleotide
source                  1..41
                        mol_type = other DNA
                        organism = synthetic construct
SEQUENCE: 44
cactgagatc cggctgctaa ggtacctaat ctagaggcat c                      41

SEQ ID NO: 45           moltype = DNA  length = 34
FEATURE                 Location/Qualifiers
misc_feature            1..34
                        note = Description of Artificial Sequence: Synthetic
                         oligonucleotide
source                  1..34
                        mol_type = other DNA
                        organism = synthetic construct
SEQUENCE: 45
tttctcctct ttaatgaatt cggtcagtgc gtcc                              34

SEQ ID NO: 46           moltype = DNA  length = 41
FEATURE                 Location/Qualifiers
misc_feature            1..41
                        note = Description of Artificial Sequence: Synthetic
                         oligonucleotide
source                  1..41
                        mol_type = other DNA
                        organism = synthetic construct
SEQUENCE: 46
aattcattaa agaggagaaa catatgttcc aaccgctgct g                      41

SEQ ID NO: 47           moltype = DNA  length = 40
FEATURE                 Location/Qualifiers
misc_feature            1..40
                        note = Description of Artificial Sequence: Synthetic
                         oligonucleotide
source                  1..40
                        mol_type = other DNA
                        organism = synthetic construct
SEQUENCE: 47
ctctagagtc attaggtacc gctttgttag cagccggatc                        40

SEQ ID NO: 48           moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 48
tttctcctct ttaatgaatt cgg                                          23

SEQ ID NO: 49           moltype = DNA  length = 24
FEATURE                 Location/Qualifiers
misc_feature            1..24
                        note = Description of Artificial Sequence: Synthetic
                         oligonucleotide
source                  1..24
                        mol_type = other DNA
                        organism = synthetic construct
SEQUENCE: 49
gaattcggtc agtgcgtcct gctg                                         24

SEQ ID NO: 50           moltype = DNA  length = 40
FEATURE                 Location/Qualifiers
misc_feature            1..40
                        note = Description of Artificial Sequence: Synthetic
                         oligonucleotide
source                  1..40
```

```
                        mol_type = other DNA
                        organism = synthetic construct
SEQUENCE: 50
aaggatccgg ctgctaacaa aaggagatat acatatgagc                          40

SEQ ID NO: 51           moltype = DNA  length = 38
FEATURE                 Location/Qualifiers
misc_feature            1..38
                        note = Description of Artificial Sequence: Synthetic
                         oligonucleotide
source                  1..38
                        mol_type = other DNA
                        organism = synthetic construct
SEQUENCE: 51
actcagcttc ctttcgggct agcagccgga tctcagtg                            38

SEQ ID NO: 52           moltype = DNA  length = 29
FEATURE                 Location/Qualifiers
misc_feature            1..29
                        note = Description of Artificial Sequence: Synthetic
                         oligonucleotide
source                  1..29
                        mol_type = other DNA
                        organism = synthetic construct
SEQUENCE: 52
agcccgaaag gaagctgagt tggctgctg                                      29

SEQ ID NO: 53           moltype = DNA  length = 36
FEATURE                 Location/Qualifiers
misc_feature            1..36
                        note = Description of Artificial Sequence: Synthetic
                         oligonucleotide
source                  1..36
                        mol_type = other DNA
                        organism = synthetic construct
SEQUENCE: 53
ttgttagcag ccggatcctt atgatcgtga tacttg                              36

SEQ ID NO: 54           moltype = DNA  length = 26
FEATURE                 Location/Qualifiers
misc_feature            1..26
                        note = Description of Artificial Sequence: Synthetic
                         oligonucleotide
source                  1..26
                        mol_type = other DNA
                        organism = synthetic construct
SEQUENCE: 54
atgattgaac aagatggatt gcacgc                                         26

SEQ ID NO: 55           moltype = DNA  length = 36
FEATURE                 Location/Qualifiers
misc_feature            1..36
                        note = Description of Artificial Sequence: Synthetic
                         oligonucleotide
source                  1..36
                        mol_type = other DNA
                        organism = synthetic construct
SEQUENCE: 55
aggagagcgt tcaccgacaa aacgccagca acgcgg                              36

SEQ ID NO: 56           moltype = DNA  length = 59
FEATURE                 Location/Qualifiers
misc_feature            1..59
                        note = Description of Artificial Sequence: Synthetic
                         oligonucleotide
source                  1..59
                        mol_type = other DNA
                        organism = synthetic construct
SEQUENCE: 56
aatccatctt gttcaatcat actcttcctt tttcaatatt attgaagcat ttatcaggg   59

SEQ ID NO: 57           moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
```

```
SEQUENCE: 57
cactttacta cccacgccgc                                          20

SEQ ID NO: 58           moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 58
gactggcagc aacaggtggc                                          20

SEQ ID NO: 59           moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 59
gttgagctac aggcggtcag                                          20

SEQ ID NO: 60           moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 60
atttactaac tggaagaggc                                          20

SEQ ID NO: 61           moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 61
cattgagtca accggaatgg                                          20

SEQ ID NO: 62           moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 62
aaaccaatcg gtaaggaagg                                          20

SEQ ID NO: 63           moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 63
ttttaccgtt cacgcgctgg                                          20

SEQ ID NO: 64           moltype = DNA  length = 42
FEATURE                 Location/Qualifiers
misc_feature            1..42
                        note = Description of Artificial Sequence: Synthetic
                         oligonucleotide
source                  1..42
                        mol_type = other DNA
                        organism = synthetic construct
SEQUENCE: 64
tggtgccgcg cggcagccat atgggtcatc accaccatca tc                 42
```

```
SEQ ID NO: 65          moltype = DNA  length = 45
FEATURE                Location/Qualifiers
misc_feature           1..45
                       note = Description of Artificial Sequence: Synthetic
                        oligonucleotide
source                 1..45
                       mol_type = other DNA
                       organism = synthetic construct
SEQUENCE: 65
ttcgggctag cagccggatc ttatttgtac agttcgtcca tgccg                  45

SEQ ID NO: 66          moltype = DNA  length = 38
FEATURE                Location/Qualifiers
misc_feature           1..38
                       note = Description of Artificial Sequence: Synthetic
                        oligonucleotide
source                 1..38
                       mol_type = other DNA
                       organism = synthetic construct
SEQUENCE: 66
gatccggctg ctagcccgaa aggaagctga gttggctg                          38

SEQ ID NO: 67          moltype = DNA  length = 21
FEATURE                Location/Qualifiers
misc_feature           1..21
                       note = Description of Artificial Sequence: Synthetic
                        oligonucleotide
source                 1..21
                       mol_type = other DNA
                       organism = synthetic construct
SEQUENCE: 67
atggctgccg cgcggcacca g                                            21

SEQ ID NO: 68          moltype = DNA  length = 23
FEATURE                Location/Qualifiers
misc_feature           1..23
                       note = Description of Artificial Sequence: Synthetic
                        oligonucleotide
source                 1..23
                       mol_type = other DNA
                       organism = synthetic construct
SEQUENCE: 68
aatgcgcgcc attaccgagt ccg                                          23

SEQ ID NO: 69          moltype = DNA  length = 30
FEATURE                Location/Qualifiers
misc_feature           1..30
                       note = Description of Artificial Sequence: Synthetic
                        oligonucleotide
source                 1..30
                       mol_type = other DNA
                       organism = synthetic construct
SEQUENCE: 69
agctgtttcc tgtgtgaaat tgttatccgc                                   30

SEQ ID NO: 70          moltype = DNA  length = 44
FEATURE                Location/Qualifiers
misc_feature           1..44
                       note = Description of Artificial Sequence: Synthetic
                        oligonucleotide
source                 1..44
                       mol_type = other DNA
                       organism = synthetic construct
SEQUENCE: 70
atttcacaca ggaaacagct taataaccgg gcaggccatg tctg                   44

SEQ ID NO: 71          moltype = DNA  length = 35
FEATURE                Location/Qualifiers
misc_feature           1..35
                       note = Description of Artificial Sequence: Synthetic
                        oligonucleotide
source                 1..35
                       mol_type = other DNA
                       organism = synthetic construct
SEQUENCE: 71
actttctcaa taaatgcctc tactgctggc gcacc                             35

SEQ ID NO: 72          moltype = DNA  length = 58
```

```
FEATURE                Location/Qualifiers
misc_feature           1..58
                       note = Description of Artificial Sequence: Synthetic
                        oligonucleotide
source                 1..58
                       mol_type = other DNA
                       organism = synthetic construct
SEQUENCE: 72
gaggcattta ttgagaaagt taatctagag gcatcaaata aaacgaaagg ctcagtcg    58

SEQ ID NO: 73          moltype = DNA  length = 41
FEATURE                Location/Qualifiers
misc_feature           1..41
                       note = Description of Artificial Sequence: Synthetic
                        oligonucleotide
source                 1..41
                       mol_type = other DNA
                       organism = synthetic construct
SEQUENCE: 73
actcggtaat ggcgcgcatt ggtcagtgcg tcctgctgat g                      41

SEQ ID NO: 74          moltype = DNA  length = 29
FEATURE                Location/Qualifiers
misc_feature           1..29
                       note = Description of Artificial Sequence: Synthetic
                        oligonucleotide
source                 1..29
                       mol_type = other DNA
                       organism = synthetic construct
SEQUENCE: 74
gccgacacca gttttagagc tagaaatag                                    29

SEQ ID NO: 75          moltype = DNA  length = 34
FEATURE                Location/Qualifiers
misc_feature           1..34
                       note = Description of Artificial Sequence: Synthetic
                        oligonucleotide
source                 1..34
                       mol_type = other DNA
                       organism = synthetic construct
SEQUENCE: 75
tccgccgcct actagtatta tacctaggac tgag                              34

SEQ ID NO: 76          moltype = DNA  length = 40
FEATURE                Location/Qualifiers
misc_feature           1..40
                       note = Description of Artificial Sequence: Synthetic
                        oligonucleotide
source                 1..40
                       mol_type = other DNA
                       organism = synthetic construct
SEQUENCE: 76
cagcggtgga gtgcaatgtc atgagtattc aacatttccg                        40

SEQ ID NO: 77          moltype = DNA  length = 40
FEATURE                Location/Qualifiers
misc_feature           1..40
                       note = Description of Artificial Sequence: Synthetic
                        oligonucleotide
source                 1..40
                       mol_type = other DNA
                       organism = synthetic construct
SEQUENCE: 77
atcgactggc gagcggcatc ttaccaatgc ttaatcagtg                        40

SEQ ID NO: 78          moltype = DNA  length = 24
FEATURE                Location/Qualifiers
misc_feature           1..24
                       note = Description of Artificial Sequence: Synthetic
                        oligonucleotide
source                 1..24
                       mol_type = other DNA
                       organism = synthetic construct
SEQUENCE: 78
gatgccgctc gccagtcgat tggc                                         24

SEQ ID NO: 79          moltype = DNA  length = 25
FEATURE                Location/Qualifiers
misc_feature           1..25
```

```
                        note = Description of Artificial Sequence: Synthetic
                         oligonucleotide
source                  1..25
                        mol_type = other DNA
                        organism = synthetic construct
SEQUENCE: 79
gacattgcac tccaccgctg atgac                                       25

SEQ ID NO: 80           moltype = DNA  length = 33
FEATURE                 Location/Qualifiers
misc_feature            1..33
                        note = Description of Artificial Sequence: Synthetic
                         oligonucleotide
source                  1..33
                        mol_type = other DNA
                        organism = synthetic construct
SEQUENCE: 80
tccggattta ctaactggaa gaggcactaa atg                              33

SEQ ID NO: 81           moltype = DNA  length = 32
FEATURE                 Location/Qualifiers
misc_feature            1..32
                        note = Description of Artificial Sequence: Synthetic
                         oligonucleotide
source                  1..32
                        mol_type = other DNA
                        organism = synthetic construct
SEQUENCE: 81
agctgtttcc tgtgtgaaat tgttatccgc tc                               32

SEQ ID NO: 82           moltype = DNA  length = 42
FEATURE                 Location/Qualifiers
misc_feature            1..42
                        note = Description of Artificial Sequence: Synthetic
                         oligonucleotide
source                  1..42
                        mol_type = other DNA
                        organism = synthetic construct
SEQUENCE: 82
cctttcgtct tcacctcgag tcactcatta ggcaccccag gc                    42

SEQ ID NO: 83           moltype = DNA  length = 42
FEATURE                 Location/Qualifiers
misc_feature            1..42
                        note = Description of Artificial Sequence: Synthetic
                         oligonucleotide
source                  1..42
                        mol_type = other DNA
                        organism = synthetic construct
SEQUENCE: 83
ggtaccttag cagccggatc ttacgcgaac gcgaagtccg ac                    42

SEQ ID NO: 84           moltype = DNA  length = 32
FEATURE                 Location/Qualifiers
misc_feature            1..32
                        note = Description of Artificial Sequence: Synthetic
                         oligonucleotide
source                  1..32
                        mol_type = other DNA
                        organism = synthetic construct
SEQUENCE: 84
gatccggctg ctaaggtacc taatctagag gc                               32

SEQ ID NO: 85           moltype = DNA  length = 24
FEATURE                 Location/Qualifiers
misc_feature            1..24
                        note = Description of Artificial Sequence: Synthetic
                         oligonucleotide
source                  1..24
                        mol_type = other DNA
                        organism = synthetic construct
SEQUENCE: 85
ctcgaggtga agacgaaagg gcct                                        24

SEQ ID NO: 86           moltype = DNA  length = 42
FEATURE                 Location/Qualifiers
misc_feature            1..42
                        note = Description of Artificial Sequence: Synthetic
                         oligonucleotide
```

```
source                  1..42
                        mol_type = other DNA
                        organism = synthetic construct
SEQUENCE: 86
agttgatatg tcaaacaggt tcactcatta ggcaccccag gc                    42

SEQ ID NO: 87           moltype = DNA  length = 42
FEATURE                 Location/Qualifiers
misc_feature            1..42
                        note = Description of Artificial Sequence: Synthetic
                         oligonucleotide
source                  1..42
                        mol_type = other DNA
                        organism = synthetic construct
SEQUENCE: 87
cggcgctcag ttggaattca acaacagata aaacgaaagg cc                    42

SEQ ID NO: 88           moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 88
tgaattccaa ctgagcgccg gtc                                         23

SEQ ID NO: 89           moltype = DNA  length = 25
FEATURE                 Location/Qualifiers
misc_feature            1..25
                        note = Description of Artificial Sequence: Synthetic
                         oligonucleotide
source                  1..25
                        mol_type = other DNA
                        organism = synthetic construct
SEQUENCE: 89
acctgtttga catatcaact gcgcc                                       25

SEQ ID NO: 90           moltype = DNA  length = 30
FEATURE                 Location/Qualifiers
misc_feature            1..30
                        note = Description of Artificial Sequence: Synthetic
                         oligonucleotide
source                  1..30
                        mol_type = other DNA
                        organism = synthetic construct
SEQUENCE: 90
gtgatgatgg gttttagagc tagaaatagc                                  30

SEQ ID NO: 91           moltype = DNA  length = 30
FEATURE                 Location/Qualifiers
misc_feature            1..30
                        note = Description of Artificial Sequence: Synthetic
                         oligonucleotide
source                  1..30
                        mol_type = other DNA
                        organism = synthetic construct
SEQUENCE: 91
cagcggcggt actagtatta tacctaggac                                  30

SEQ ID NO: 92           moltype = DNA  length = 39
FEATURE                 Location/Qualifiers
misc_feature            1..39
                        note = Description of Artificial Sequence: Synthetic
                         oligonucleotide
source                  1..39
                        mol_type = other DNA
                        organism = synthetic construct
SEQUENCE: 92
actcttcctt tttcaatatt attgaagcat ttatcaggg                        39

SEQ ID NO: 93           moltype = DNA  length = 30
FEATURE                 Location/Qualifiers
misc_feature            1..30
                        note = Description of Artificial Sequence: Synthetic
                         oligonucleotide
source                  1..30
                        mol_type = other DNA
```

```
                         organism = synthetic construct
SEQUENCE: 93
cgcgcggcac actagtatta tacctaggac                                       30

SEQ ID NO: 94            moltype = DNA  length = 47
FEATURE                  Location/Qualifiers
misc_feature             1..47
                         note = Description of Artificial Sequence: Synthetic
                          oligonucleotide
source                   1..47
                         mol_type = other DNA
                         organism = synthetic construct
SEQUENCE: 94
gtgccacctg acgtctaaga ctagtactct agtatttctc ctcttta                    47

SEQ ID NO: 95            moltype = DNA  length = 60
FEATURE                  Location/Qualifiers
misc_feature             1..60
                         note = Description of Artificial Sequence: Synthetic
                          oligonucleotide
source                   1..60
                         mol_type = other DNA
                         organism = synthetic construct
SEQUENCE: 95
gctactagag tactagagta ctagagatta aagaggagaa atactagagt actagtctta  60

SEQ ID NO: 96            moltype = DNA  length = 57
FEATURE                  Location/Qualifiers
misc_feature             1..57
                         note = Description of Artificial Sequence: Synthetic
                          oligonucleotide
source                   1..57
                         mol_type = other DNA
                         organism = synthetic construct
SEQUENCE: 96
tctctagtac tctagtactc tagtagctag cactgtacct aggactgagc tagccgt     57

SEQ ID NO: 97            moltype = DNA  length = 59
FEATURE                  Location/Qualifiers
misc_feature             1..59
                         note = Description of Artificial Sequence: Synthetic
                          oligonucleotide
source                   1..59
                         mol_type = other DNA
                         organism = synthetic construct
SEQUENCE: 97
acgcctattt ttataggtta atgtcatgat aataatggtt ttgacggcta gctcagtcc   59

SEQ ID NO: 98            moltype = DNA  length = 59
FEATURE                  Location/Qualifiers
misc_feature             1..59
                         note = Description of Artificial Sequence: Synthetic
                          oligonucleotide
source                   1..59
                         mol_type = other DNA
                         organism = synthetic construct
SEQUENCE: 98
tgacattaac ctataaaaat aggcgtatca cgaggccctt tcgtcttcac ctcgagaat   59

SEQ ID NO: 99            moltype = DNA  length = 59
FEATURE                  Location/Qualifiers
misc_feature             1..59
                         note = Description of Artificial Sequence: Synthetic
                          oligonucleotide
source                   1..59
                         mol_type = other DNA
                         organism = synthetic construct
SEQUENCE: 99
ttgttatccg ctcacaatgt caattgttat ccgctcacaa ttctcgaggt gaagacgaa   59

SEQ ID NO: 100           moltype = DNA  length = 27
FEATURE                  Location/Qualifiers
misc_feature             1..27
                         note = Description of Artificial Sequence: Synthetic
                          oligonucleotide
source                   1..27
                         mol_type = other DNA
                         organism = synthetic construct
SEQUENCE: 100
```

```
caattgacat tgtgagcgga taacaag                                    27

SEQ ID NO: 101         moltype = DNA  length = 26
FEATURE                Location/Qualifiers
misc_feature           1..26
                       note = Description of Artificial Sequence: Synthetic
                        oligonucleotide
source                 1..26
                       mol_type = other DNA
                       organism = synthetic construct
SEQUENCE: 101
tcttagacgt caggtggcac ttttcg                                     26

SEQ ID NO: 102         moltype = DNA  length = 41
FEATURE                Location/Qualifiers
misc_feature           1..41
                       note = Description of Artificial Sequence: Synthetic
                        oligonucleotide
source                 1..41
                       mol_type = other DNA
                       organism = synthetic construct
SEQUENCE: 102
gtgccacctg acgtctaaga ttaagcgact tcattcacct g                    41

SEQ ID NO: 103         moltype = DNA  length = 53
FEATURE                Location/Qualifiers
misc_feature           1..53
                       note = Description of Artificial Sequence: Synthetic
                        oligonucleotide
source                 1..53
                       mol_type = other DNA
                       organism = synthetic construct
SEQUENCE: 103
gagaaatact agagtactag atgtactatt taaaaaacac aaacttttgg atg        53

SEQ ID NO: 104         moltype = DNA  length = 38
FEATURE                Location/Qualifiers
misc_feature           1..38
                       note = Description of Artificial Sequence: Synthetic
                        oligonucleotide
source                 1..38
                       mol_type = other DNA
                       organism = synthetic construct
SEQUENCE: 104
ctagtactct agtatttctc ctctttaatc tctagtac                         38

SEQ ID NO: 105         moltype = DNA  length = 43
FEATURE                Location/Qualifiers
misc_feature           1..43
                       note = Description of Artificial Sequence: Synthetic
                        oligonucleotide
source                 1..43
                       mol_type = other DNA
                       organism = synthetic construct
SEQUENCE: 105
gtgccacctg acgtctaaga tcagttagtt gccgtttgag aac                   43

SEQ ID NO: 106         moltype = DNA  length = 49
FEATURE                Location/Qualifiers
misc_feature           1..49
                       note = Description of Artificial Sequence: Synthetic
                        oligonucleotide
source                 1..49
                       mol_type = other DNA
                       organism = synthetic construct
SEQUENCE: 106
gagaaatact agagtactag atgggaaaca catcaataca aacgcagag             49

SEQ ID NO: 107         moltype = DNA  length = 44
FEATURE                Location/Qualifiers
misc_feature           1..44
                       note = Description of Artificial Sequence: Synthetic
                        oligonucleotide
source                 1..44
                       mol_type = other DNA
                       organism = synthetic construct
SEQUENCE: 107
gaaagagggg acaaactagt atgggaaaca catcaataca aacg                  44
```

-continued

```
SEQ ID NO: 108         moltype = DNA  length = 44
FEATURE                Location/Qualifiers
misc_feature           1..44
                       note = Description of Artificial Sequence: Synthetic
                        oligonucleotide
source                 1..44
                       mol_type = other DNA
                       organism = synthetic construct
SEQUENCE: 108
ttgtcccctc tttctctaga ttaagcgact tcattcacct gacg                   44

SEQ ID NO: 109         moltype = DNA  length = 45
FEATURE                Location/Qualifiers
misc_feature           1..45
                       note = Description of Artificial Sequence: Synthetic
                        oligonucleotide
source                 1..45
                       mol_type = other DNA
                       organism = synthetic construct
SEQUENCE: 109
ctaactggaa gaggcactaa atgggtcatc accaccatca tcacg                  45

SEQ ID NO: 110         moltype = DNA  length = 45
FEATURE                Location/Qualifiers
misc_feature           1..45
                       note = Description of Artificial Sequence: Synthetic
                        oligonucleotide
source                 1..45
                       mol_type = other DNA
                       organism = synthetic construct
SEQUENCE: 110
ggtaccttag cagccggatc ttatttgtac agttcgtcca tgccg                  45

SEQ ID NO: 111         moltype = DNA  length = 25
FEATURE                Location/Qualifiers
misc_feature           1..25
                       note = Description of Artificial Sequence: Synthetic
                        oligonucleotide
source                 1..25
                       mol_type = other DNA
                       organism = synthetic construct
SEQUENCE: 111
gatccggctg ctaaggtacc taatc                                        25

SEQ ID NO: 112         moltype = DNA  length = 29
FEATURE                Location/Qualifiers
misc_feature           1..29
                       note = Description of Artificial Sequence: Synthetic
                        oligonucleotide
source                 1..29
                       mol_type = other DNA
                       organism = synthetic construct
SEQUENCE: 112
ttagtgcctc ttccagttag taaatccgg                                    29

SEQ ID NO: 113         moltype = DNA  length = 28
FEATURE                Location/Qualifiers
misc_feature           1..28
                       note = Description of Artificial Sequence: Synthetic
                        oligonucleotide
source                 1..28
                       mol_type = other DNA
                       organism = synthetic construct
SEQUENCE: 113
ctgctaaggt acctaatcta gaggcatc                                     28

SEQ ID NO: 114         moltype = DNA  length = 30
FEATURE                Location/Qualifiers
misc_feature           1..30
                       note = Description of Artificial Sequence: Synthetic
                        oligonucleotide
source                 1..30
                       mol_type = other DNA
                       organism = synthetic construct
SEQUENCE: 114
ccggatctta tgatcgtgat acttggaatc                                   30

SEQ ID NO: 115         moltype = DNA  length = 19
FEATURE                Location/Qualifiers
```

```
misc_feature           1..19
                       note = Description of Artificial Sequence: Synthetic
                        oligonucleotide
source                 1..19
                       mol_type = other DNA
                       organism = synthetic construct
SEQUENCE: 115
ggttccgcgc acatttccc                                                    19

SEQ ID NO: 116         moltype = DNA  length = 20
FEATURE                Location/Qualifiers
misc_feature           1..20
                       note = Description of Artificial Sequence: Synthetic
                        oligonucleotide
source                 1..20
                       mol_type = other DNA
                       organism = synthetic construct
SEQUENCE: 116
gagtcagtga gcgaggaagc                                                   20

SEQ ID NO: 117         moltype = DNA  length = 20
FEATURE                Location/Qualifiers
misc_feature           1..20
                       note = Description of Artificial Sequence: Synthetic
                        oligonucleotide
source                 1..20
                       mol_type = other DNA
                       organism = synthetic construct
SEQUENCE: 117
gcttggttga gaatacgccg                                                   20

SEQ ID NO: 118         moltype = DNA  length = 22
FEATURE                Location/Qualifiers
misc_feature           1..22
                       note = Description of Artificial Sequence: Synthetic
                        oligonucleotide
source                 1..22
                       mol_type = other DNA
                       organism = synthetic construct
SEQUENCE: 118
gcctacgatt acgcatggct tg                                                22

SEQ ID NO: 119         moltype = DNA  length = 23
FEATURE                Location/Qualifiers
misc_feature           1..23
                       note = Description of Artificial Sequence: Synthetic
                        oligonucleotide
source                 1..23
                       mol_type = other DNA
                       organism = synthetic construct
SEQUENCE: 119
ggccctttcg tcttcacctc gag                                               23

SEQ ID NO: 120         moltype = DNA  length = 40
FEATURE                Location/Qualifiers
misc_feature           1..40
                       note = Description of Artificial Sequence: Synthetic
                        oligonucleotide
source                 1..40
                       mol_type = other DNA
                       organism = synthetic construct
SEQUENCE: 120
aacgcagtca ggcaccgtgt atgagtattc aacatttccg                             40

SEQ ID NO: 121         moltype = DNA  length = 40
FEATURE                Location/Qualifiers
misc_feature           1..40
                       note = Description of Artificial Sequence: Synthetic
                        oligonucleotide
source                 1..40
                       mol_type = other DNA
                       organism = synthetic construct
SEQUENCE: 121
gaggtgccgc cggcttccat ttaccaatgc ttaatcagtg                             40

SEQ ID NO: 122         moltype = DNA  length = 20
FEATURE                Location/Qualifiers
misc_feature           1..20
                       note = Description of Artificial Sequence: Synthetic
```

```
                        oligonucleotide
source                  1..20
                        mol_type = other DNA
                        organism = synthetic construct
SEQUENCE: 122
atggaagccg gcggcacctc                                                20

SEQ ID NO: 123          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 123
acacggtgcc tgactgcgtt agc                                            23

SEQ ID NO: 124          moltype = DNA  length = 25
FEATURE                 Location/Qualifiers
misc_feature            1..25
                        note = Description of Artificial Sequence: Synthetic
                         oligonucleotide
source                  1..25
                        mol_type = other DNA
                        organism = synthetic construct
SEQUENCE: 124
taatgactct agaggcatca aataa                                          25

SEQ ID NO: 125          moltype = DNA  length = 21
FEATURE                 Location/Qualifiers
misc_feature            1..21
                        note = Description of Artificial Sequence: Synthetic
                         oligonucleotide
source                  1..21
                        mol_type = other DNA
                        organism = synthetic construct
SEQUENCE: 125
ttgtcggtga acgctctcct g                                              21

SEQ ID NO: 126          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 126
atgggtcatc accaccatca tca                                            23

SEQ ID NO: 127          moltype = DNA  length = 25
FEATURE                 Location/Qualifiers
misc_feature            1..25
                        note = Description of Artificial Sequence: Synthetic
                         oligonucleotide
source                  1..25
                        mol_type = other DNA
                        organism = synthetic construct
SEQUENCE: 127
ccagtagtag gttgaggccg ttgag                                          25

SEQ ID NO: 128          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 128
ctactcagga gagcgttcac                                                20

SEQ ID NO: 129          moltype = DNA  length = 20
FEATURE                 Location/Qualifiers
misc_feature            1..20
                        note = Description of Artificial Sequence: Synthetic
                         oligonucleotide
source                  1..20
```

-continued

```
                        mol_type = other DNA
                        organism = synthetic construct
SEQUENCE: 129
gcttcccaac cttaccagag                                           20

SEQ ID NO: 130          moltype = DNA  length = 21
FEATURE                 Location/Qualifiers
misc_feature            1..21
                        note = Description of Artificial Sequence: Synthetic
                         oligonucleotide
source                  1..21
                        mol_type = other DNA
                        organism = synthetic construct
SEQUENCE: 130
caagcagcag attacgcgca g                                         21

SEQ ID NO: 131          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 131
accgccgctg gtgatgatgg                                           20

SEQ ID NO: 132          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 132
aggcggcgga gccgacacca                                           20

SEQ ID NO: 133          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 133
tctggcgcag ttgatatgta                                           20
```